(12) United States Patent
Jackson et al.

(10) Patent No.: US 11,484,346 B2
(45) Date of Patent: *Nov. 1, 2022

(54) PIVOTAL BONE ANCHOR ASSEMBLY WITH TOOL COMPRESSED INSERT FOR CLOSURE INDEPENDENT LOCKING

(71) Applicant: Roger P. Jackson, Prairie Village, KS (US)

(72) Inventors: Roger P. Jackson, Prairie Village, KS (US); James L. Surber, Kansas City, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 17/522,725

(22) Filed: Nov. 9, 2021

(65) Prior Publication Data

US 2022/0061888 A1  Mar. 3, 2022

Related U.S. Application Data

(63) Continuation of application No. 17/114,214, filed on Dec. 7, 2020, now Pat. No. 11,185,349, which is a continuation of application No. 16/675,431, filed on Nov. 6, 2019, now Pat. No. 10,856,909, which is a continuation of application No. 16/247,378, filed on Jan. 14, 2019, now Pat. No. 10,478,225, which is a
(Continued)

(51) Int. Cl.
*A61B 17/70* (2006.01)
*A61B 17/68* (2006.01)

(52) U.S. Cl.
CPC .......... *A61B 17/68* (2013.01); *A61B 17/7008* (2013.01); *A61B 17/7032* (2013.01); *A61B 17/7037* (2013.01); *A61B 17/7076* (2013.01)

(58) Field of Classification Search
CPC ...... A61B 17/70; A61B 17/7032–7046; A61B 17/7074
See application file for complete search history.

(56) References Cited

U.S. PATENT DOCUMENTS 5,501,684 A   3/1996 Schlapfer
5,584,834 A   12/1996 Errico et al.
(Continued)

*Primary Examiner* — Eduardo C Robert
*Assistant Examiner* — Michelle C Eckman
(74) *Attorney, Agent, or Firm* — Polsinelli PC

(57) ABSTRACT

A pivotal bone anchor assembly includes a receiver comprising a base defining a central opening and upright arms defining an open channel for receiving a rod and including tool engaging structures for releasable overlapping engagement with an insert compressing tool. The assembly further includes a bone anchor comprising a capture head pivotably positionable within the central opening of the base and an anchor portion for fixation to the bone, and a compression insert positionable within the central opening above the capture head and comprising an upper surface engageable with the rod, a center through-bore, and upward-facing tool engagement surfaces located radially outward from the center through-bore. The tool engaging structures of the upright arms and the upward-facing tool engagement surfaces of the insert are configured for simultaneous non-threadable engagement with the insert compressing tool to apply a downwardly-directed force to the capture head to temporarily independently lock an articulated position of the bone anchor with respect to the receiver.

18 Claims, 29 Drawing Sheets

Related U.S. Application Data continuation of application No. 15/893,333, filed on Feb. 9, 2018, now Pat. No. 10,179,010, which is a continuation of application No. 13/373,289, filed on Nov. 9, 2011, now Pat. No. 9,907,574, and a continuation-in-part of application No. 12/924,802, filed on Oct. 5, 2010, now Pat. No. 8,556,938, and a continuation-in-part of application No. 12/802,849, filed on Jun. 15, 2010, now abandoned.

(60) Provisional application No. 61/460,234, filed on Dec. 29, 2010, provisional application No. 61/456,649, filed on Nov. 10, 2010, provisional application No. 61/403,915, filed on Sep. 23, 2010, provisional application No. 61/403,696, filed on Sep. 20, 2010, provisional application No. 61/402,959, filed on Sep. 8, 2010, provisional application No. 61/400,504, filed on Jul. 29, 2010, provisional application No. 61/398,807, filed on Jul. 1, 2010, provisional application No. 61/396,390, filed on May 26, 2010, provisional application No. 61/395,752, filed on May 17, 2010, provisional application No. 61/395,564, filed on May 14, 2010, provisional application No. 61/343,737, filed on May 3, 2010, provisional application No. 61/336,911, filed on Jan. 28, 2010, provisional application No. 61/278,240, filed on Oct. 5, 2009, provisional application No. 61/270,754, filed on Jul. 13, 2009, provisional application No. 61/268,708, filed on Jun. 15, 2009.

(56) References Cited

U.S. PATENT DOCUMENTS

| | | | |
|---|---|---|---|
| 5,672,176 | A | 9/1997 | Biedermann et al. |
| 5,735,853 | A | 4/1998 | Olerud |
| 5,891,145 | A | 4/1999 | Morrison et al. |
| 6,063,090 | A | 5/2000 | Schlapfer |
| 6,146,383 | A | 11/2000 | Studer et al. |
| 6,241,731 | B1 | 6/2001 | Fiz |
| 6,280,442 | B1 | 8/2001 | Barker et al. |
| 6,485,491 | B1 | 11/2002 | Farris et al. |
| 6,626,908 | B2 | 9/2003 | Cooper et al. |
| 6,648,888 | B1 | 11/2003 | Shluzas |
| 6,660,004 | B2 | 12/2003 | Barker et al. |
| 6,716,214 | B1 | 4/2004 | Jackson |
| 6,740,086 | B2 | 5/2004 | Richelsoph |
| 6,837,889 | B2 | 1/2005 | Shluzas |
| 7,001,389 | B1 | 2/2006 | Navarro et al. |
| 7,066,937 | B2 | 6/2006 | Shluzas |
| 7,087,057 | B2 | 8/2006 | Konieczynski et al. |
| 7,160,300 | B2 | 1/2007 | Jackson |
| 7,179,261 | B2 | 2/2007 | Sicvol et al. |
| 7,186,255 | B2 | 3/2007 | Baynham |
| 7,306,606 | B2 | 12/2007 | Sasing |
| 7,322,981 | B2 | 1/2008 | Jackson |
| 7,377,923 | B2 | 5/2008 | Purcell et al. |
| 7,491,218 | B2 | 2/2009 | Landry et al. |
| 7,530,992 | B2 | 5/2009 | Biedermann et al. |
| D601,702 | S | 10/2009 | Gotfried |
| 7,618,444 | B2 | 11/2009 | Shluzas |
| 7,625,396 | B2 | 12/2009 | Jackson |
| 7,686,835 | B2 | 3/2010 | Warnick |
| 7,766,945 | B2 | 8/2010 | Nilsson et al. |
| 7,776,067 | B2 | 8/2010 | Jackson |
| 7,833,251 | B1 | 11/2010 | Ahlgren et al. |
| 7,857,834 | B2 | 12/2010 | Boschert |
| 7,875,065 | B2 | 1/2011 | Jackson |
| 7,901,436 | B2 | 3/2011 | Baccelli |
| 7,922,748 | B2 | 4/2011 | Hoffman |
| 7,947,065 | B2 | 5/2011 | Hammill et al. |
| 8,021,397 | B2 | 9/2011 | Farris et al. |
| 8,034,089 | B2 | 10/2011 | Matthis et al. |
| 8,048,112 | B2 | 11/2011 | Suziki et al. |
| 8,048,126 | B2 | 11/2011 | Altarac et al. |
| 8,066,744 | B2 | 11/2011 | Justis et al. |
| 8,100,946 | B2 | 1/2012 | Strasbaugh et al. |
| 8,133,262 | B2 | 3/2012 | Whipple |
| 8,137,386 | B2 | 3/2012 | Jackson |
| 8,206,422 | B2 | 6/2012 | Hestad et al. |
| 8,277,485 | B2 | 10/2012 | Krishna et al. |
| 8,353,932 | B2 | 1/2013 | Jackson |
| 8,361,129 | B2 | 1/2013 | Chao |
| 8,377,102 | B2 | 2/2013 | Jackson |
| 8,430,914 | B2 | 4/2013 | Spratt et al. |
| 8,506,609 | B2 | 8/2013 | Biedermann et al. |
| 8,591,558 | B2 | 11/2013 | Matthis et al. |
| 8,814,913 | B2 | 8/2014 | Jackson |
| 8,876,869 | B1 | 11/2014 | Schafer et al. |
| 8,888,827 | B2 | 11/2014 | Harper et al. |
| 8,926,672 | B2 | 1/2015 | Jackson |
| 9,168,069 | B2 | 10/2015 | Jackson |
| 9,198,694 | B2 | 12/2015 | Mishra et al. |
| 9,393,047 | B2 | 7/2016 | Jackson et al. |
| 9,439,681 | B2 | 9/2016 | Keyer et al. |
| 9,456,853 | B2 | 10/2016 | Jackson |
| 9,480,517 | B2 | 11/2016 | Jackson et al. |
| 9,504,496 | B2 | 11/2016 | Jackson et al. |
| 9,717,534 | B2 | 8/2017 | Jackson et al. |
| 9,883,892 | B2 | 2/2018 | Jackson et al. |
| 9,907,574 | B2 | 3/2018 | Jackson et al. |
| 9,918,745 | B2 | 3/2018 | Jackson et al. |
| 9,956,006 | B2 | 5/2018 | Jackson |
| 9,980,753 | B2 | 5/2018 | Jackson et al. |
| 10,172,649 | B2 | 1/2019 | Jackson et al. |
| 10,179,010 | B2 | 1/2019 | Jackson et al. |
| 10,238,431 | B2 | 3/2019 | Jackson et al. |
| 10,278,738 | B2 | 5/2019 | Jackson et al. |
| 10,363,070 | B2 | 7/2019 | Jackson et al. |
| 10,398,475 | B2 | 9/2019 | Jackson et al. |
| 10,441,319 | B2 | 10/2019 | Jackson |
| 10,478,225 | B2 * | 11/2019 | Jackson .............. A61B 17/7037 |
| 10,765,455 | B2 | 9/2020 | Jackson et al. |
| 10,765,456 | B2 | 9/2020 | Jackson et al. |
| 10,813,671 | B2 | 10/2020 | Jackson et al. |
| 10,813,672 | B2 | 10/2020 | Jackson et al. |
| 10,856,909 | B2 | 12/2020 | Jackson et al. |
| 10,856,911 | B2 | 12/2020 | Jackson et al. |
| 10,918,420 | B2 | 2/2021 | Jackson et al. |
| 10,939,940 | B2 | 3/2021 | Jackson et al. |
| 10,945,768 | B2 | 3/2021 | Jackson et al. |
| 10,973,555 | B2 | 4/2021 | Jackson et al. |
| 10,987,137 | B2 * | 4/2021 | Jackson .............. A61B 17/7032 |
| 11,109,896 | B2 | 9/2021 | Jackson et al. |
| 11,116,548 | B2 | 9/2021 | Jackson et al. |
| 2002/0022842 | A1 | 2/2002 | Horvath et al. |
| 2002/0026193 | A1 | 2/2002 | Barker et al. |
| 2002/0133159 | A1 | 9/2002 | Jackson |
| 2002/0143341 | A1 | 10/2002 | Biedermann et al. |
| 2002/0193794 | A1 | 12/2002 | Taylor |
| 2004/0039383 | A1 | 2/2004 | Jackson |
| 2004/0049196 | A1 | 3/2004 | Jackson |
| 2004/0122425 | A1 | 6/2004 | Suzuki et al. |
| 2004/0167526 | A1 | 8/2004 | Jackson |
| 2004/0267264 | A1 | 12/2004 | Konieczynski et al. |
| 2005/0080415 | A1 | 4/2005 | Keyer et al. |
| 2005/0187548 | A1 | 8/2005 | Butler et al. |
| 2005/0228379 | A1 | 10/2005 | Jackson |
| 2005/0240180 | A1 | 10/2005 | Vienney |
| 2005/0261687 | A1 | 11/2005 | Garamszegi |
| 2006/0025771 | A1 | 2/2006 | Jackson |
| 2006/0036252 | A1 | 2/2006 | Baynham et al. |
| 2006/0058788 | A1 | 3/2006 | Hammer |
| 2006/0155277 | A1 | 7/2006 | Metz-Stavenhagen |
| 2006/0173454 | A1 | 8/2006 | Spitler et al. |
| 2006/0200131 | A1 | 9/2006 | Chao et al. |
| 2006/0217716 | A1 | 9/2006 | Baker |
| 2006/0276789 | A1 * | 12/2006 | Jackson .............. A61B 17/8605 606/916 |
| 2006/0293664 | A1 | 12/2006 | Schumacher |
| 2007/0088357 | A1 | 4/2007 | Johnson et al. |
| 2007/0090238 | A1 | 4/2007 | Justis |

(56) References Cited

U.S. PATENT DOCUMENTS

| | | | |
|---|---|---|---|
| 2007/0093817 A1* | 4/2007 | Barrus | A61B 17/7037 606/264 |
| 2007/0093826 A1 | 4/2007 | Hawkes et al. | |
| 2007/0093827 A1 | 4/2007 | Warnick | |
| 2007/0118117 A1 | 5/2007 | Altarac et al. | |
| 2007/0118123 A1 | 5/2007 | Strausbaugh et al. | |
| 2007/0123862 A1 | 5/2007 | Warnick | |
| 2007/0161999 A1 | 7/2007 | Biedermann et al. | |
| 2007/0233087 A1 | 10/2007 | Schlapfer | |
| 2007/0270813 A1 | 11/2007 | Garamszegi | |
| 2007/0270831 A1 | 11/2007 | Dewey et al. | |
| 2008/0045953 A1 | 2/2008 | Garamszegi | |
| 2008/0086132 A1 | 4/2008 | Biedermann et al. | |
| 2008/0132957 A1 | 6/2008 | Matthis et al. | |
| 2008/0140135 A1 | 6/2008 | Konieczynski et al. | |
| 2008/0140136 A1 | 6/2008 | Jackson | |
| 2008/0147129 A1 | 6/2008 | Biedermann et al. | |
| 2008/0154315 A1 | 6/2008 | Jackson | |
| 2008/0161863 A1 | 7/2008 | Arnold et al. | |
| 2008/0215100 A1 | 9/2008 | Matthis et al. | |
| 2008/0221681 A1 | 9/2008 | Trieu et al. | |
| 2008/0234761 A1 | 9/2008 | Jackson | |
| 2008/0269809 A1 | 10/2008 | Garamszegi | |
| 2008/0294202 A1 | 11/2008 | Peterson et al. | |
| 2008/0319490 A1 | 12/2008 | Jackson | |
| 2009/0012567 A1 | 1/2009 | Biedermann et al. | |
| 2009/0062865 A1 | 3/2009 | Schumacher | |
| 2009/0062866 A1 | 3/2009 | Jackson | |
| 2009/0062867 A1 | 3/2009 | Schumacher | |
| 2009/0069852 A1 | 3/2009 | Farris et al. | |
| 2009/0069853 A1 | 3/2009 | Schumacher | |
| 2009/0105769 A1 | 4/2009 | Rock et al. | |
| 2009/0105770 A1 | 4/2009 | Berrevoets et al. | |
| 2009/0204155 A1 | 8/2009 | Aschmann | |
| 2009/0240290 A1 | 9/2009 | Choi | |
| 2010/0004692 A1 | 1/2010 | Biedermann | |
| 2010/0023061 A1 | 1/2010 | Randol et al. | |
| 2010/0087865 A1 | 4/2010 | Biedermann et al. | |
| 2010/0094343 A1 | 4/2010 | Pham et al. | |
| 2010/0094349 A1 | 4/2010 | Hammer et al. | |
| 2010/0100137 A1 | 4/2010 | Justis et al. | |
| 2010/0114108 A1* | 5/2010 | Strauss | A61B 17/7032 606/102 |
| 2010/0152787 A1 | 6/2010 | Walsh et al. | |
| 2010/0198272 A1 | 8/2010 | Keyer et al. | |
| 2010/0204735 A1 | 8/2010 | Gephart et al. | |
| 2010/0234902 A1 | 9/2010 | Biedermann et al. | |
| 2010/0256686 A1 | 10/2010 | Fisher | |
| 2010/0262195 A1 | 10/2010 | Jackson | |
| 2010/0274288 A1 | 10/2010 | Prevost et al. | |
| 2010/0298891 A1 | 11/2010 | Jackson | |
| 2010/0305621 A1 | 12/2010 | Wang et al. | |
| 2011/0040338 A1 | 2/2011 | Jackson | |
| 2011/0046683 A1* | 2/2011 | Biedermann | A61B 17/7037 606/305 |
| 2011/0282399 A1 | 11/2011 | Jackson | |
| 2012/0010661 A1 | 1/2012 | Farris et al. | |
| 2012/0035670 A1 | 2/2012 | Jackson et al. | |
| 2012/0059426 A1 | 3/2012 | Jackson | |
| 2012/0143265 A1* | 6/2012 | Biedermann | A61B 17/7032 606/328 |
| 2012/0143266 A1 | 6/2012 | Jackson | |
| 2012/0179210 A1 | 7/2012 | Garamszegi | |
| 2012/0179212 A1 | 7/2012 | Jackson et al. | |
| 2012/0209336 A1 | 8/2012 | Jackson | |
| 2012/0245640 A1 | 9/2012 | Auerbach et al. | |
| 2012/0265257 A1 | 10/2012 | Jackson | |
| 2012/0303070 A1 | 11/2012 | Jackson | |
| 2012/0310290 A1 | 12/2012 | Jackson | |
| 2013/0023941 A1 | 1/2013 | Jackson | |
| 2013/0060292 A1 | 3/2013 | Jackson | |
| 2013/0072981 A1 | 3/2013 | Jackson | |
| 2013/0079830 A1 | 3/2013 | Garamszegi et al. | |
| 2013/0103098 A1 | 4/2013 | Jackson et al. | |
| 2013/0131730 A1 | 5/2013 | Jackson et al. | |
| 2013/0144346 A1 | 6/2013 | Jackson et al. | |
| 2013/0268006 A1 | 10/2013 | Garamszegi | |
| 2013/0345756 A1 | 12/2013 | Berrevoets et al. | |
| 2014/0058454 A1 | 2/2014 | Hammer | |
| 2014/0081334 A1 | 3/2014 | Jackson | |
| 2014/0128927 A1 | 5/2014 | Jackson | |
| 2014/0135854 A1 | 5/2014 | Dec et al. | |
| 2014/0163619 A1 | 6/2014 | Harvey | |
| 2014/0172018 A1 | 6/2014 | Gephart et al. | |
| 2014/0172023 A1 | 6/2014 | Garamszegi | |
| 2014/0379031 A1 | 12/2014 | Biedermann et al. | |
| 2016/0045228 A1 | 2/2016 | Biedermann et al. | |
| 2016/0220280 A1 | 8/2016 | Jackson | |
| 2016/0367293 A1 | 12/2016 | Keyer et al. | |
| 2017/0172627 A1 | 6/2017 | Kruger | |
| 2017/0265902 A1 | 9/2017 | Jackson | |
| 2017/0354443 A1 | 12/2017 | Jackson | |
| 2018/0000523 A1 | 1/2018 | Jackson | |
| 2018/0098795 A1 | 4/2018 | Jackson | |
| 2018/0360499 A9 | 12/2018 | Jackson | |
| 2019/0282278 A1 | 9/2019 | Schlapfer et al. | |
| 2021/0186571 A1 | 3/2021 | Jackson et al. | |
| 2021/0030446 A1 | 6/2021 | Jackson et al. | |
| 2021/0161565 A1 | 6/2021 | Jackson et al. | |
| 2021/0298792 A1 | 9/2021 | Jackson et al. | |

* cited by examiner

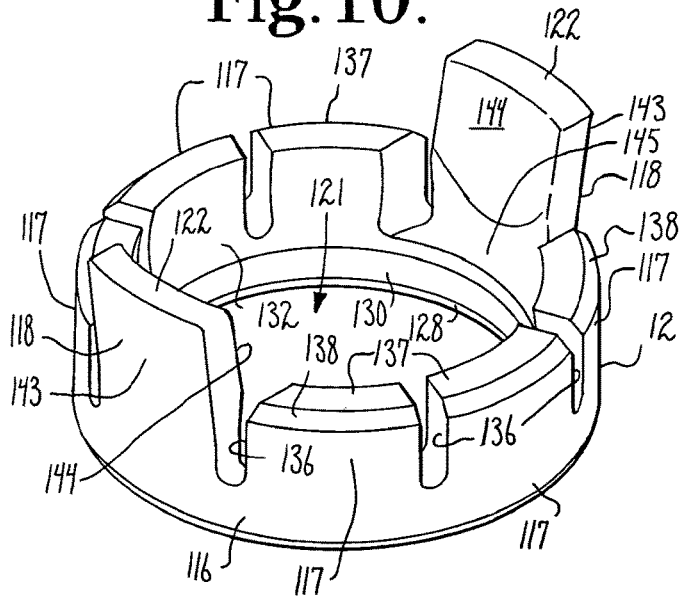
Fig. 10.
Fig. 12.
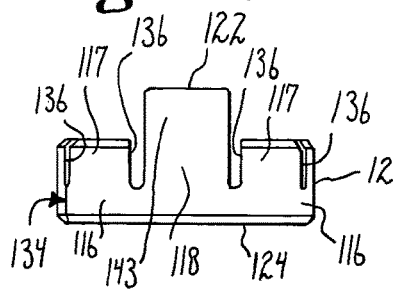
Fig. 11.
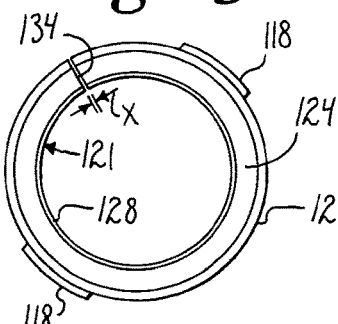
Fig. 13.
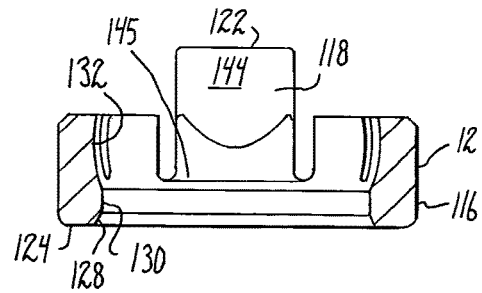
Fig. 14.
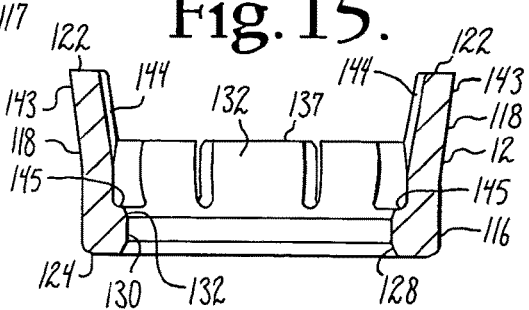
Fig. 15.

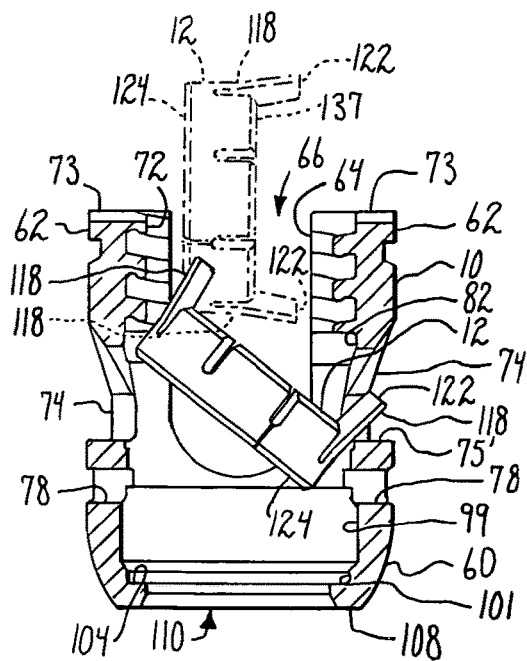
Fig.22.
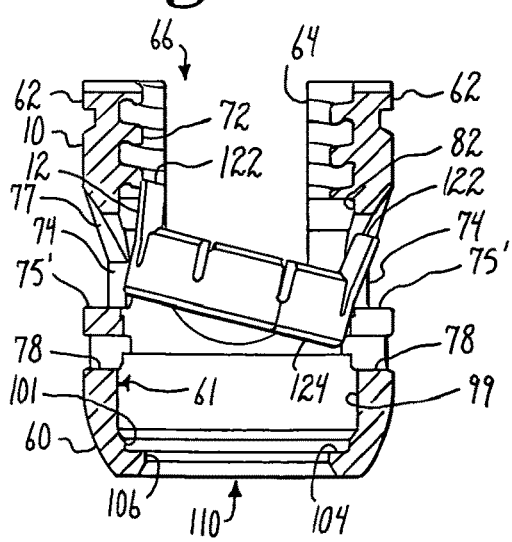
Fig.23.
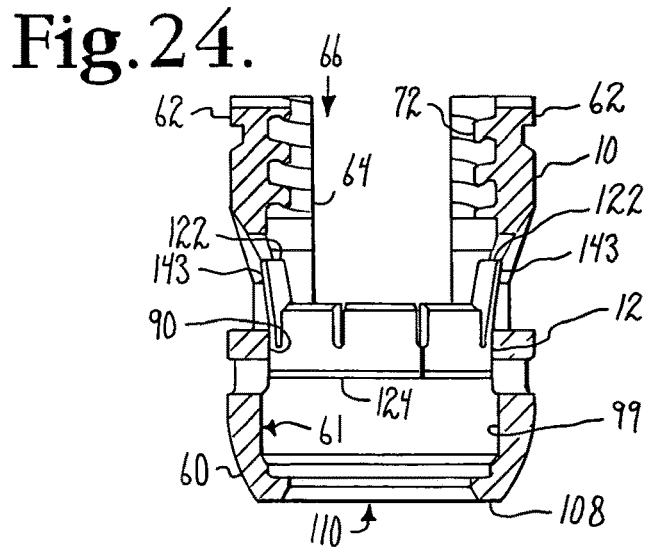
Fig.24.
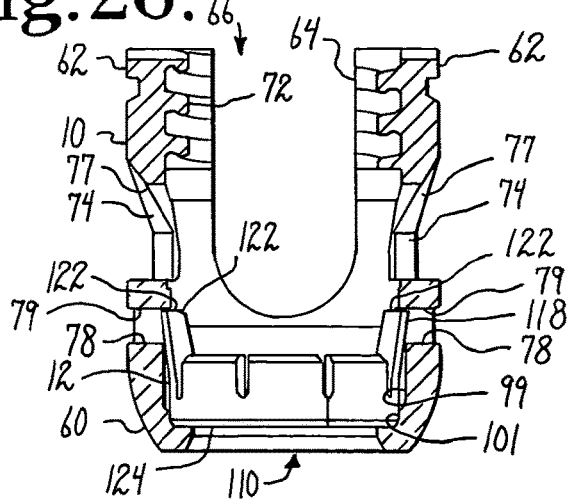
Fig.25.
Fig.26.

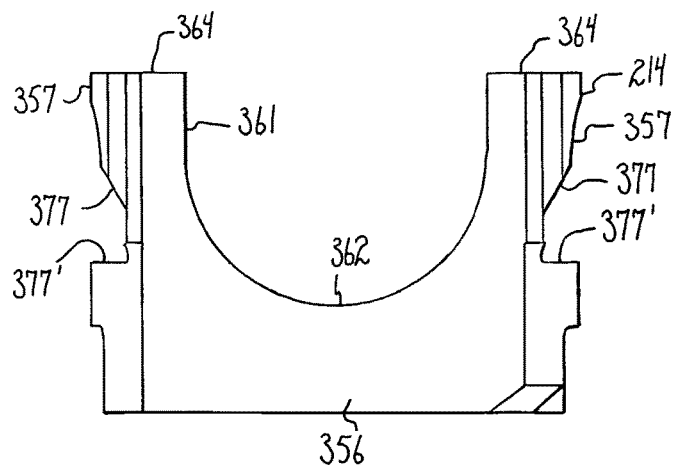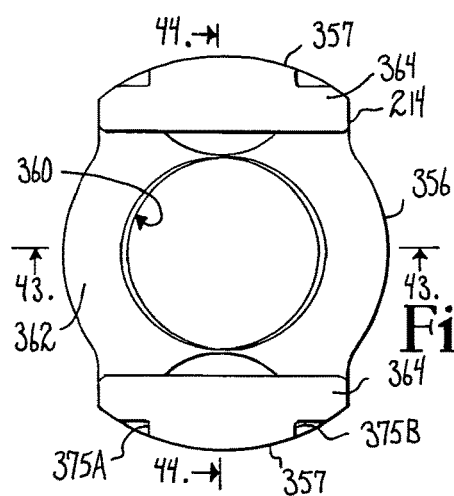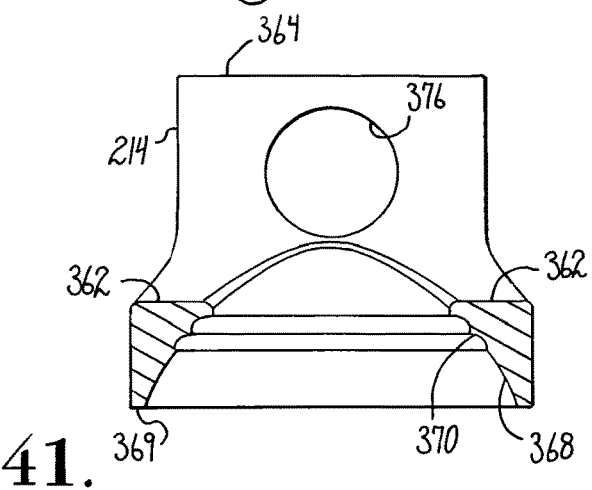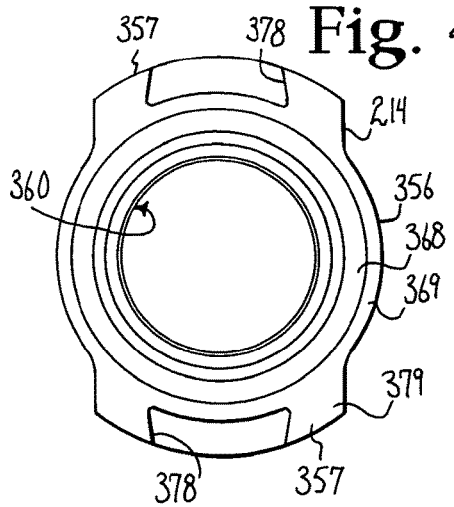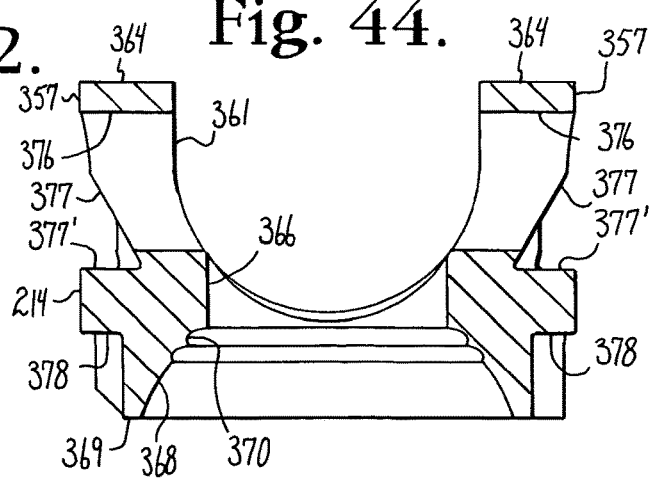

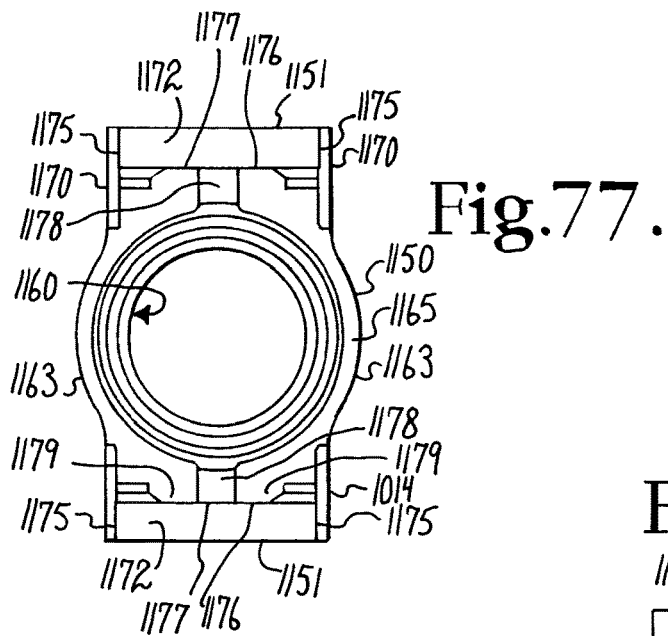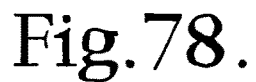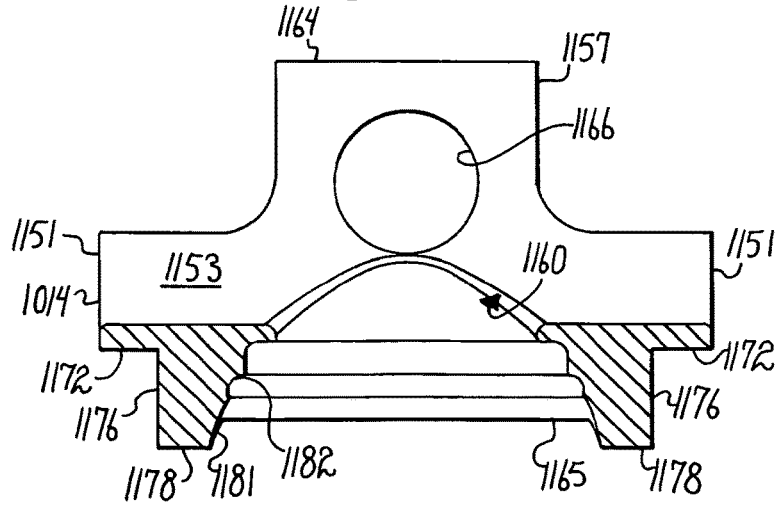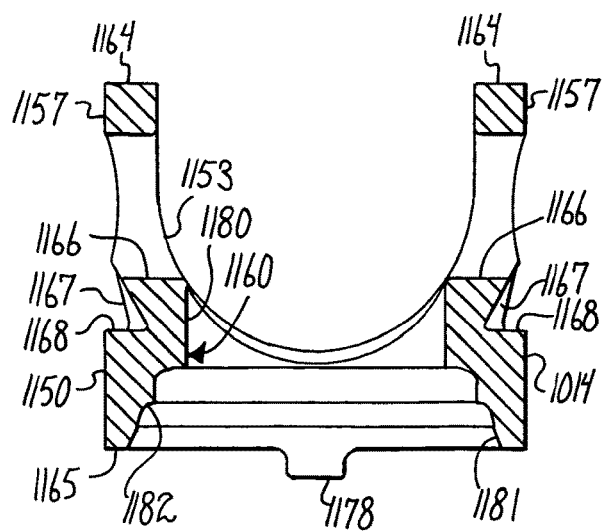

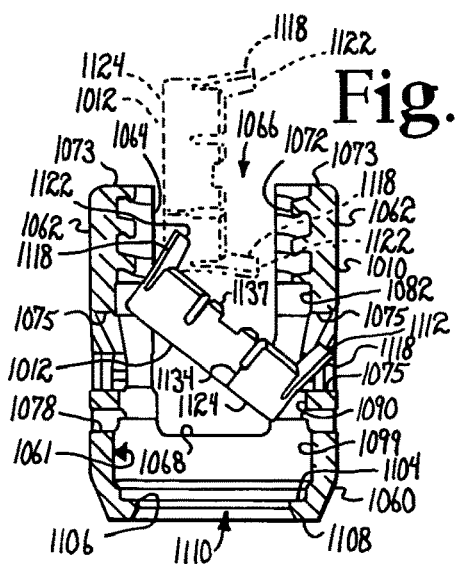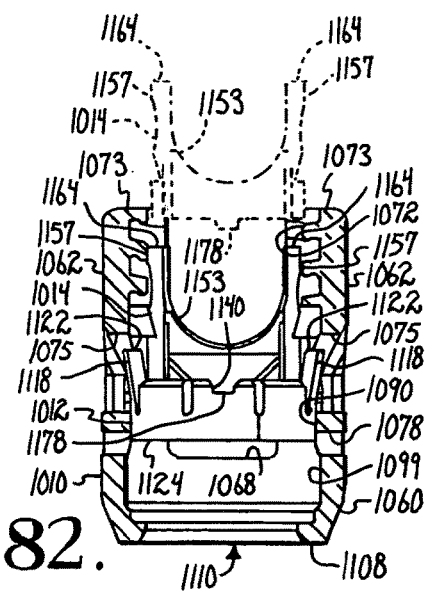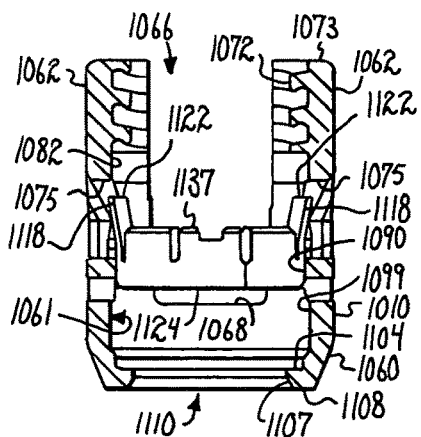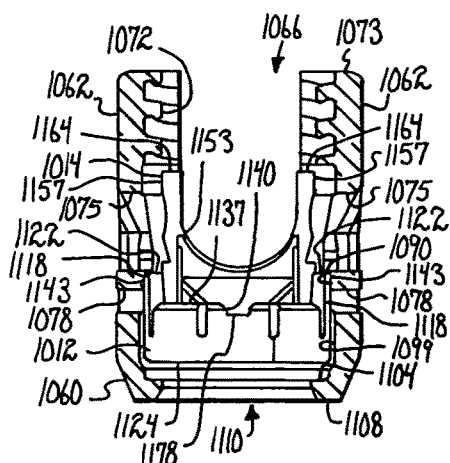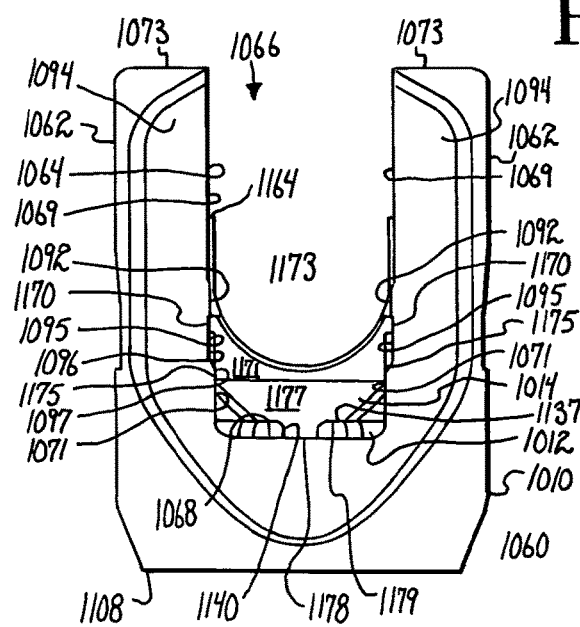

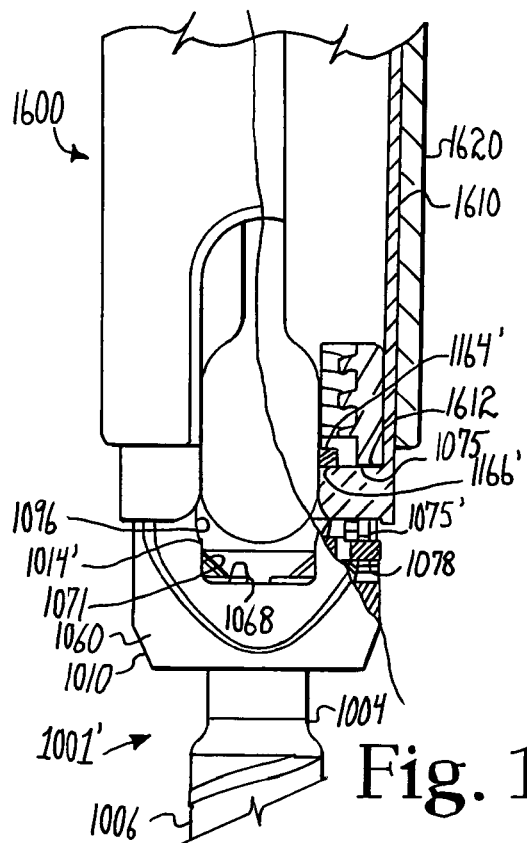
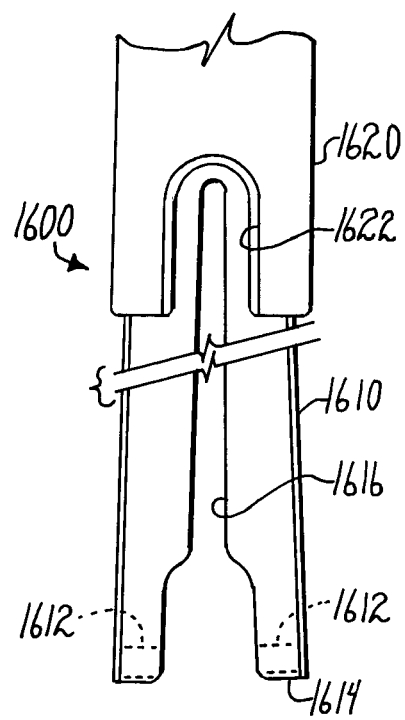
Fig. 101.  Fig. 102.
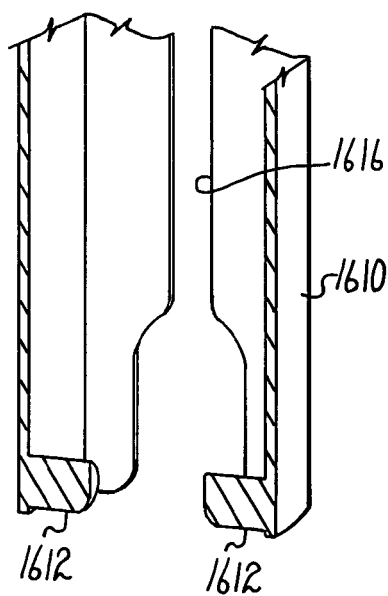
Fig. 103.

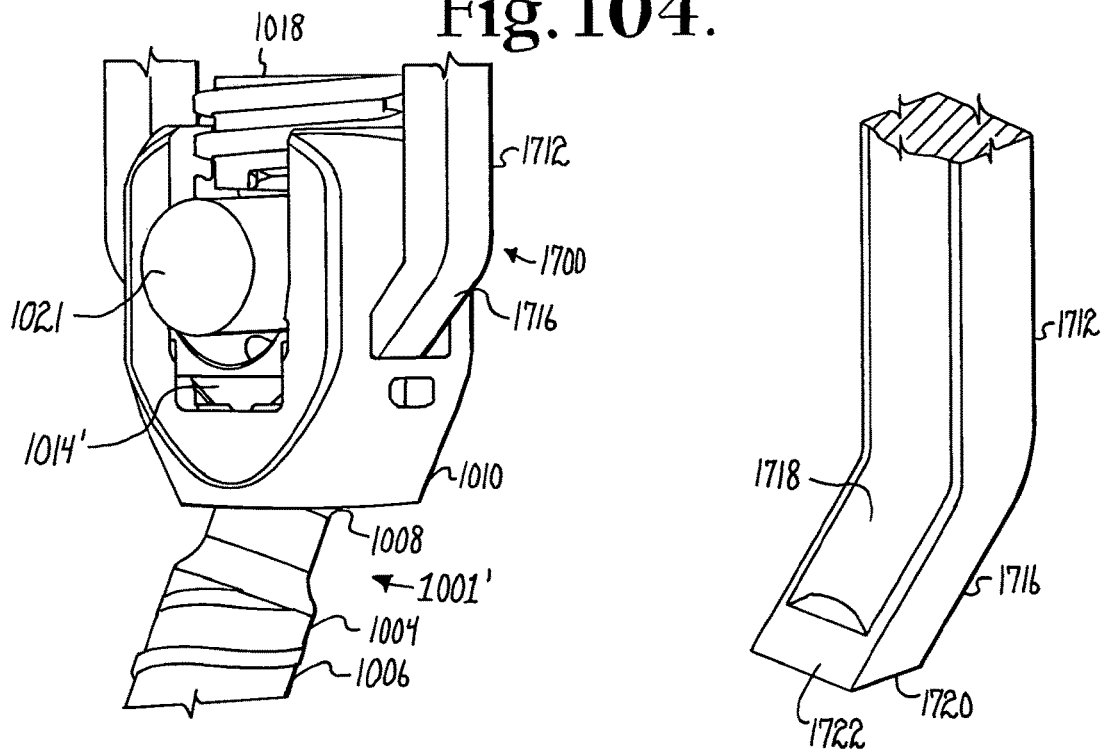
Fig.104.
Fig.105.
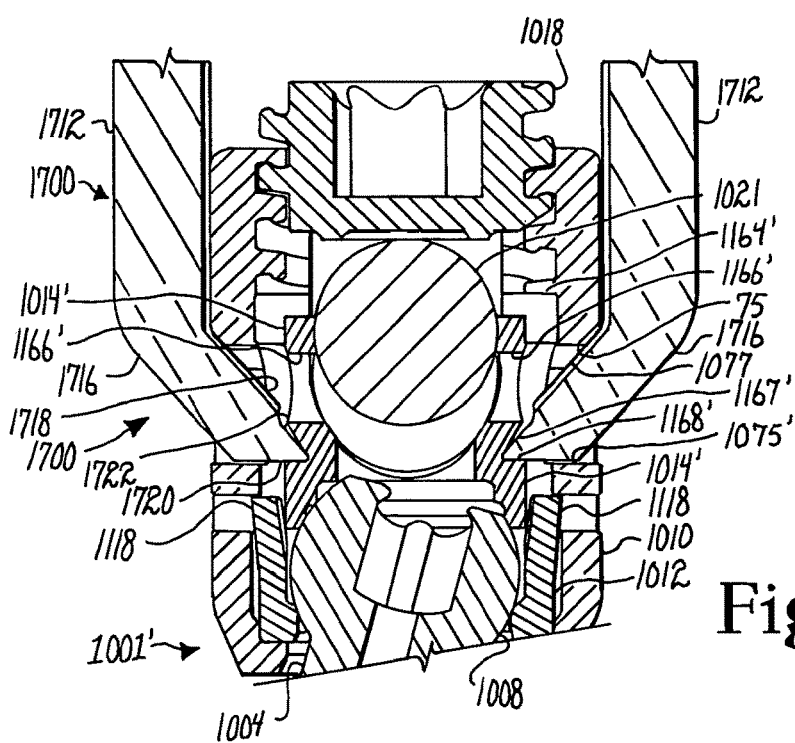
Fig.106.

PIVOTAL BONE ANCHOR ASSEMBLY WITH TOOL COMPRESSED INSERT FOR CLOSURE INDEPENDENT LOCKING

CROSS-REFERENCE TO RELATED APPLICATIONS

This application is a continuation of U.S. application Ser. No. 17/114,214 filed Dec. 7, 2020, which is a continuation of U.S. application Ser. No. 16/675,431 filed Nov. 6, 2019, now U.S. Pat. No. 10,856,909, which is a continuation of U.S. application Ser. No. 16/247,378 filed Jan. 14, 2019, now U.S. Pat. No. 10,478,225, which is a continuation of U.S. application Ser. No. 15/893,333 filed Feb. 9, 2018, now U.S. Pat. No. 10,179,010, which is a continuation of U.S. application Ser. No. 13/373,289, filed Nov. 9, 2011, now U.S. Pat. No. 9,907,574, which claims the benefit of U.S. Provisional Patent Application No. 61/460,234, filed Dec. 29, 2010, and U.S. Provisional Patent Application No. 61/456,649, filed Nov. 10, 2010, each of which is incorporated by reference in its entirety herein.

U.S. application Ser. No. 13/373,289 is also a continuation-in-part of U.S. application Ser. No. 12/924,802, filed Oct. 5, 2010, now U.S. Pat. No. 8,556,938, which claims the benefit of the following U.S. Provisional Patent Application Nos.: 61/278,240, filed Oct. 5, 2009; 61/336,911, filed Jan. 28, 2010; 61/343,737, filed May 3, 2010; 61/395,564, filed May 14, 2010; 61/395,752, filed May 17, 2010; 61/396,390, filed May 26, 2010; 61/398,807, filed Jul. 1, 2010; 61/400,504, filed Jul. 29, 2010; 61/402,959, filed Sep. 8, 2010; 61/403,696, filed Sep. 20, 2010; and 61/403,915, filed Sep. 23, 2010, each of which is incorporated by reference in its entirety herein.

U.S. application Ser. No. 13/373,289 is also a continuation-in-part of U.S. application Ser. No. 12/802,849 filed Jun. 15, 2010, now abandoned, which claims the benefit of the following U.S. Provisional Patent Application Nos.: 61/268,708, filed Jun. 15, 2009; 61/270,754, filed Jul. 13, 2009; 61/336,911, filed Jan. 28, 2010; 61/395,564, filed May 14, 2010; 61/395,752, filed May 17, 2010; and 61/396,390, filed May 26, 2010, each of which is incorporated by reference in its entirety herein.

BACKGROUND OF THE INVENTION

The present invention is directed to polyaxial bone screw shanks with heads for use in bone surgery, more specifically to spinal surgery and particularly to such screws with receiver member assemblies including compression or pressure inserts and expansion-only split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult. Also, it is often desirable to insert the bone screw shank separate from the receiver or head due to its bulk which can get in the way of what the surgeon needs to do. Such screws that allow for this capability are sometimes referred to as modular polyaxial screws.

With specific reference to modular snap-on or pop-on polyaxial pedicle screw systems having shank receiver assemblies, the prior art has shown and taught the concept of the receiver and certain retainer parts forming an assembly wherein a contractile locking engagement between the parts is created to fix the shank head with respect to the receiver and retainer. The receiver and shank head retainer assemblies in the prior art have included a contractile retainer ring and/or a lower pressure insert with an expansion and contraction collet-type of structure having contractile locking engagement for the shank head due to direct contact between the retainer and/or the collet structure with the receiver resulting in contraction of the retainer ring and/or the collet-type structure of the insert against the shank head.

The prior art for modular polyaxial screw assemblies has also shown and taught that the contact surfaces on the outside of the collect and/or retainer and the inside of the receiver can be tapered, conical, radiused, spherical, curvate, multi-curvate, rounded, as well as other configurations to create a contractile type of locking engagement for the shank head with respect to the receiver.

In addition, the prior art for modular polyaxial screw assemblies has shown and taught that the shank head can both enter and escape from a collet-like structure on the insert or from the retainer when the insert or retainer is in the up position and within the expansion recess or chamber of the receiver. This is the case unless the insert and/or the retainer are blocked from being able to be pushed back up into receiver bore or cavity.

SUMMARY OF THE INVENTION

The present invention differentiates from the prior art by not allowing the receiver to be removed from the shank head once the parts are snapped-on and connected. This is true even if the retainer can go back up into the expansion chamber. This approach or design has been found to be more secure and to provide more resistance to pull-out forces compared to the prior art for modular polyaxial screw designs. Collect-like structures extending downwardly from lower pressure inserts, when used in modular polyaxial screw designs, as shown in the prior art, have been found to be somewhat weak with respect to pull-out forces encountered during some spinal reduction procedures. The present invention is designed to solve these problems.

The present invention also differentiates from all of the prior art by providing a split retainer ring with a collet-like upper structure portion, wherein the collet-like structure does not participate at all in the locking engagement for the shank head with respect to the receiver. In addition, the retainer ring itself for the present invention is uniquely characterized by a base portion providing expansion to receive and capture the shank head and then having only expansion (not contraction) locking engagement between the shank head and the retainer ring base and between the retainer ring base and horizontal and vertical loading surfaces near a bottom opening of the receiver.

The expansion-only retainer ring base in the present invention is positioned entirely below the shank head hemisphere in the receiver and can be a stronger, more substantial structure to resist larger pull out forces on the assembly. The retainer ring base can also be better supported on a generally horizontal loading surface near the lower opening in the bottom of the receiver. This design has been found to be stronger and more secure when compared to that of the prior art which uses some type of contractile locking engagement between the parts, as described above; and, again, once assembled it cannot be disassembled.

Thus, a polyaxial bone screw assembly according to the invention includes a shank having an integral upper portion or integral spherical head and a body for fixation to a bone; a separate receiver defining an upper open channel, a central bore, a lower cavity and a lower opening; an insert that may be top drop and turn in place or may have extended portions that are received in the receiver channel; and a friction fit resilient expansion-only split retainer for capturing the shank head in the receiver lower cavity, the shank head being frictionally engaged with, but still movable in a non-floppy manner with respect to the friction fit retainer and the receiver prior to locking of the shank into a desired configuration. The compression insert operatively engages the shank head and is spaced from the retainer by the head that is snapped into the resilient retainer. The shank is finally locked into a fixed position relative to the receiver by frictional engagement between the insert and a lower split ring-like portion of the retainer, as described previously, due to a downward force placed on the compression insert by a closure top pressing on a rod, or other longitudinal connecting member, captured within the receiver bore and channel. In the illustrated embodiments, retainers and compression inserts are downloaded into the receiver, but uploaded embodiments are also foreseen. The shank head can be positioned into the receiver lower cavity at the lower opening thereof prior to or after insertion of the shank into bone. Some compression inserts include a lock and release feature for independent locking of the polyaxial mechanism so the screw can be used like a fixed monoaxial screw. The shank can be cannulated for minimally invasive surgery applications. The receiver can have crimp tabs, but is devoid of any type of spring tabs or collet-like structures. The lower pressure insert and/or the retainer are both devoid of any type of receiver-retainer contractile locking engagements with respect to the shank head. The retainer can also have upwardly extending spring tabs which are deployed into openings in the receiver cavity so that the retainer and captured shank head are stabilized and fully constrained in the region of the receiver locking chamber once they enter into this lower portion of the receiver cavity. In this way, the shank head and retainer cannot go back up into the receiver cavity.

Again, a pre-assembled receiver, compression insert and friction fit split retainer may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the base portion of the split retainer ring and expanding the resilient lower open retainer portion out into an expansion portion or chamber of the receiver cavity followed by an elastic return of the retainer back to an original or nominal shape thereof after the hemisphere of the shank head or upper portion passes through the lower ring-like portion of the retainer. The shank head also enters into the friction fit upper portion of the retainer, the panels of the friction fit portion of the retainer snapping onto the shank head as the retainer returns to a neutral or close to neutral orientation, providing a non-floppy connection between the retainer and the shank head. The friction fit between the shank head and the retainer is temporary and not part of the final locking mechanism. In the illustrated embodiments, when the shank is ultimately locked between the compression insert and the lower portion of the retainer, the friction fit collet-like panels of the retainer are no longer in a friction fit engagement with the shank head and they are not in contact with the receiver. The final fixation occurs as a result of a locking expansion-type of contact between the shank head and the lower portion of the split retainer and an expansion-type of non-tapered locking engagement between the lower portion of the retainer ring and the locking chamber in the lower portion of the receiver cavity. The retainer can expand more in the upper portion or expansion chamber of the receiver cavity to allow the shank head to pass through, but has restricted expansion to retain the shank head when the retainer lower ring portion is against the locking chamber surfaces in the lower portion of the receiver cavity and the shank head is forced down against the retainer ring during final locking. In some embodiments, when the polyaxial mechanism is locked, the insert is forced or wedged against a surface of the receiver resulting in an interference locking engagement, allowing for adjustment or removal of the rod or other connecting member without loss of a desired angular relationship between the shank and the receiver. This independent locking feature allows the polyaxial screw to function like a fixed monoaxial screw.

The lower pressure insert may also be configured to be independently locked by a tool or instrument, thereby allowing the pop-on polyaxial screw to be distracted, compressed and/or rotated along and around the rod to provide for improved spinal correction techniques. Such a tool engages the pop-on receiver from the sides and then engages the insert to force the insert down into a locked position within the receiver. In the illustrated embodiments, both the receiver and the insert include apertures having tool receiving surfaces that are disposed at an oblique angle with respect to a central axis of the receiver. Such sloping surfaces of the receiver and the insert align and provide a path for such a locking tool to be inserted through the receiver at arm surfaces thereof and against the insert in a downwardly directed angle towards the head of the shank.

With the locking tool still in place and a desired correction maintained, the rod is then locked within the receiver channel by a closure top followed by removal of the tool. This process may involve multiple screws all being manipulated simultaneously with multiple tools to achieve the desired correction.

It is noted that once the shank head is captured by the retainer ring and the retainer and head are moved down into the locking chamber region of the receiver cavity, retainer spring tabs are deployed outwardly stabilizing the retainer so that the retainer cannot go back up into the receiver cavity. This spring tab deployment also creates good rotational stability between the retainer and receiver and provides for an additional rotational friction fit between the shank head and the receiver itself since the retainer cannot axially rotate in the receiver.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 10 is an enlarged perspective view of the retainer of FIG. 1.

FIG. 11 is a reduced side elevational view of the retainer of FIG. 10.

FIG. 12 is a top plan view of the retainer of FIG. 10.

FIG. 13 is a reduced bottom plan view of the retainer of FIG. 10.

FIG. 14 is a reduced cross-sectional view taken along the line 14-14 of FIG. 12.

FIG. 15 is a reduced cross-sectional view taken along the line 15-15 of FIG. 12.

FIG. 22 is an enlarged front elevational view of the retainer and receiver of FIG. 1 with portions of the receiver broken away to show the detail thereof, the retainer being shown downloaded into the receiver (in phantom) to a partially inserted stage of assembly.

FIG. 23 is a front elevational view of the retainer and receiver with portions broken away, similar to what is shown in FIG. 22, showing the retainer in a subsequent stage of assembly.

FIG. 24 is a front elevational view of the retainer and receiver with portions broken away, similar to what is shown in FIG. 23, showing the retainer in a subsequent stage of assembly.

FIG. 25 is a front elevational view of the retainer and receiver with portions broken away, similar to what is shown in FIG. 24, showing the retainer in a subsequent stage of assembly.

FIG. 26 is a front elevational view of the retainer and receiver with portions broken away, similar to what is shown in FIG. 25, showing the retainer in a subsequent stage of assembly.

FIG. 40 is a front elevational view of the insert of FIG. 38.

FIG. 41 is a top plan view of the insert of FIG. 38.

FIG. 42 is a bottom plan view of the insert of FIG. 38.

FIG. 43 is a cross-sectional view taken along the line 43-43 of FIG. 41.

FIG. 44 is a cross-sectional view taken along the line 44-44 of FIG. 41.

FIG. 77 is a bottom plan view of the insert of FIG. 74.

FIG. 78 is an enlarged cross-sectional view taken along the line 78-78 of FIG. 76.

FIG. 79 is an enlarged cross-sectional view taken along the line 79-79 of FIG. 76.

FIG. 80 is an enlarged front elevational view of the retainer and receiver of FIG. 59 with portions of the receiver broken away to show the detail thereof, the retainer being shown downloaded into the receiver (in phantom) to a partially inserted stage of assembly.

FIG. 81 is a front elevational view of the retainer and receiver with portions broken away, similar to what is shown in FIG. 80, showing the retainer in a subsequent stage of assembly.

FIG. 82 is a front elevational view of the retainer and receiver with portions broken away, similar to what is shown in FIG. 81, also showing the insert being downloaded into the receiver (in phantom) to a partially inserted stage of assembly.

FIG. 83 is a front elevational view of the retainer, receiver and insert with portions broken away, similar to what is shown in FIG. 82, showing the retainer and insert in a subsequent stage of assembly, the retainer spring tabs being pressed inwardly and the insert being captured by the receiver.

FIG. 84 is an enlarged front elevational view of the assembly as shown in FIG. 83 showing the capture of the insert by opposed projections of the receiver.

FIG. 101 is a reduced and partial front elevational view with portions broken away of the assembly of FIG. 100 without the alternative rod and closure top, and further showing unlocking of the insert from the receiver with a two-piece tool having an inner insert engaging portion and an outer tubular holding portion.

FIG. 102 is a reduced and partial front elevational view of the two-piece tool of FIG. 101, holding prongs of the inner insert engaging portion being shown in phantom.

FIG. 103 is an enlarged and partial front elevational view of the inner insert engaging portion of the tool shown in FIG. 102 with portions broken away to show the detail thereof.

FIG. 104 is an enlarged and partial perspective view of the assembly of FIG. 97, but shown with the shank being at an angle with respect to the receiver and further showing an alternative locking tool for independently locking the insert into an interference fit with the receiver and thus locking the shank with respect to the receiver even when the closure top and rod are in a loose, unlocked relationship with the receiver as shown.

FIG. 105 is an enlarged and partial perspective view of a portion of the locking tool of FIG. 104.

FIG. 106 is an enlarged and partial front elevational view of the assembly and locking tool of FIG. 104 with portions broken away to show the detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
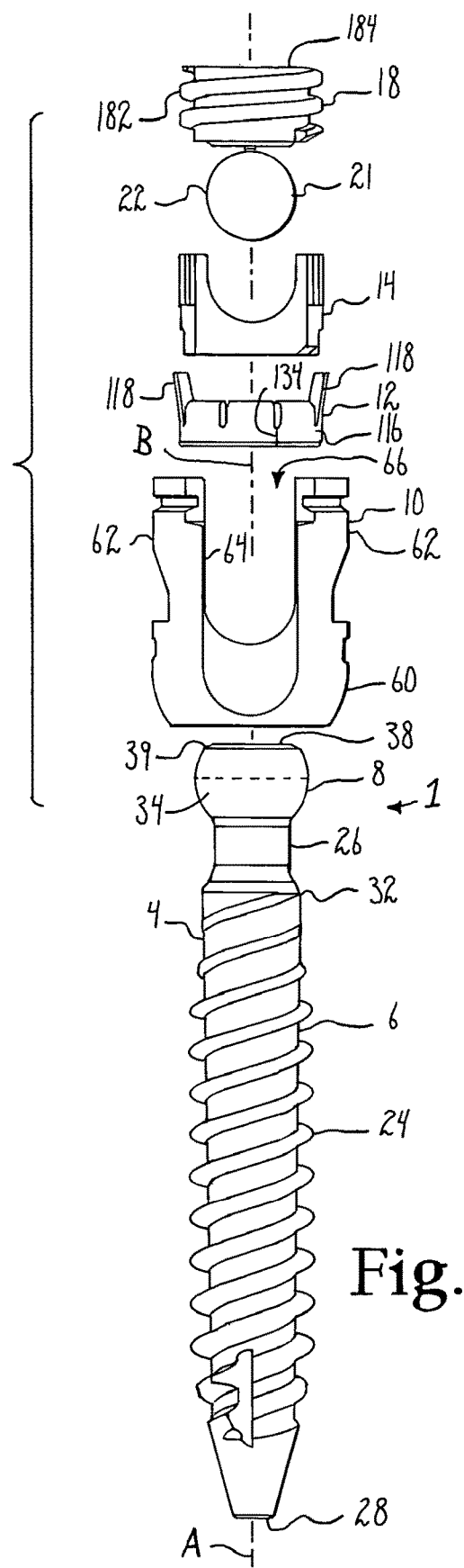
FIG. 1 is an exploded front elevational view of a polyaxial bone screw assembly according to the present invention including a shank, a receiver, an open friction fit expansion-only retainer and a top drop and turn in place lower compression insert, further shown with a portion of a longitudinal connecting member in the form of a rod and a closure top.
Figure 36:
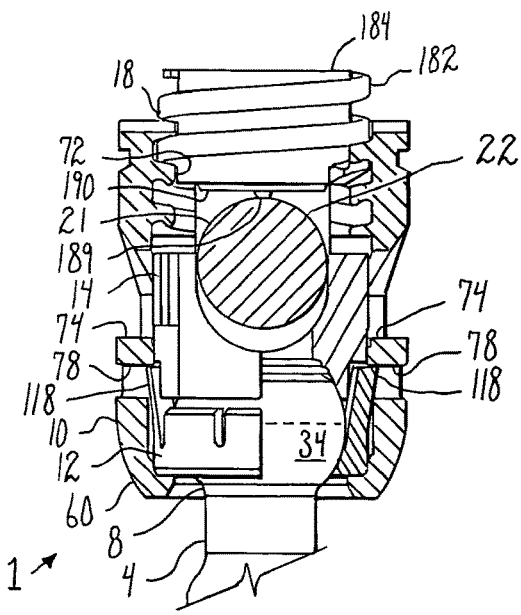
FIG. 36 is an enlarged and partial front elevational view with portions broken away of all of the components shown in FIG. 1, the assembly of FIG. 35 shown in a stage of assembly with the rod and closure top.
Figure 37:
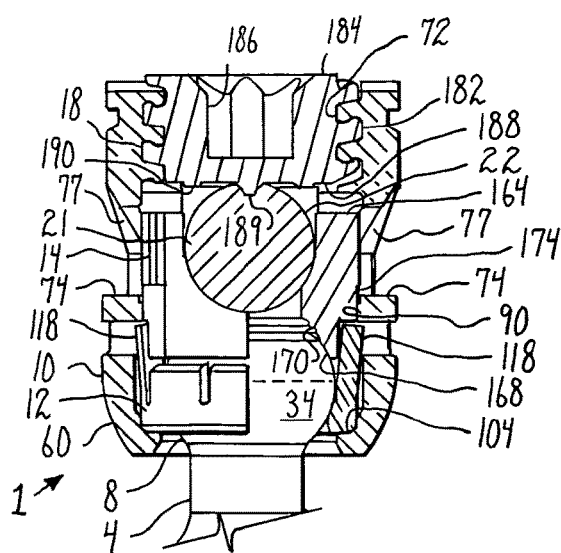
FIG. 37 is a partial front elevational view with portions broken away, similar to FIG. 36, shown in a final locking position.
Figure 38:
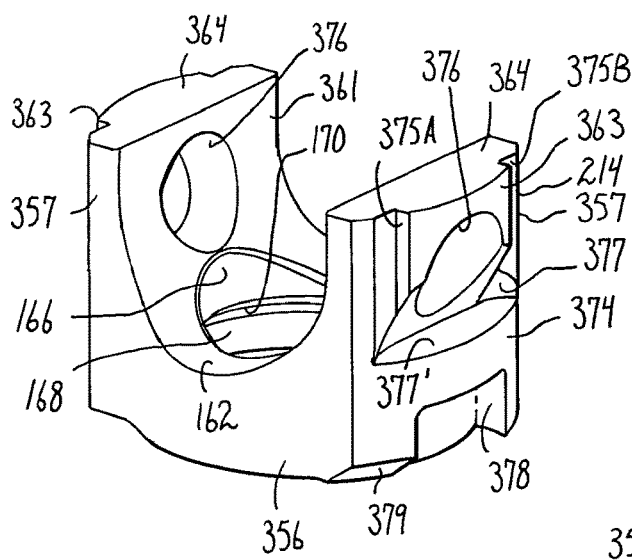
FIG. 38 is an enlarged perspective view of an alternative locking insert for use with the assembly of FIG. 1 in lieu of the insert shown in FIG. 1.
Figure 39:
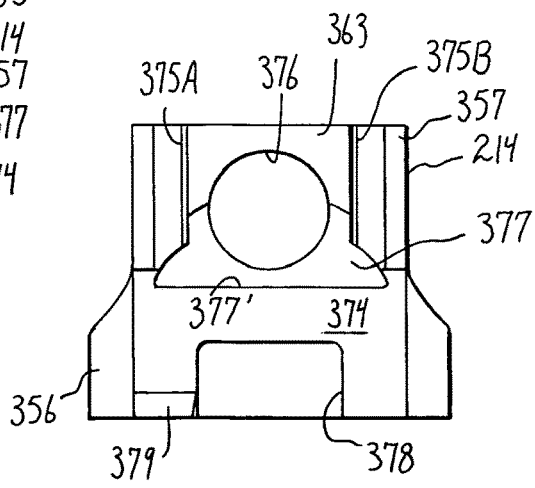
FIG. 39 is a side elevational view of the insert of FIG. 38.
Figure 45:
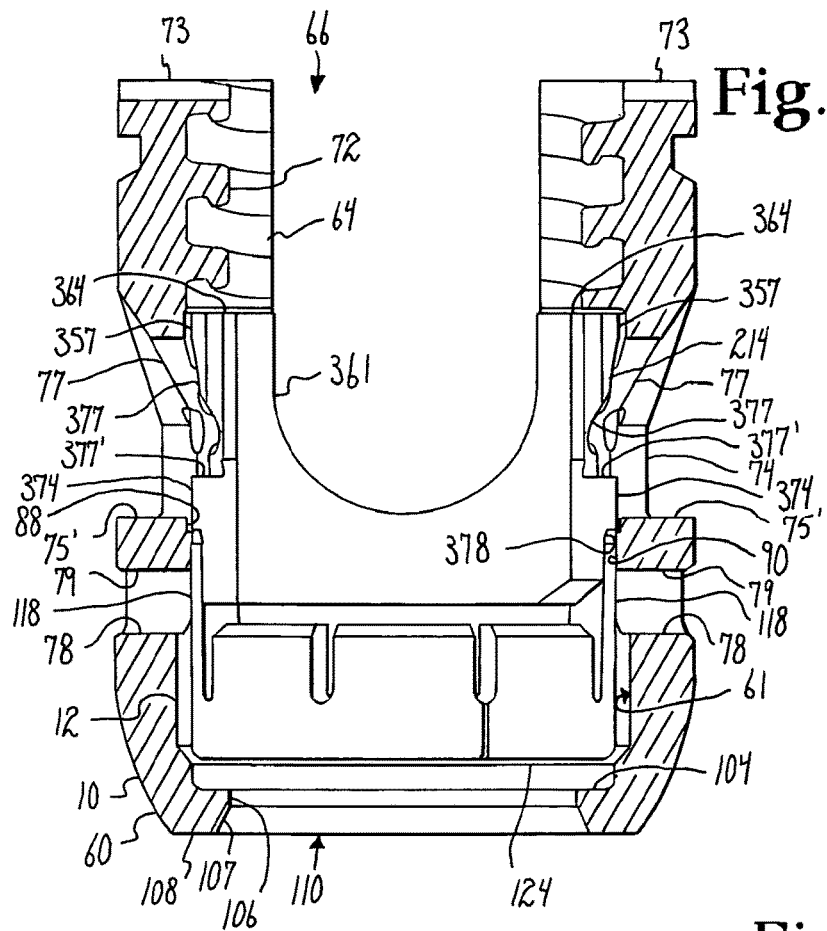
FIG. 45 is an enlarged and partial front elevational view with portions broken away of the receiver and retainer of FIG. 1 and the insert of FIG. 38, shown in an un-locked shipping position.
Figure 46:
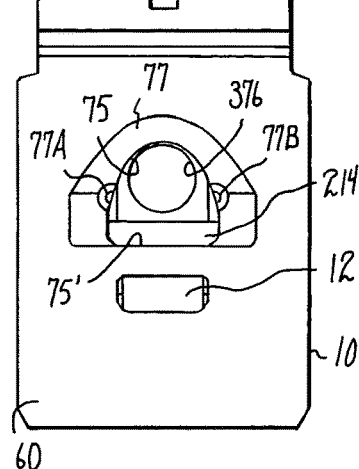
FIG. 46 is a reduced side elevational view of the assembly of FIG. 45 further showing the receiver crimped to the insert.

With reference to FIGS. 1-37 the reference number 1 generally represents a polyaxial bone screw apparatus or assembly according to the present invention. The assembly 1 includes a shank 4, that further includes a body 6 integral with an upwardly extending upper portion or head structure 8; a receiver 10; a friction fit retainer 12, and a crown-like compression or pressure insert 14. The receiver 10, retainer 12 and compression insert 14 are initially assembled and may be further assembled with the shank 4 either prior or subsequent to implantation of the shank body 6 into a vertebra 17, as will be described in greater detail below. FIGS. 1 and 36-37 further show a closure structure 18 for capturing a longitudinal connecting member, for example, a rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 17. The illustrated rod 21 is hard, stiff, non-elastic and cylindrical, having an outer cylindrical surface 22. It is foreseen that in other embodiments, the rod 21 may be elastic, deformable and/or of different materials and cross-sectional geometries. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

Figure 2:
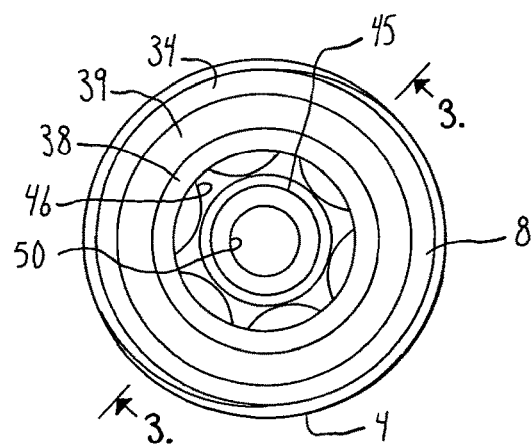
FIG. 2 is an enlarged top plan view of the shank of FIG. 1.
Figure 3:
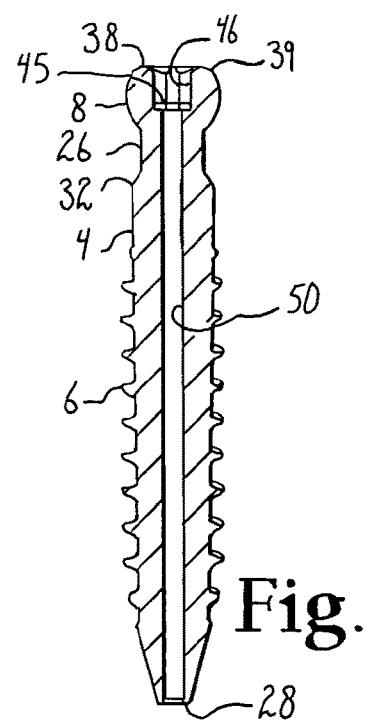
FIG. 3 is reduced cross-sectional view taken along the line 3-3 of FIG. 2.
Figure 4:
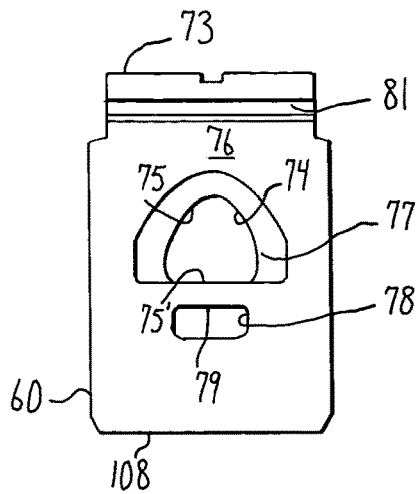
FIG. 4 is an enlarged side elevational view of the receiver of FIG. 1.
Figure 5:
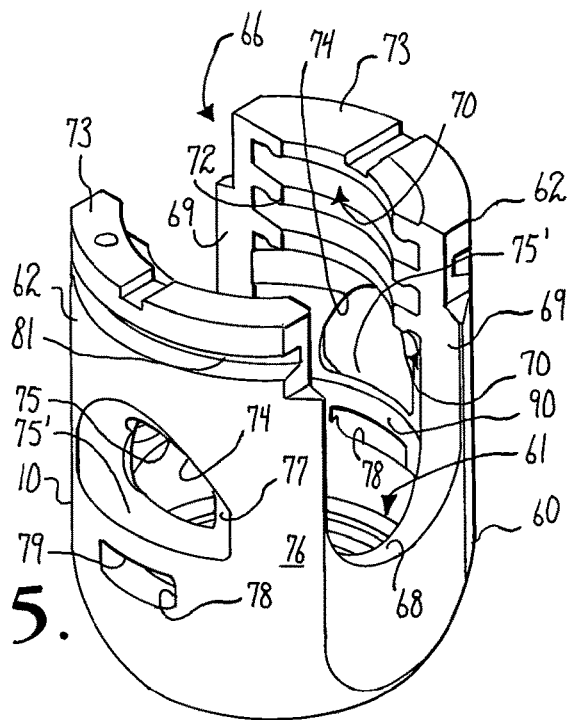
FIG. 5 is an enlarged perspective view of the receiver of FIG. 4.
Figure 6:
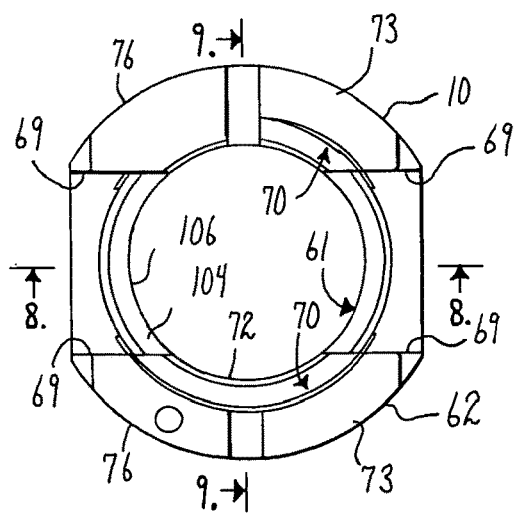
FIG. 6 is an enlarged top plan view of the receiver of FIG. 4.
Figure 7:
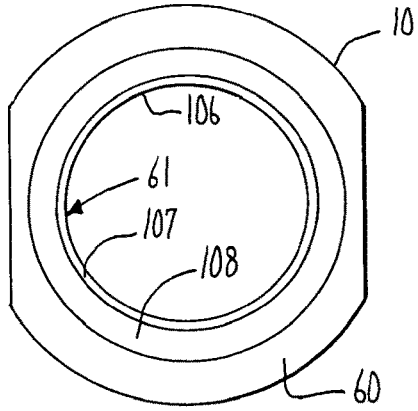
FIG. 7 is an enlarged bottom plan view of the receiver of FIG. 4.
Figure 8:
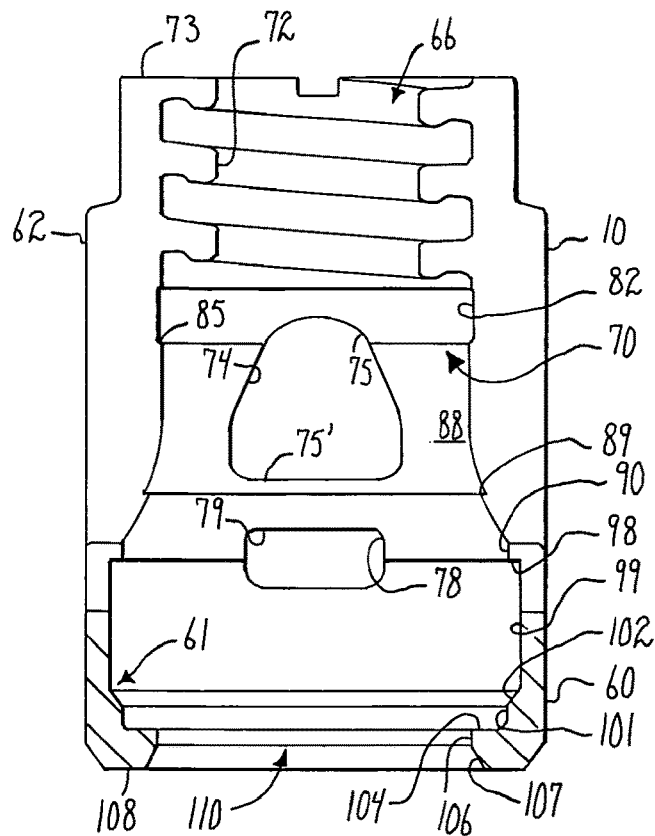
FIG. 8 is an enlarged cross-sectional view taken along the line 8-8 of FIG. 6.
Figure 9:
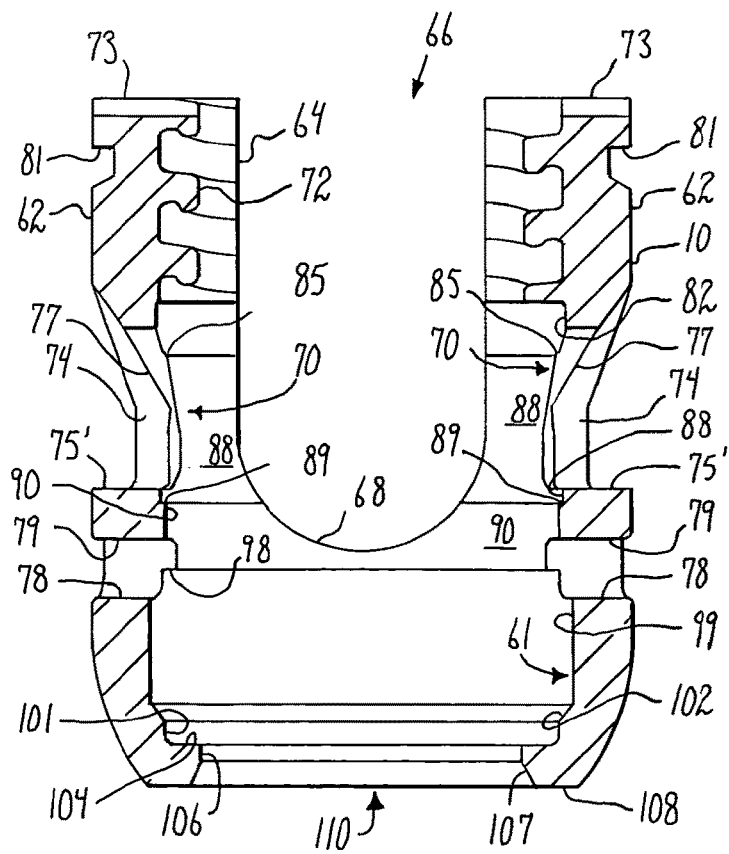
FIG. 9 is an enlarged cross-sectional view taken along the line 9-9 of FIG. 6.
Figure 16:
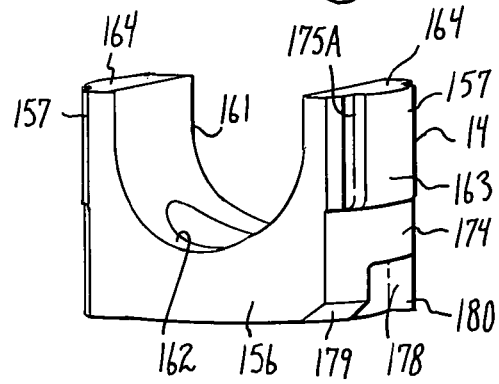
FIG. 16 is an enlarged perspective view of the insert of FIG. 1.
Figure 17:
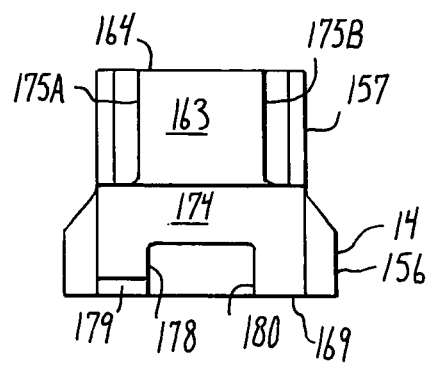
FIG. 17 is a side elevational view of the insert of FIG. 16.
Figure 18:
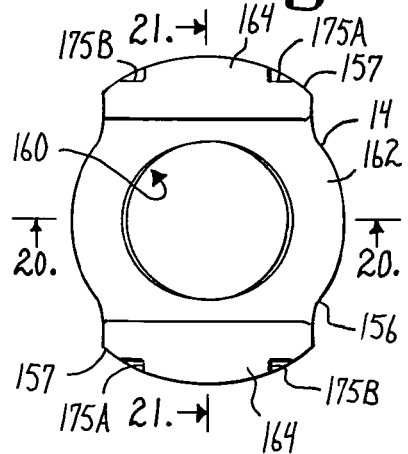
FIG. 18 is a top plan view of the insert of FIG. 16.
Figure 20:
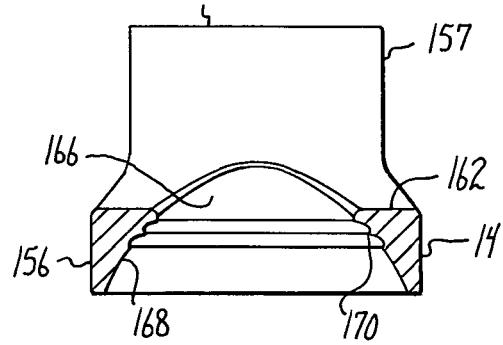
FIG. 20 is an enlarged cross-sectional view taken along the line 20-20 of FIG. 18.
Figure 19:
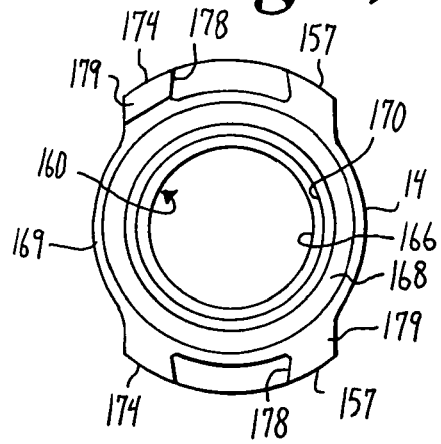
FIG. 19 is a bottom plan view of the insert of FIG. 16.
Figure 21:
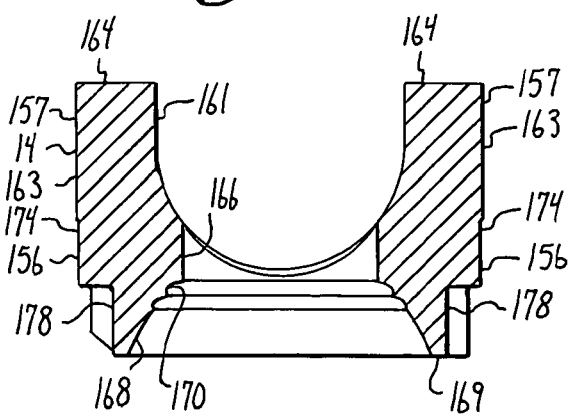
FIG. 21 is an enlarged cross-sectional view taken along the line 21-21 of FIG. 18.

The shank 4, best illustrated in FIGS. 1-3, is elongate, with the shank body 6 having a helically wound bone implantable thread 24 (single or dual lead thread form and different thread types) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 leading with the tip 28 and driven down into the vertebra with an installation or driving tool (not shown), so as to be implanted in the vertebra to a location at or near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 that in some embodiments terminates at a substantially planar top or rim surface 38. In the illustrated embodiment, a frusto-conical surface 39 extends from the spherical surface 34 to the top surface 38, providing additional clearance during pivoting of the shank with respect to the receiver 10 and the insert 14. The spherical surface 34 has an outer radius configured for temporary frictional, non-floppy, sliding cooperation with panels of the retainer 12 having concave or flat surfaces, as well as ultimate frictional engagement with the insert 14 at an inner partially spherical surface thereof, as will be discussed more fully in the paragraphs below. The top surface 38 is substantially perpendicular to the axis A. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with a lower ring-like portion of the retainer 12. The shank spherical surface 34 is locked into place exclusively by the insert 14 and the retainer 12 lower portion and not by inner surfaces defining the receiver cavity.

A counter sunk substantially planar base or stepped seating surface 45 partially defines an internal drive feature or imprint 46. The illustrated internal drive feature 46 is an aperture formed in the top surface 38 and has a star shape designed to receive a tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or hex-shaped aperture. The seat or base surfaces 45 of the drive feature 46 are disposed substantially perpendicular to the axis A with the drive feature 46 otherwise being coaxial with the axis A. As illustrated in FIGS. 2 and 3, the drive seat 45 may include beveled or stepped surfaces that may further enhance gripping with the driving tool. In operation, a driving tool (not shown) is received in the internal drive feature 46, being seated at the base 45 and engaging the faces of the drive feature 46 for both driving and rotating the shank body 6 into the vertebra 17, either before the shank 4 is attached to the receiver 10 or after the shank 4 is attached to the receiver 10, with the shank body 6 being driven into the vertebra 17 with the driving tool extending into the receiver 10.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper opening communicating with the external drive 46 at the driving seat 45. The bore 50 is coaxial with the threaded body 6 and the upper portion 8. The bore 50 provides a passage through the shank 4 interior for a length of wire (not shown) inserted into the vertebra 17 prior to the insertion of the shank body 6, the wire providing a guide for insertion of the shank body 6 into the vertebra 17. It is foreseen that the shank could be solid and made of different materials, including metal and non-metals.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-9, the receiver 10 has a generally U-shaped appearance with partially discontinuous and partially cylindrical inner and outer profiles. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A, as shown, for example, in FIG. 54.

The receiver 10 includes a substantially cylindrical base 60 defining a bore or inner cavity, generally 61, the base 60 being integral with a pair of opposed upstanding arms 62 forming a cradle and defining a channel 64 between the arms 62 with an upper opening, generally 66, and a U-shaped lower channel portion or seat 68, the channel 64 having a width for operably snugly receiving the rod 21 or portion of another longitudinal connector between the arms 62, the channel 64 communicating with the base cavity 61. Inner opposed substantially planar arm surfaces 69 partially define the channel 64 directly above the seat 68 and are located on either side of each arm interior surface generally 70, that includes various inner cylindrical profiles, an upper one of which is a partial helically wound guide and advancement structure 72 located adjacent top surfaces 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms 62 could have break-off extensions.

An opposed pair of upper rounded off triangular or delta-shaped tool receiving and engaging apertures 74, each having a through bore formed by an upper arched surface 75 and a substantially planar bottom surface 75', are formed on outer surfaces 76 of the arms 62. Each through bore surface 75 and 75' extends through the arm inner surface 70. The apertures 74 with through bore portions 75 and 75' are sized and shaped for receiving portions of the retainer 12 during top loading of the retainer from the receiver opening 66 and into the base cavity 61 as shown, for example, in FIGS. 22-24 and as will be described in greater detail below. Each apertures 74 further includes a sloping tool alignment surface 77 that surrounds the arched bore portion 75 and does not extend completely through the respective arm 62. Thin edge portions 77A and 77B of the sloping surface 77 also function as a crimp wall that is pressed or crimped into the insert 14 to prohibit rotation and misalignment of the insert 14 with respect to the receiver 10 as will be described in greater detail below. In other embodiments of the invention, other surfaces forming the aperture 74 may be inwardly crimped. The receiver 10 is an integral structure and devoid of any spring tabs or collet-like structures. Preferably the insert and/or receiver are configured with structure for blocking rotation of the insert with respect to the receiver, such as the sloping crimp wall 77, but allowing some up and down movement of the insert with respect to the receiver during the assembly and implant procedure. Two additional rectangular shaped through bores 78 are also formed in the arms 62 and are located directly below the apertures 74. It is foreseen that the opening 78 could assume almost any shape. The through bores 78 are sized and shaped for receiving spring tab portions of the retainer 12 during assembly and final operation and which capture and retain the retainer 12 within the receiver as shown, for example, in FIG. 26. An upper surface 79 defining each bore 78 functions as an upper stop for a portion of the retainer 12, during shipping and during assembly as will be described in greater detail below. Also formed in each outer arm surface 76 near the top surface 73 is an undercut tool receiving and engaging groove 81. Some or all of the apertures 74 and 78 and the groove 81 may be used for holding the receiver 10 during assembly with the insert 14, the retainer 12 and the shank 4; during the implantation of the shank body 6 into a vertebra when the shank is pre-assembled with the receiver 10; during assembly of the bone anchor assembly 1 with the rod 21 and the closure structure 18; and during lock and release adjustment of some inserts according to the invention with respect to the receiver 10, either into or out of frictional engagement with the inner surfaces of the receiver 10 as will be described in greater detail below. It is foreseen that tool receiving grooves or apertures may be configured in a variety of shapes and sizes and be disposed at other locations on the receiver arms 62.

Returning to the interior surface 70 of the receiver arms 62, located below the guide and advancement structure 72 is a discontinuous cylindrical surface 82 partially defining a run-out feature for the guide and advancement structure 72. The cylindrical surface 82 has a diameter equal to or slightly greater than a greater diameter of the guide and advancement structure 72. Moving downwardly, in a direction toward the base 60, following the cylindrical surface 82 of each arm is a cylindrical surface (or, in some embodiments, a tapered surface) 88 located below an annular run-out seat or surface 85 that extends inwardly toward the axis B and runs perpendicular or somewhat obliquely towards the axis B. The surface 88 has a diameter smaller than the diameter of the surface 82. The surface 88 is sized and shaped to initially closely receive a portion of the insert 14. A discontinuous annular surface or narrow ledge 89 is located below the surface 88 and is substantially perpendicular to the axis B. A partially discontinuous cylindrical surface 90 is located on each arm below and adjacent to the surface 89. The surface 90 also defines an upper cylindrical surface of the base cavity 61. The surface 90 has a diameter slightly smaller than the diameter of the surface 88. It is noted that in some embodiments of the invention, the surfaces 88 and 90 are combined and form a single cylindrical surface.

Figure 30:
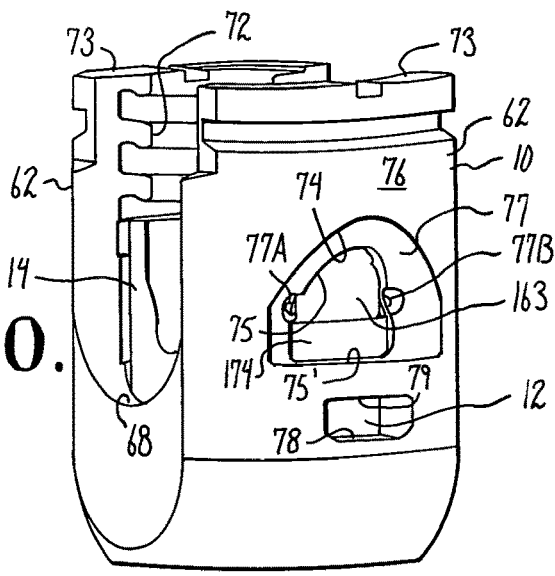
FIG. 30 is an enlarged perspective view of the receiver, retainer and insert of FIG. 29, further showing the receiver crimped to the insert.

The through bores 75 of the apertures 74 each extend through the arms at the surfaces 82 and 88 with the sloping tool engagement and crimp walls 77 extending substantially on either side of each bore surface 75 and formed in the arm outer surfaces 76 at a location opposite the inner surfaces 82 and 88. Thus, portions of the surfaces 88 are pressed into engagement with the insert 14 when the thin, deformable edge portions of the walls 77 are pressed toward the insert 14 as will be described in greater detail below. With reference to FIG. 30, the crimp wall portions that are pressed into engagement with the insert 14 are identified as 77A and 77B. It is foreseen that the crimp wall portions could be in the form of deformable crimp tabs.

Figure 28:
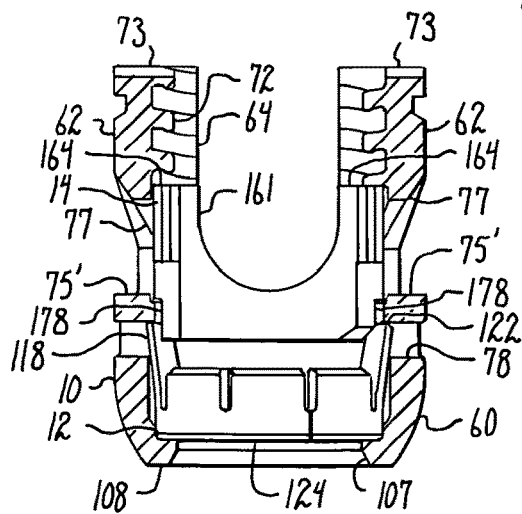
FIG. 28 is a front elevational view with portions broken away, similar to FIG. 27, showing the insert rotated into a position in alignment with the receiver.

Returning to FIGS. 8 and 9, an annular surface 98 partially defining the base cavity 61 and is located below and adjacent to the cylindrical surface 90. The surface 98 is disposed substantially perpendicular to the axis B, but could be oblique. Another cylindrical surface 99 is located below and adjacent to the surface 98. The cylindrical surface 99 is oriented substantially parallel to the axis B and is sized and shaped to receive an expanded portion of retainer 12. The surfaces 98 and 99 define a circumferential recess that is sized and shaped to receive the retainer 12 as it expands around the shank upper portion 8 as the shank 8 moves upwardly toward the channel 64 during assembly. It is foreseen that the recess could be tapered or conical in configuration. A cylindrical surface 101 located below the cylindrical surface 99 is sized and shaped to closely receive and surround a lower portion of the retainer 12 when the retainer is in a substantially neutral position as shown in FIG. 28, for example. Thus, the cylindrical surface 101 has a diameter smaller than the diameter of the cylindrical surface 99 that defines the expansion area or expansion chamber for the retainer 12. The surface 101 is joined or connected to the surface 99 by one or more beveled, curved or conical surfaces 102. The surfaces 102 allow for sliding and neutral or nominal positioning of the retainer 12 into the space defined by the surface 101 and ultimate seating of the retainer 12 on a lower substantially horizontal annular surface 104 located below and adjacent to the cylindrical surface 101.

Located below and adjacent to the annular seating surface 104 is another substantially cylindrical surface 106 that communicates with a beveled or flared bottom opening surface 107, the surface 107 communicating with an exterior base surface 108 of the base 60, defining a lower opening, generally 110, into the base cavity 61 of the receiver 10.

With particular reference to FIGS. 1 and 10-15, the lower open or split friction fit retainer 12, that operates to capture the shank upper portion 8 within the receiver 10, has a central axis that is operationally the same as the axis B associated with the receiver 10 when the shank upper portion 8 and the retainer 12 are installed within the receiver 10. The retainer 12 includes a substantially cylindrical discontinuous lower body 116, a plurality of flex fingers or panels, 117 extending upwardly from the body 116 and a pair of opposed spring arms or tabs 118, also extending upwardly from the body 116. The retainer ring 12 is made from a resilient material, such as a stainless steel or titanium alloy, so that the retainer 12 body 116 may be expanded and the fingers and tabs (117 and 118) of the retainer may be manipulated during various steps of assembly as will be described in greater detail below. The retainer 12 has a central channel or hollow through bore, generally 121, that passes entirely through the retainer 12 from tab 118 top surfaces 122 to a bottom surface 124 of the retainer body 116. Surfaces that define the channel or bore 121 at the body 116 include an inner lower frusto-conical surface 128 adjacent to the retainer body bottom surface 124, a substantially cylindrical surface 130 adjacent the frusto-conical surface 128 and a partially continuous partially discontinuous substantially spherical surface 132 located adjacent the cylindrical surface 130, the surface 132 being substantially continuous near the surface 130 and at each of the spring tabs 118 and otherwise broken by a through slot or slit, generally 134 and a plurality of evenly spaced partial slots or grooves 136. The grooves 136 separate the surface 132 into a plurality of segments or pieces that have already been described herein as the flex fingers 117. The grooves or slots 136 run outwardly and upwardly from the retainer body 116 through an upper surface 137 of the retainer 12 located between the spring tabs 118. In the illustrated embodiment, the slots 136 and the through slit 134 form the six substantially uniform flex fingers or tabs 117 as well as partially define the two spring tabs 118, each finger 117 having the inner spherical surface 132 while each of the spring tabs 118 extend outwardly and away from the surface 132 at the retainer body 116. It is foreseen that more or fewer flex fingers may be made by the forming of more or fewer slots 136 and that the surface 132 could be planar, tapered, faceted or otherwise curved. The illustrated discontinuous spherical surface 132 is sized and shaped to closely fit about and snap onto the shank surface 34 during assembly as will be described in greater detail below. Preferably the surface 132 has a radius the same, slightly smaller or slightly larger than the radius of the spherical shank surface 34. The surface 132 could be bent or deformed inwardly or outwardly to better cooperate with the shank head. In operation, the discontinuous surface 132 advantageously frictionally engages the bone screw shank upper portion or head 8, allowing for an un-locked friction fit, non-floppy placement of the angle of the shank 4 with respect to the receiver 10 during surgery prior to locking of the shank 4 with respect to the receiver 10 near the end of the procedure. At the time of locking engagement, as shown in FIG. 37, for example, downward and outward force placed on the retainer 12 by the shank upper portion 8 expands the retainer body 116 at the slit 134 and the individual flex fingers 117 no longer frictionally grip the spherical head surface 34 of the upper portion 8. To aid in bending flexibility and resiliency, some or all of the flex fingers 117 may have sloping outer surfaces or other geometry to gain the level of resiliency desired for expansion and gripping of the fingers 117 about the shank upper portion 8. For example, the illustrated fingers 117 each include an outer bevel 138. The spherical surfaces 132 may include a surface treatment or roughening to provide a desired friction fit. Again, it is noted that the surfaces 132 need not be spherical and may be planar or include other surface geometries that resiliently grip the shank upper portion or head 8. Again, in some embodiments, the flexible tabs 117 may be bent or deformed to further enhance frictional engagement. It is noted that the fingers 117 that are directed generally upwardly toward the receiver channel 64 advantageously sufficiently snap about and then grip the shank surface 34 to an extent to provide the friction fit desired for non-floppy placement of the shank body 6 at a desired angle with respect to the receiver 10 during manipulation of the bone screws 1 and the rod 21 or other longitudinal connecting member during surgery. However, as compared to bone screw inserts such as collets known in the art that include downwardly directed portions or panels that are ultimately wedged between a receiver surface and a shank surface upon final locking of the shank to the receiver, the thin upwardly directed fingers 117 that extend away from the shank locking surface that are not as strong as the retainer body 116 or the insert 114, do not participate or cooperate with the final locking of the insert 114 to the shank upper portion 8, the shank upper portion 8 to the retainer 12, and the retainer 12 to the receiver inner and substantially planar surfaces 101 and 104. For such purpose, the more substantial retainer body 116 located below the slots 136 having only the very narrow slit 134, used for expansion purposes only, is the component or portion that locks the shank upper portion 8 between the receiver 10, the insert 114 and the rod 21 or other longitudinal connecting member.

The retainer body 116 and the flex fingers 117 have an outer substantially cylindrical profile, sized and shaped to closely and slidingly fit within the receiver cavity 61. The opposed pair of spring tabs 118, however, extend outwardly away from one another and thus outwardly from the body 116. Each spring tab 118 is sized and shaped to closely cooperate and frictionally engage upper surfaces 79 defining the through bores 78. An outer surface 143 of each spring tab 118 located adjacent each upper surface 122 is sized and shaped to cooperate with and frictionally engage the cylindrical surface 90 during assembly and shipping as shown, for example, in FIG. 31. In some embodiments of the invention, the tab 118 surface 143 may include one or more projections, grooves or notches as needed for tooling to resiliently hold the retainer in an upper portion of the cavity 61 when desired, but readily release the retainer 12 into a lower portion of the receiver cavity 61 once the retainer flex tabs 117 engage the shank head 8. The illustrated spring tabs 118 each include one or more planar or curved concave inner surfaces 144 running from the top surface 122 to a tab base seat, surface or surfaces 145 located adjacent to and running laterally outwardly from the surface 132. The surfaces 144 extend both outwardly and upwardly from the base seat surfaces 145. It is foreseen that in other embodiments of the invention, fewer or greater number of planar or other surfaces with other geometries may extend between the top surface 122 and the inner surfaces defining the body 116 of the retainer 12.

The through slit 134 of the resilient retainer 12 is defined by first and second end surfaces, 146 and 147 disposed in spaced relation to one another (they may also be touching) when the retainer is in a neutral state. Both end surfaces 146 and 147 are disposed substantially perpendicular to the bottom surface 124. A width X between the surfaces 146 and 147 is very narrow (slit may be made by EDM process) to provide stability to the retainer 12 during operation. Because the retainer 12 is top loadable in a neutral state and the retainer 12 does not need to be compressed to fit within the receiver cavity 61, the width X may be much smaller than might be required for a bottom loaded compressible retainer ring. The gap X functions only in expansion to allow the retainer 12 to expand about the shank upper portion 8. This results in a stronger retainer that provides more surface contact with the shank upper portion 8 upon locking, resulting in a sturdier connection with less likelihood of failure than a retainer ring having a greater gap. Furthermore, because the retainer 12 body 116 is only expanded and never compressed inwardly, the retainer 12 does not undergo the mechanical stress that typically is placed on spring ring type retainers known in the prior art that are both compressed inwardly and expanded outwardly during assembly.

It is foreseen that in some embodiments of the invention, the retainer 12 inner surfaces may include a roughening or additional material to increase the friction fit against the shank upper portion 8 prior to lock down by the rod 21 or other longitudinal connecting member. Also, the embodiment shown in FIGS. 10-15 illustrates the surfaces 146 and 147 as substantially parallel, however, it is foreseen that it may be desirable to orient the surfaces obliquely or at a slight angle.

With particular reference to FIGS. 1 and 16-21, the compression insert 14 is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8. As will be described in greater detail below with respect to the insert 214, in some embodiments of the invention, the insert that has locked the shank 4 in a desired angular position with respect to the receiver 10, by, for example, compression from the rod 21 and closure top 18, is also forced into an interference fit engagement with the receiver 10 at an outer cylindrical surface thereof and thus is capable of retaining the shank 6 in a locked position even if the rod 21 and closure top 18 are removed. Such locked position may also be released by the surgeon if desired. The non-locking insert 14 as well as the locking insert 214 are preferably made from a solid resilient material, such as a stainless steel or titanium alloy, so that portions of the insert may be pinched and un-wedged from the receiver 10 with a release tool.

The non-locking compression insert 14 includes a substantially cylindrical body 156 integral with a pair of upstanding arms 157. A bore, generally 160, is disposed primarily within and through the body 156 and communicates with a generally U-shaped through channel 161 that is defined by the upstanding arms 157. The channel 161 has a lower seat 162 sized and shaped to closely, snugly engage the rod 21. It is foreseen that an alternative embodiment may be configured to include planar holding surfaces that closely hold a square or rectangular bar as well as hold a cylindrical rod-shaped, cord, or sleeved cord longitudinal connecting member. The arms 157 disposed on either side of the channel 141 extend upwardly and outwardly from the body 156. The arms 157 are sized and configured for ultimate placement beneath the cylindrical run-out surface 82 located below the receiver guide and advancement structure 72. It is foreseen that in some embodiments of the invention, the arms may be extended and the closure top configured such that the arms and, more specifically, the surfaces 164 ultimately directly engage the closure top 18 for locking of the polyaxial mechanism, for example, when the rod 21 is made from a deformable material. In such embodiments, the insert 14 would include a rotation blocking structure or feature that abuts against cooperating structure located on an inner wall of the receiver 10, preventing rotation of the insert with respect to the receiver when the closure top is rotated into engagement with the insert. In the present embodiment, the arms 157 include upper outer cylindrical surfaces 163 and top surfaces 164 that are ultimately positioned in spaced relation with the closure top 18, so that the closure top 18 frictionally engages the rod 21 only, pressing the rod 21 downwardly against the seating surface 162, the insert 14 in turn pressing against the shank 4 upper portion 8 that presses against the retainer 12 to lock the polyaxial mechanism of the bone screw assembly 1 at a desired angle.

The bore, generally 160, is substantially defined at the body 156 by an inner cylindrical surface 166 that communicates with the seat 162 and a lower concave substantially spherical surface 168 having a radius the same or substantially similar to a radius of the surface 34 of the shank upper portion 8. The surface 168 terminates at an annular and substantially planar base surface 169 of the body 156. Located between the cylindrical surface 166 and the spherical surface 168 or located along the spherical surface 168 is a shank gripping surface portion, generally 170. The gripping surface portion 170 includes one or more stepped surfaces or ridges sized and shaped to grip and penetrate into the shank head 8 when the insert 14 is locked against the head surface 34. It is foreseen that the stepped surface portion 170 may include greater or fewer number of stepped surfaces. It is foreseen that the shank gripping surface portion 170 and also the spherical surface 168 may additionally or alternatively include a roughened or textured surface or surface finish, or may be scored, knurled, or the like, for enhancing frictional engagement with the shank upper portion 8.

The compression insert 14 through bore 160 is sized and shaped to receive the driving tool (not shown) therethrough that engages the shank drive feature 46 when the shank body 6 is driven into bone with the receiver 10 attached. Also, in some locking embodiments of the invention, the bore receives a manipulation tool (not shown) used for releasing the insert from a locked position with the receiver, the tool pressing down on the shank and also gripping the insert at through bores located in the arms or with other tool engaging features. For example, a manipulation tool for releasing the insert from the receiver 10 may also access such bores from the receiver through the apertures 74 in the receiver. Thereby, tools can be configured to release a locking insert from the inside and outside of the receiver 10.

Figure 27:
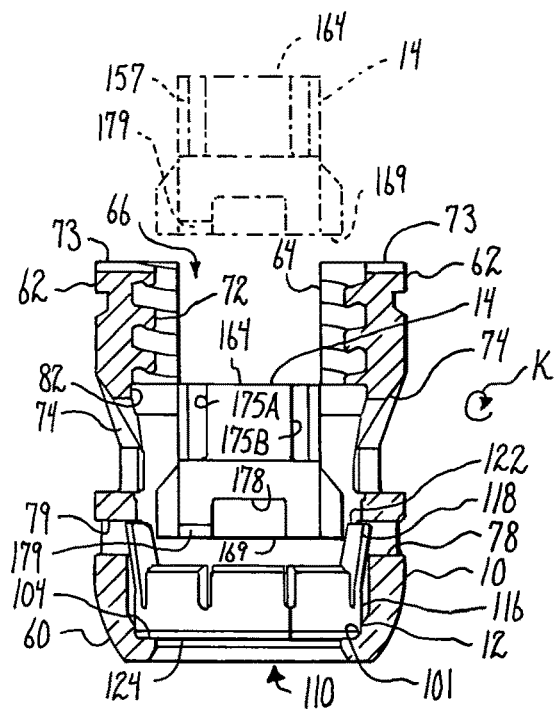
FIG. 27 is a front elevational view of the retainer and receiver with portions broken away, similar to what is shown in FIG. 26, further showing an enlarged side elevational view of the insert of FIG. 1 (in phantom) above the receiver and then in solid lines being downloaded into the receiver to a partially inserted stage of assembly.
Figure 29:
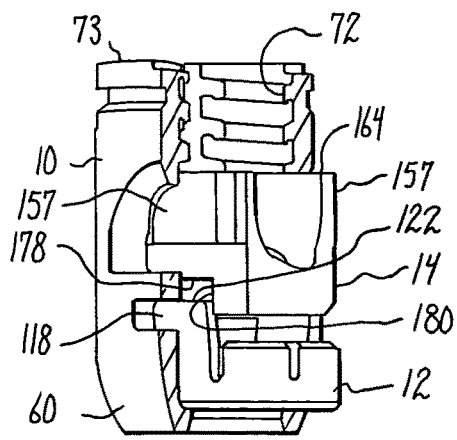
FIG. 29 is a perspective view, with portions broken away, of the receiver, retainer and insert of FIG. 28.

The illustrated insert 14 further includes an outer lower arm surface 174 adjacent to the upper arm outer surface 164 and having a radius slightly smaller than a radius of the upper arm surfaces 163. The arm surfaces 163 further include notches or grooves formed thereon. In the illustrated embodiments, each surface 163 includes a pair of spaced v-notches or grooves 175A and 175B that run from the respective top surface 164 to the respective lower arm surface 174. The grooves 175 cooperate with the receiver crimp walls 77 to aid in alignment of the insert channel 161 with the receiver channel 64. Each lower arm surface 174 runs from the mid-point or location of the arm to the insert bottom surface 169. Each surface includes a recessed area or portion 178 sized and shaped to receive and allow clearance for the upper surface 122 of the retainer spring tabs 118, as shown, for example, in FIG. 31, during assembly and shipping of the pre-assembled receiver 10, retainer 12 and insert 14. Adjacent each recessed area or portion 178 is a bevel or flat surface 179 cut into the lower outer surface 174 near the base or bottom surface 169. Thus, there are two surfaces 179 located on either side of the insert 14 at opposite sides thereof. As best shown in FIGS. 27-29, and described in greater detail below, the surfaces 170 allow for clockwise rotation of the insert 14 into place within the receiver, the bevel or flat 179 allowing clearance between the insert 14 and the retainer spring tab 118 during rotation into place. Once the insert 14 is in the desired position within the receiver, the insert surface located adjacent the recess 178 that is not beveled, identified by the reference number 180, prohibits further rotation of the insert as best shown, for example, in FIG. 29.

The insert body 156 has an outer diameter slightly smaller than a diameter between crests of the guide and advancement structure 72 of the receiver 10, allowing for top loading of the compression insert 14 into the receiver opening 66, with the arms 157 of the insert 14 being located between the receiver arms 62 during insertion of the insert 14 into the receiver 10. Once the arms 157 of the insert 14 are generally located beneath the guide and advancement structure 72, the insert 14 is rotated in a clockwise direction K into place about the receiver axis B until the top surfaces 164 are located directly below the guide and advancement structure 72 as will be described in greater detail below. The insert outer arm surfaces 174 are sized and shaped to be slidingly received by the receiver surface 90 during final locking of the assembly 1.

With reference to FIGS. 1 and 36-37, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys, non-metals and deformable and less compressible plastics, including, but not limited to rods made of elastomeric, polyetheretherketone (PEEK) and other types of materials, such as polycarbonate urethanes (PCU) and polyethelenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 36-37, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes a an outer helically wound guide and advancement structure 182 in the form of a flange that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 184 with an internal drive 186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 186 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 188 of the closure is planar and further includes a point 189 and a rim 190 for engagement and penetration into the surface 22 of the rod 21 in certain embodiments of the invention. It is noted that in some embodiments, the closure top bottom surface 188 does not include the point and/or the rim. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

Figure 49:
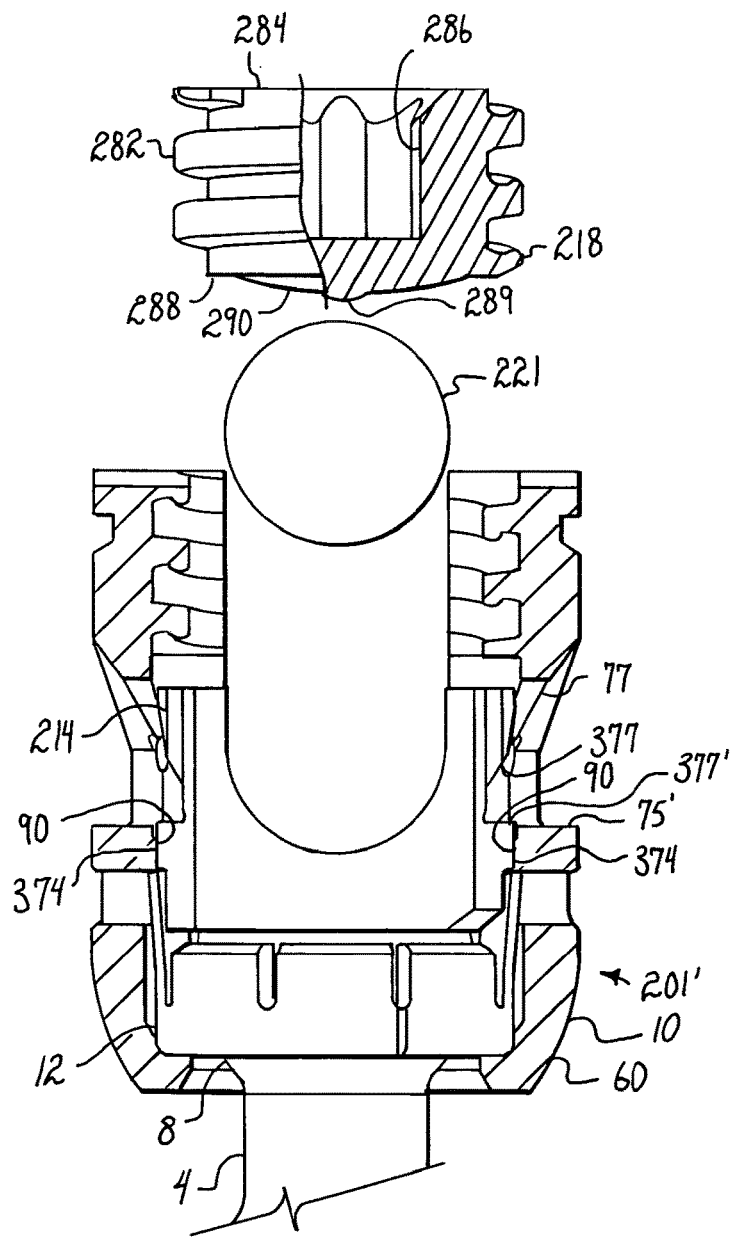
FIG. 49 is an enlarged and partial front elevational view with portions broken away, similar to FIG. 48, showing the shank, retainer, insert and receiver remaining in a locked position after removal of the rod and closure top of FIG. 1 and further showing, in exploded view, an alternative deformable rod and cooperating alternative closure top.
Figure 50:
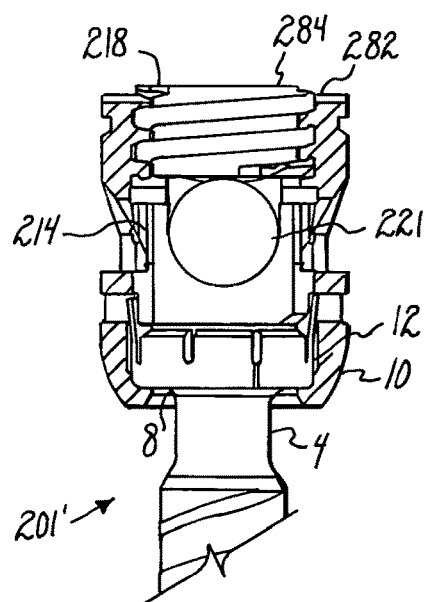
FIG. 50 is a reduced and partial front elevational view with portions broken away, similar to FIG. 49, showing the alternative rod and closure top fixed to the remainder of the assembly.

An alternative closure top 218 for use with a deformable rod, such as a PEEK rod 221, is shown in FIGS. 49 and 50. The top 218 is identical to the top 18 with the exception that a point or nub 289 is located on a domed surface 290 in lieu of the point and rim of the closure top 18. The closure top 218 otherwise includes a guide and advancement structure 282, a top 284, an internal drive 286 and a bottom outer rim surface 288 that same or substantially similar to the guide and advancement structure 182, top 184, internal drive 186 and a bottom surface 188 described herein with respect to the closure top 18. In some embodiments, the internal drive 286 is not as large as the drive 186 of the closure top 18, such smaller drive providing for less force being placed on a deformable rod, for example, and not being required when a locking insert, for example, the insert 218 discussed below is utilized in a bone screw assembly of the invention.

Returning to the assembly 1, preferably, the receiver 10, the retainer 12 and the compression insert 14 are assembled at a factory setting that includes tooling for holding and alignment of the component pieces and pinching or compressing of the retainer 12 spring tabs 118 and rotating and otherwise manipulating the insert 14 arms, as well as crimping a portion of the receiver 10 toward the insert 14. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost and improving logistics and distribution.

Pre-assembly of the receiver 10, retainer 12 and compression insert 14 is shown in FIGS. 22-31. With particular reference to FIG. 22, first the retainer 12 is inserted into the upper receiver opening 66, leading with one of the spring tabs 118 with both of the spring tab top surfaces 122 facing one arm 62 and the retainer bottom surface 124 facing the opposing arm 62 (shown in phantom). The retainer 12 is then lowered in such sideways manner into the channel 64 and partially into the receiver cavity 61, followed by tilting the retainer 12 such that the top surface 122 and thereafter the top surface 122 of the leading spring tab 118 is moved into a nearby receiver arm aperture 74 below the arched through bore surface 75. With reference to FIG. 23, the retainer 12 is then further tilted or turned and manipulated within the receiver to a position within the cavity until the retainer 12 bottom surface 124 is directed toward the receiver cavity 61 and the spring tab upper surfaces 122 are facing upwardly toward the receiver channel opening 66 as shown in FIG. 24. To accomplish such tilting and turning of the retainer 12, the spring tab arm 118 located within the receiver bore surface 75 is manipulated downwardly and then upwardly within such bore and finally shifted out of such bore when the opposed spring tab arm 118 moves past and clears the guide and advancement structure 72 of the receiver 10. With further reference to FIG. 24 and also FIG. 25, the retainer 12 is moved downwardly toward the receiver base 60 and the spring tabs 118 are pressed resiliently toward one another as the retainer spring tab outside surfaces 143 abut against the receiver cylindrical surfaces 90. With reference to FIG. 26, once the retainer bottom surface 124 seats on the receiver surface 104, the spring tab surfaces 143 clear the surface 90 and the tabs spring back out to a substantially neutral position with portions of the top surfaces 122 of each of the spring tabs 118 being located beneath the surfaces 79 of the through bores 78. At this time, the retainer 12 is captured within the receiver base cavity 61 unless the spring tabs 118 are squeezed toward one another so as to clear the through bores 78.

With reference to FIG. 27, the compression insert 14 is then downloaded into the receiver 10 through the upper opening 66 with the bottom surface 169 facing the receiver arm top surfaces 73 and the insert arms 157 located between the opposed receiver arms 62. The insert 14 is then lowered toward the receiver base 60 until the insert 14 arm upper surfaces 164 are adjacent the run-out area below the guide and advancement structure 72 defined in part by the cylindrical surface 82. Thereafter, the insert 14 is rotated in a clockwise manner (see the arrow K) about the receiver axis B until the upper arm surfaces 164 are directly below the guide and advancement structure 72 as illustrated in FIG. 28 with the U-shaped channel 161 of the insert 14 aligned with the U-shaped channel 64 of the receiver 10. In some embodiments, the insert arms 157 may need to be compressed slightly during rotation to clear inner surfaces of the receiver arms 62. As shown in FIGS. 27-29, the bevel or flat 179 at the base of the arm portion 157 is initially received within one of the receiver arms 62 when the clock-wise rotation is begun, the flat 179 clearing the retainer spring tab 118 during rotation. However, as there is no such flat surface on the other side of the recess or aperture 178, the surface 180 partially defining the recess 178 abuts against the spring tab 118 at a desirable location wherein the insert U-shaped channel 161 is aligned with the receiver channel 64. This is best seen in FIG. 29. With reference to FIG. 30, thereafter, a pair of crimps 77A and 77B are made in the receiver surface 77, the crimps 77A and 77B are pressed toward the insert 14 at respective grooves 175A and 175B. The, crimped portions 77A and 77B help retain the desired alignment between the insert 14 and the receiver 10 and prohibit relative rotation between the two parts. However, relative vertical movement between the insert 14 and the receiver 10 is possible as the crimps do not vertically fix the insert with respect to the receiver.

Figure 31:
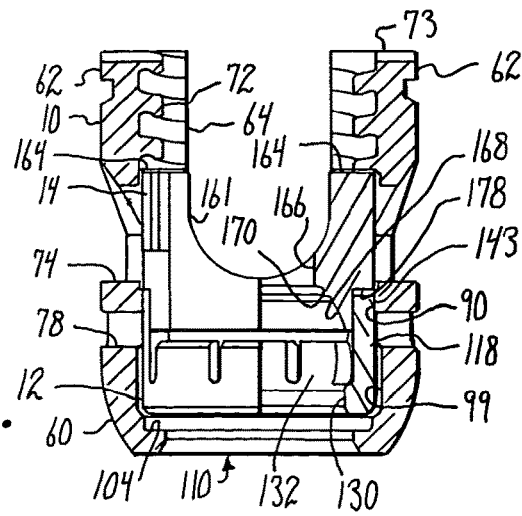
FIG. 31 is a reduced front elevational view of the receiver, retainer and insert of FIG. 30 with portions broken away to show the detail thereof, showing the retainer spring tab arms placed in a desired upward position within the receiver so that the retainer spring tabs push resiliently outwardly against the receiver, holding the retainer against the receiver and keeping the insert in an upward position during shipping.

With further reference to FIG. 31, a tool (not shown) is then used to grip the retainer spring tab arms 118 at outer surfaces 143 thereof and squeeze or press the tabs 118 toward one another while moving the retainer 12 in an upward direction away from the surface 104. When the spring tab surfaces 143 are located within the cylindrical surface 90 and are partially received in the insert recesses 178, the tool (not shown) is released and a portion of the surface 143 of each spring tab 118 spring out to engage the surface portion 90. The retainer 12 and the insert 14 are now in a desired position for shipping as an assembly along with the separate shank 4. The insert 14 recessed areas 178 are now located adjacent to the retainer spring tab top surfaces 122. The insert 14 is fully captured within the receiver 10 by the guide and advancement structure 72 prohibiting movement of the insert 14 up and out through the receiver opening 66 as well as by retainer 12 located below the insert.

Typically, the receiver and retainer combination are shipped or otherwise provided to the end user with the spring tabs 118 wedged against the receiver as shown in FIG. 31. The receiver 10, retainer 12 and insert 14 combination is now pre-assembled and ready for assembly with the shank 4 either at the factory, by surgery staff prior to implantation, or directly upon an implanted shank 4 as will be described herein.

Figure 32:
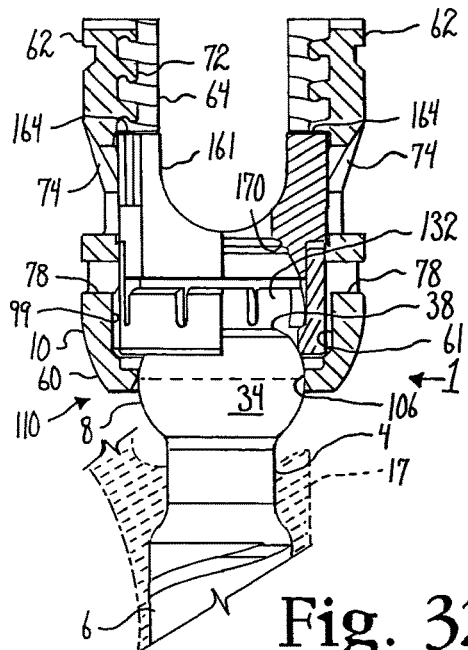
FIG. 32 is a front elevational view with portions broken away, similar to FIG. 31, and further showing an enlarged and partial shank of FIG. 1 in a first stage of assembly with the retainer, a hemisphere of the shank head and a vertebra portion are both shown in phantom.

As illustrated in FIG. 32, the bone screw shank 4 or an entire assembly 1 made up of the assembled shank 4, receiver 10, retainer 12 and compression insert 14, is screwed into a bone, such as the vertebra 17 (shown in phantom), by rotation of the shank 4 using a suitable driving tool (not shown) that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires and attachable tower tools mating with the receiver. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

Figure 33:
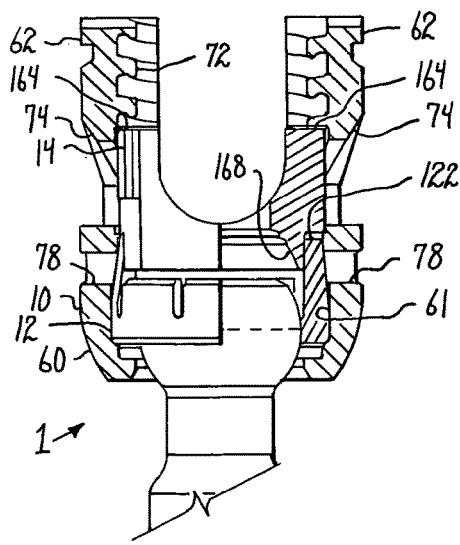
FIG. 33 is a partial front elevational view with portions broken away, similar to FIG. 32, showing the retainer lower portion in an expanded state about a mid-portion of the shank head, the head hemisphere shown in phantom.
Figure 34:
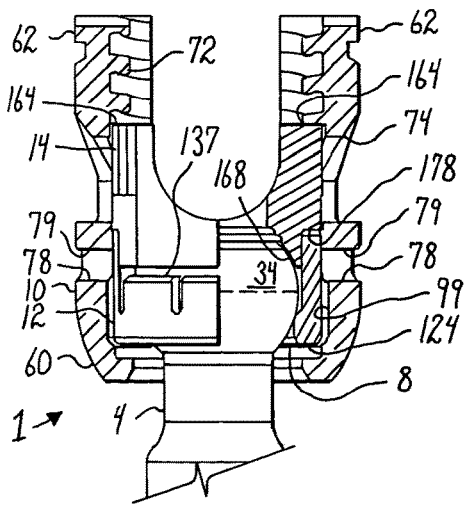
FIG. 34 is a reduced partial front elevational view with portions broken away, similar to FIG. 33, the shank upper portion or head in frictional engagement with an upper portion of the retainer.

With further reference to FIG. 32, the pre-assembled receiver, insert and retainer are placed above the shank upper portion 8 until the shank upper portion is received within the opening 110. With particular reference to FIGS. 32, 33 and 34, as the shank upper portion 8 is moved into the interior 61 of the receiver base, the shank upper portion 8 presses upwardly against the retainer 12 in the recess partially defined by the cylindrical surface 99. As the portion 8 continues to move upwardly toward the channel 64, the surface 34 forces outward movement of the retainer 12 towards the cylindrical surface 99 defining the receiver expansion recess or chamber as shown in FIG. 33. With reference to FIG. 34, the retainer 12 begins to return to its neutral state as the center of the sphere (shown in dotted lines) passes beyond the center of the retainer expansion recess. At this time also, the spherical surface 34 moves into engagement with the surfaces 132 of the retainer flex tabs 117, the tabs 117 expanding slightly outwardly to receive the surface 34. With further reference to FIG. 34, the spherical surface 34 then enters into full frictional engagement with the panel inner surfaces 132. At this time, the retainer 12 panels and the surface 34 are in a fairly tight friction fit, the surface 34 being pivotable with respect to the retainer 12 with some force. Thus, a tight, non-floppy ball and socket joint is now created between the retainer 12 and the shank upper portion 8.

Figure 35:
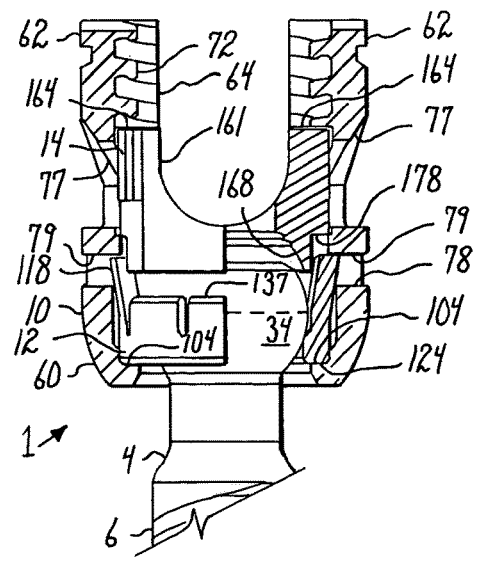
FIG. 35 is a partial front elevational view with portions broken away, similar to FIG. 34, the shank upper portion with attached retainer being shown pulled down into a seated position within the lower receiver cavity, the retainer spring tabs in a substantially neutral state, extending outwardly partially into receiver apertures.

With reference to FIG. 35, the receiver is then pulled upwardly or the shank 4 and attached retainer 12 are then moved downwardly into a desired position with the retainer seated on the surface 104. Again, this may be accomplished by either an upward pull on the receiver 10 or, in some cases, by driving the shank 4 further into the vertebra 17. At this time, the retainer spring tabs 118 once against spring outwardly into the receiver bores 78, making it impossible to move the retainer out of the locking portion of the chamber defined in part by the receiver seat 104 unless pressed inwardly by a tool or tools via the through bores 78. With reference to FIG. 36, the insert 14 may be pressed downwardly by a tool or by the rod 21 and the closure top 18. Also, in some embodiments, when the receiver 10 is pre-assembled with the shank 4, the entire assembly 1 may be implanted at this time by inserting the driving tool (not shown) into the receiver and the shank drive 46 and rotating and driving the shank 4 into a desired location of the vertebra 17.

Figure 54:
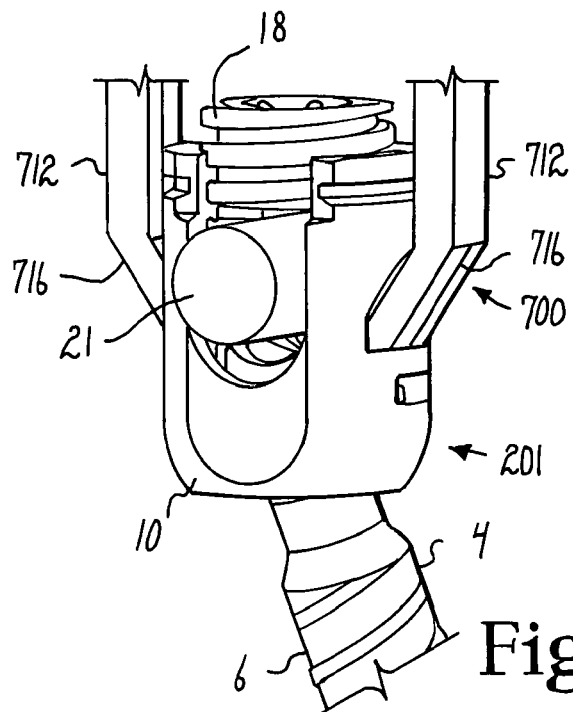
FIG. 54 is an enlarged and partial perspective view of the assembly of FIG. 1, shown in a position similar to what is shown in FIG. 47, but with the shank being at an angle with respect to the receiver and further showing an alternative locking tool for independently locking the insert into an interference fit with the receiver and thus locking the shank with respect to the receiver even when the closure top and rod are in a loose, unlocked relationship with the receiver as shown.

With reference to FIG. 36 and also, for example, to FIG. 54 (that shows the use of the assembly 1 with an alternative insert), at this time, the receiver 10 may be articulated to a desired angular position with respect to the shank 4, such as that shown in FIG. 54, that will be held, but not locked, by the frictional engagement between the retainer 12 and the shank upper portion 8.

With further reference to FIGS. 36 and 37, the rod 21 is eventually positioned in an open or percutaneous manner in cooperation with the at least two bone screw assemblies 1. The closure structure 18 is then advanced between the arms 62 of each of the receivers 10. The closure structure 18 is rotated, using a tool engaged with the inner drive 186 until a selected pressure is reached at which point the rod 21 engages the U-shaped seating surface 162 of the compression insert 14, further pressing the insert spherical surface 168 and stepped shank gripping surfaces 170 against the shank spherical surface 34, the edges of the stepped surfaces 170 penetrating into the spherical surface 34, pressing the shank upper portion 8 into locked frictional engagement with the retainer 12. Specifically, as the closure structure 18 rotates and moves downwardly into the respective receiver 10, the point 189 and rim 190 engage and penetrate the rod surface 22, the closure structure 18 pressing downwardly against and biasing the rod 21 into compressive engagement with the insert 14 that urges the shank upper portion 8 toward the retainer 12 and into locking engagement therewith, the retainer 12 frictionally abutting the surface 104 and expanding outwardly against the cylindrical surface 101. For example, about 80 to about 120 inch pounds of torque on the closure top may be applied for fixing the bone screw shank 6 with respect to the receiver 10. If disassembly if the assembly 1 is desired, such is accomplished in reverse order to the procedure described previously herein for assembly.

Figure 47:
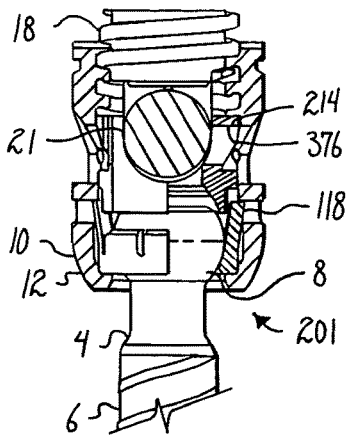
FIG. 47 is a reduced and partial front elevational view of the shank, receiver, retainer, rod and closure of FIG. 1 and the insert of FIG. 38, shown with portions broken away and in a final stage of assembly.
Figure 48:
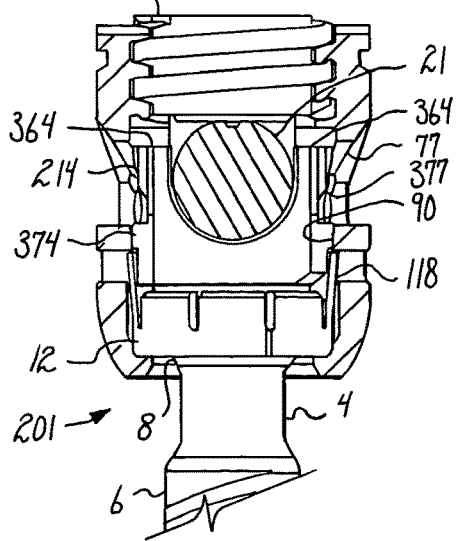
FIG. 48 is an enlarged and partial front elevational view with portions broken away, similar to FIG. 47, shown fully assembled and in a final locked position.

With reference to FIGS. 38-48, an alternative lock-and-release compression insert 214 is illustrated for use with the shank 4, receiver 10, retainer 12, closure top 18 and rod 21 previously described herein, the resulting assembly identified as an assembly 201 in FIGS. 47 and 48, for example. The insert 214 is substantially similar to the insert 14 previously described herein, with addition features that include positioning and locking apertures and bores and an outer cylindrical surface 374 that is sized for a locking interference fit with the cylindrical surface 90 of the receiver 10 as will be described in greater detail below.

Thus, the locking insert 214 includes a cylindrical body 356, opposed arms 357, a through bore 360, a U-shaped channel 361, a channel seat 362, outer upper arm surfaces 363, top arm surfaces 364, an inner cylindrical surface 366, an inner spherical surface 368, a base surface 369, an inner gripping portion 370, outer v-shaped grooves 375A and 375B, recessed areas 378, opposed bevels or flats 379 and a surface 380 partially defining the recessed area 378 that are the same or substantially similar in form and function to the respective cylindrical body 156, opposed arms 157, through bore 160, U-shaped channel 161, channel seat 162, outer upper arm surfaces 163, top arm surfaces 164, inner cylindrical surface 166, inner spherical surface 168, base surface 169, inner gripping portion 170, grooves 175A and 175B, recessed areas 178, opposed bevels or flats 179 and surfaces 180 partially defining each of the recessed areas 178 previously described herein with respect to the insert 14.

Furthermore, the insert 214 includes a lower arm surface 374 that is similar to the arm surface 174 of the insert 14 with the exception that the cylindrical surface 374 is sized for a locking interference fit with the receiver cylindrical surface 90. In other words, a diameter of the surface 374 is sized large enough to require that the cylindrical surface 374 must be forced into the cylindrical surface 90 by a tool or tools or by the closure top 18 forcing the rod 21 downwardly against the insert 214 with sufficient force to interferingly lock the insert into the receiver surface 90.

Figure 51:
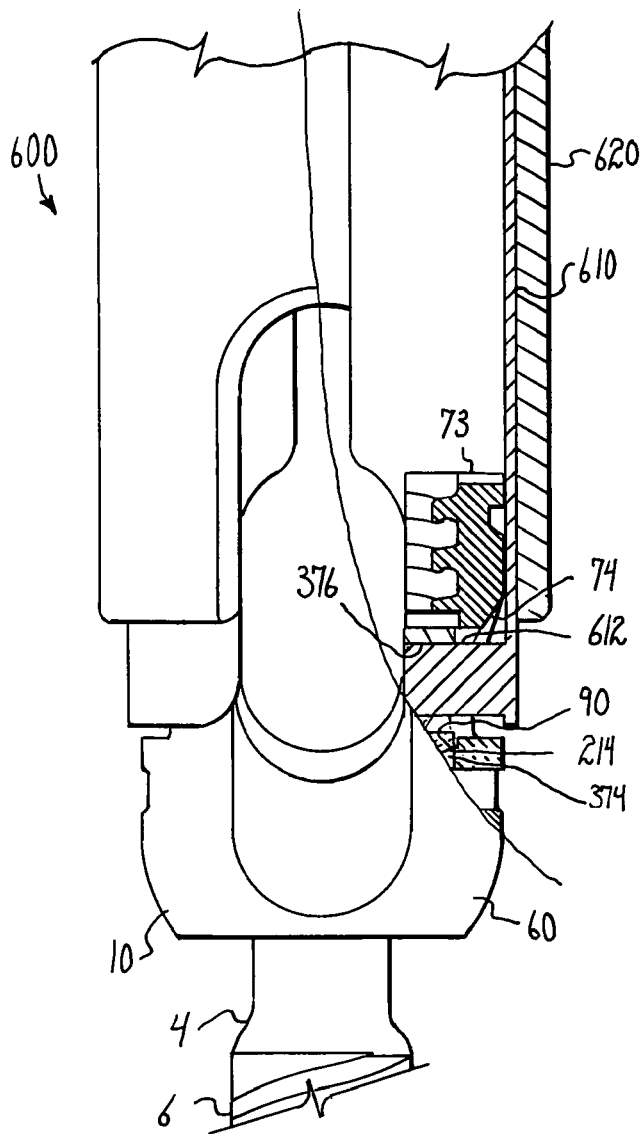
FIG. 51 is a reduced and partial front elevational view with portions broken away of the assembly of FIG. 49 without the alternative rod and closure top, and further showing unlocking of the insert from the receiver with a two-piece tool having an inner insert engaging portion and an outer tubular holding portion.
Figure 58:
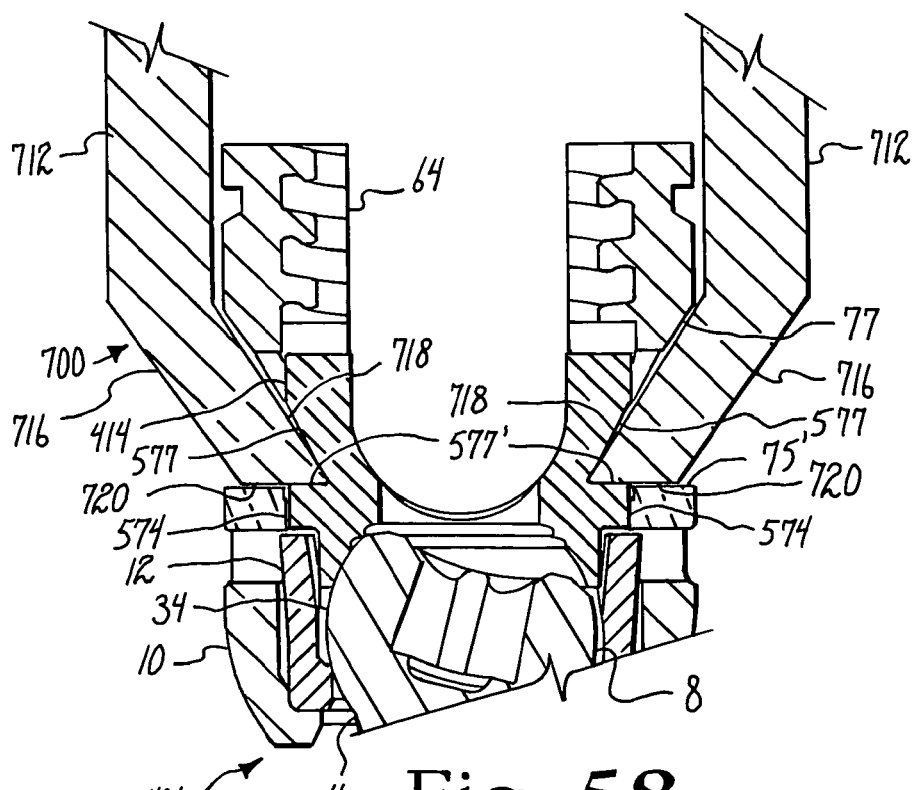
FIG. 58 is a partial front elevational view, similar to FIG. 56, with portions broken away to show the detail thereof, showing the assembly of FIG. 1 with the alternative insert of FIG. 57 and showing the locking tool pressing the insert into a locked position with respect to a remainder of the assembly.

In addition to the grooves 375A and 375B, the insert 214 upper arm surfaces 363 include a through hole or bore 376 for receiving tooling, such as that shown in FIGS. 51 and 58, for example. Formed in each surface 363 as well as in a portion of each outer surface 374 is a v-notch or recess formed from an upper sloping surface 377 and a lower planar surface 377'. The through holes 376 and surfaces 377 and 377' cooperate and align with the receiver aperture surfaces 75, 77 and 75' when receiving tooling as will be described in greater detail below.

With reference to FIGS. 45-48, the insert 214 is assembled with the receiver 10, retainer 12, shank 4, rod 21 and closure top 18 in a manner the same as previously described above with respect to the assembly 1, with the exception that the insert 214 must be forced downwardly into a locking interference fit with the receiver 10 when the shank 4 is locked in place, as compared to the easily sliding relationship between the insert 14 and the receiver 10. In particular, with reference to FIG. 45, prior to assembly with the rod 21 and the closure top 18, the compression insert 214 outer arm surfaces 374 are slidingly received by receiver surfaces 88, but are not received by the surfaces 90. The insert 214 is thus prohibited from moving any further downwardly at the beginning of the surface 90 unless forced downwardly by a locking tool or by the closure top pressing downwardly on the rod that in turn presses downwardly on the insert 214 as shown in FIGS. 47 and 48. With further reference to FIG. 47, at this time, the receiver 10 may be articulated to a desired angular position with respect to the shank 4, such as that shown in FIG. 54, for example, that will be held, but not locked, by the frictional engagement between the retainer 12 and the shank upper portion 8.

The rod 21 is eventually positioned in an open or percutaneous manner in cooperation with the at least two bone screw assemblies 1. The closure structure 18 is then inserted into and advanced between the arms 62 of each of the receivers 10. The closure structure 18 is rotated, using a tool engaged with the inner drive 186 until a selected pressure is reached at which point the rod 21 engages the U-shaped seating surface 362 of the compression insert 214, further pressing the insert spherical surface 368 and stepped shank gripping surfaces 370 against the shank spherical surface 34, the edges of the stepped surfaces 370 penetrating into the spherical surface 34, pressing the shank upper portion 8 into locked frictional engagement with the retainer 12. Specifically, as the closure structure 18 rotates and moves downwardly into the respective receiver 10, the point 189 and rim 190 engage and penetrate the rod surface 22, the closure structure 18 pressing downwardly against and biasing the rod 21 into compressive engagement with the insert 214 that urges the shank upper portion 8 toward the retainer 12 and into locking engagement therewith, the retainer 12 frictionally abutting the surface 104 and expanding outwardly against the cylindrical surface 101. For example, about 80 to about 120 inch pounds of torque on the closure top may be applied for fixing the bone screw shank 6 with respect to the receiver 10. Tightening the helical flange form to 100 inch pounds can create 1000 pounds of force and it has been found that an interference fit is created between the cylindrical portions 374 of the insert 214 and the cylindrical portions 90 of the receiver at between about 700-900 inch pounds. So, as the closure structure 18 and the rod 21 press the insert 14 downwardly toward the base of the receiver 10, the insert cylindrical surface 374 is forced into the receiver cylindrical surface 90, thus forcing and fixing the insert 14 into frictional interference engagement with the receiver surface 90.

With reference to FIG. 49, at this time, the closure top 18 may be loosened or removed and/or the rod 21 may be adjusted and/or removed and the frictional engagement between the insert 214 and the receiver 10 at the receiver surface 90 will remain locked in place, advantageously maintaining a locked angular position of the shank 4 with respect to the receiver 10.

With further reference to FIGS. 49 and 50, at this time, another rod, such as the deformable rod 221 and cooperating alternative closure top 218 may be loaded onto the already locked-up assembly to result in an alternative assembly 201'. As mentioned above, the closure drive 286 may advantageously be made smaller than the drive of the closure 18, such that the deformable rod 221 is not unduly pressed or deformed during assembly since the polyaxial mechanism is already locked.

Figure 52:
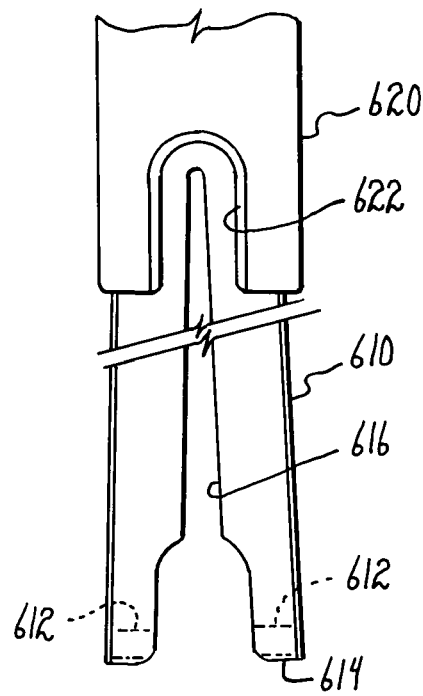
FIG. 52 is a reduced and partial front elevational view of the two-piece tool of FIG. 51, holding prongs of the inner insert engaging portion being shown in phantom.
Figure 53:
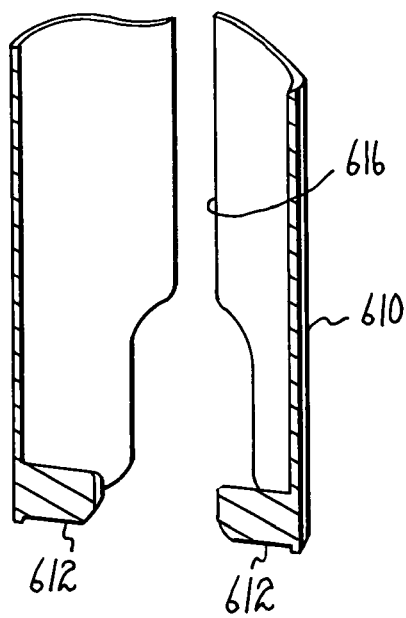
FIG. 53 is an enlarged and partial front elevational view of the inner insert engaging portion of the tool shown in FIG. 52 with portions broken away to show the detail thereof.

With reference to FIGS. 51-53, a two-piece tool 600 is illustrated for releasing the insert 214 from the receiver 10. The tool 600 includes an inner flexible tube-like structure with opposed inwardly facing prongs 612 located on either side of a through-channel 616. The channel 616 may terminate at a location spaced from the prongs 612 or may extend further upwardly through the tool, resulting in a two-piece tool 610. The tool 600 includes an outer, more rigid tubular member 620 having a smaller through channel 622. The member 620 slidingly fits over the tube 610 after the flexible member 610 prongs 612 are flexed outwardly and then fitted over the receiver 10 and then within through bores of the opposed apertures 74 of the receiver 10 and aligned opposed bores 376 located on arms of the insert 214. In FIG. 51, the tool 600 is shown during the process of unlocking the insert 214 from the receiver 10 with the outer member 620 surrounding the inner member 610 and holding the prongs 612 within the receiver and insert apertures while the tool 600 is pulled upwardly away from the shank 4. It is foreseen that the tool 600 may further include structure for pressing down upon the receiver 10 while the prongs and tubular member are pulled upwardly, such structure may be located within the tool 600 and press down upon the top surfaces 73 of the receiver arms, for example.

Alternatively, another manipulation tool (not shown) may be used that is inserted into the receiver at the opening 66 and into the insert channel 361, with prongs or extensions thereof extending outwardly into the insert through bores 376; a piston-like portion of the tool thereafter pushing directly on the shank upper portion 8, thereby pulling the insert 214 surface 374 away from the receiver surface 90 and thus releasing the polyaxial mechanism. At such time, the shank 4 may be articulated with respect to the receiver 10, and the desired friction fit returns between the retainer 12 and the shank surface 34, so that an adjustable, but non-floppy relationship still exists between the shank 4 and the receiver 10. If further disassembly if the assembly is desired, such is accomplished in reverse order to the procedure described previously herein for the assembly 1.

Figure 55:
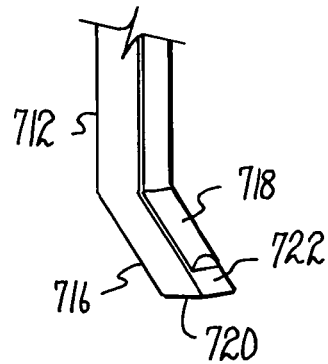
FIG. 55 is a partial perspective view of a portion of the locking tool of FIG. 54.
Figure 56:
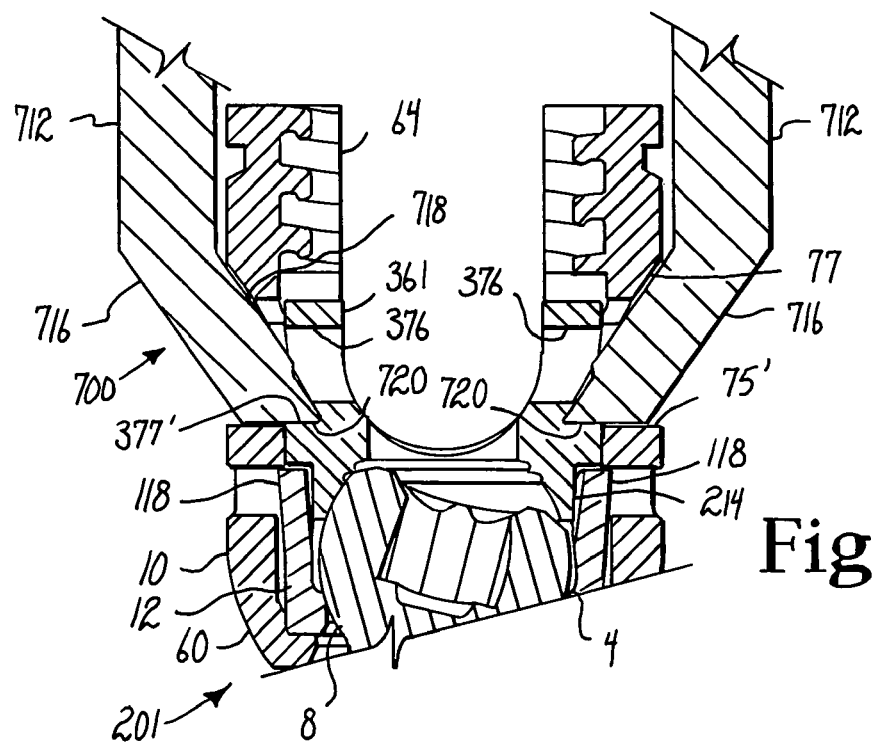
FIG. 56 is an enlarged and partial front elevational view of the assembly and locking tool of FIG. 54 with portions broken away to shown the detail thereof.

With reference to FIGS. 54-56, another manipulation tool, generally 700 is illustrated for independently locking the insert 214 to the receiver 10. The tool 700 includes a pair of opposed arms 712, each having an engagement extension 716 positioned at an angle with respect to the respective arm 712 such that when the tool is moved downwardly toward the receiver, one or more inner surfaces 718 of the engagement extension 716 slide along the surfaces 77 of the receiver and 377 of the insert 214 to engage the insert 214, with a surface 720 pressing downwardly on the insert surfaces 377', pushing the cylindrical surfaces 374 into an interference locking fit within the receiver surfaces 90. As shown in FIG. 56, when the insert 214 is locked against the receiver 10, the tool bottom surfaces 720 do not bottom out on the receiver surfaces 75', but remained spaced therefrom. In the illustrated embodiment, the surface 718 is slightly rounded and each arm extension 716 further includes a planar lower surface 722 that creates an edge with the bottom surface 720 for insertion and gripping of the insert 214 at the juncture of the surface 377 and the surface 377'. The tool 700 may include a variety of holding and pushing/pulling mechanisms, such as a pistol grip tool, that may include a ratchet feature, a hinged tool, or, a rotatably threaded device, for example.

Figure 57:
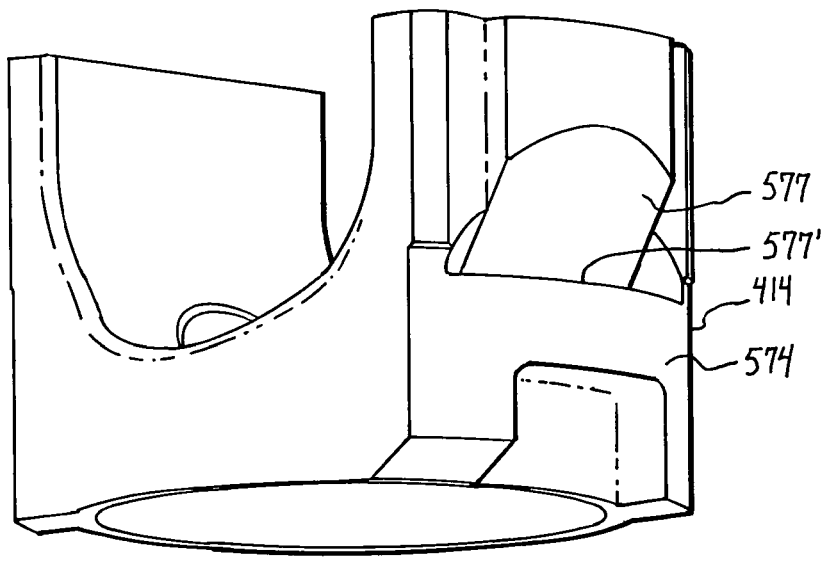
FIG. 57 is an enlarged perspective view of another alternative and non-locking insert for use with the assembly of FIG. 1 in lieu of the insert shown in FIG. 1.

With reference to FIGS. 57 and 58, another alternative non-locking insert 414 according to the invention is shown. The insert 414 may be used in lieu of either the insert 14 or the insert 214 with the shank 4, receiver 10, retainer 12, rod 21 and closure top 18 previously described herein. The insert 414 is assembled with the shank 4, receiver 10, retainer 12, rod 21 and closure top 18 as previously discussed with respect to the assembly 1. In FIG. 58, the resulting assembly that includes the insert 414 is identified as an assembly 401.

The insert 414 is identical to the insert 214 with two exceptions: the insert 414 does not include the tool receiving holes or through bores 376 of the insert 214 and the insert 414 has a lower outer arm surface 574 that is similar in form to the surface 374 of the insert 214, but is sized smaller for a sliding, non-locking fit within the receiver cylindrical surface 90. The insert 414 does however include a v-notch or sloping aperture with a sloping surface 577 and a planar base surface 577' that is the same or substantially similar to the aperture with the respective sloping surface 377 and base surface 377' of the insert 214. All other features of the insert 414 are identical or substantially similar to the insert 214.

With reference to FIG. 58, the assembly 401 that includes the insert 414 is shown with the locking tool 700 previously described herein. The locking tool 700 presses against the surfaces 577 and 577' of the v-notches of the insert 414 to place a temporary, locking force on the shank head 8 that temporarily locks the shank 4 into position with respect to the receiver 10, allowing a surgeon to manipulate the assembly 401 as if it were a mono-axial or fixed screw as long as the tool 700 presses inwardly and downwardly on the receiver 10 and the insert 414. However, also advantageously, when the surgeon no longer requires such rigid and fixed connection between the shank 4 and the receiver 10, the tool 700 may be removed and a non-floppy, but movable friction fit relationship returns between the shank 4 and the receiver 10 due to the frictional engagement of the retainer 12 flex tabs or fingers and the shank head 8 surface 34.

With reference to FIGS. 59-92 the reference number 1001 generally represents another alternative polyaxial bone screw apparatus or assembly according to the present invention. The assembly 1001 includes a shank 1004, that further includes a body 1006 integral with an upwardly extending upper portion or head structure 1008; a receiver 1010; a friction fit retainer 1012, and a compression or pressure insert 1014. The receiver 1010, retainer 1012 and compression insert 1014 are initially assembled and may be further assembled with the shank 1004 either prior or subsequent to implantation of the shank body 1006 into a vertebra 1017 (see FIG. 85), as will be described in greater detail below. FIGS. 59 and 89-92 further show a closure structure 1018 for capturing a longitudinal connecting member, for example, a rod 1021 which in turn engages the compression insert 1014 that presses against the shank upper portion 1008 into fixed frictional contact with the retainer 1012, so as to capture, and fix the longitudinal connecting member 1021 within the receiver 1010 and thus fix the member 1021 relative to the vertebra 1017. The illustrated rod 1021 is identical or substantially similar to the rod 21 previously described herein. Like the assembly 1 previously described herein, the receiver 1010 and the shank 1004 cooperate in such a manner that the receiver 1010 and the shank 1004 can be secured at any of a plurality of angles, articulations or rotational alignments relative to one another and within a selected range of angles both from side to side and from front to rear, to enable flexible or articulated engagement of the receiver 1010 with the shank 1004 until both are locked or fixed relative to each other near the end of an implantation procedure.

Figure 59:
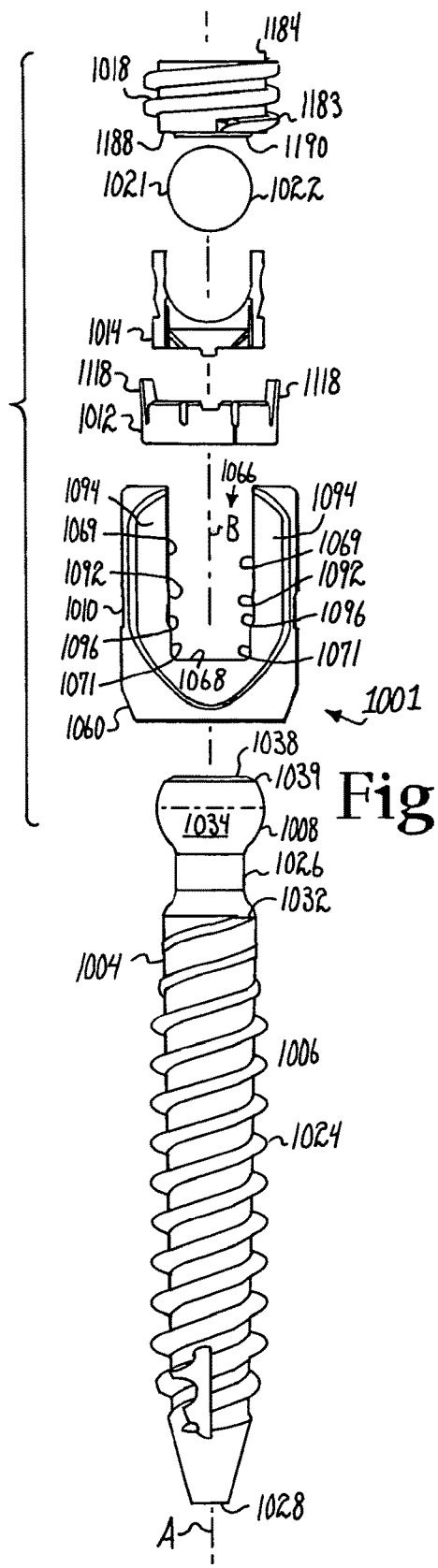
FIG. 59 is an exploded front elevational view of another polyaxial bone screw assembly according to the present invention including a shank, a receiver, an open friction fit expansion-only retainer and a lower compression insert, further shown with a portion of a longitudinal connecting member in the form of a rod and a closure top.
Figure 60:
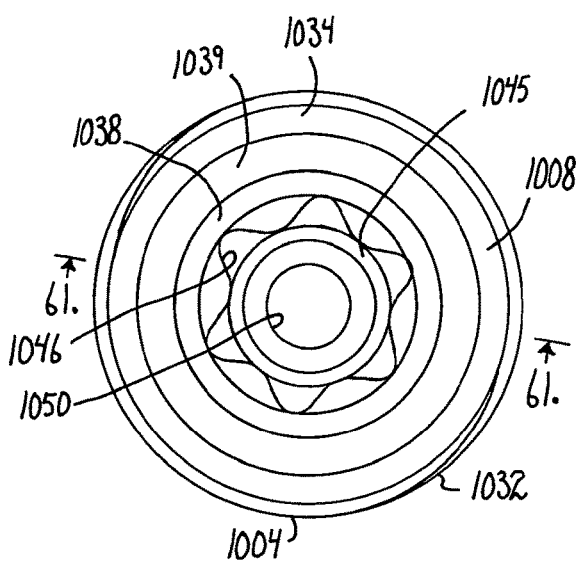
FIG. 60 is an enlarged top plan view of the shank of FIG. 59.
Figure 61:
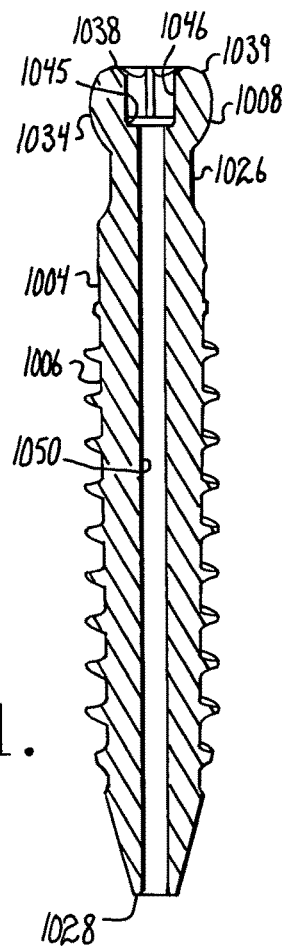
FIG. 61 is reduced cross-sectional view taken along the line 61-61 of FIG. 60.
Figure 62:
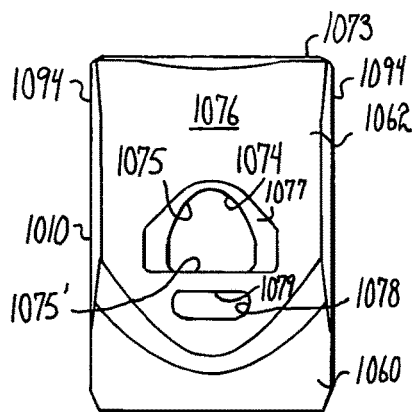
FIG. 62 is an enlarged side elevational view of the receiver of FIG. 59.

The shank 1004, best illustrated in FIGS. 59-61, is identical or substantially the same in form and function as the shank 4 previously described herein with respect to the assembly 1. Thus, the shank 1004 includes the shank body 1006, the head or upper portion 1008, a thread 1024 on the body 1006, a neck 1026, a bottom tip 1028, a shank top 1032 where the thread 1024 begins, a shank head spherical surface 1034, a top rim surface 1038, a frusto-conical surface 1039, a counter sunk base 1045 partially defining an internal drive feature or imprint 1046 and a small central cannulation bore 1050 that are the same or substantially similar to the respective the shank body 6, head or upper portion 8, thread 24, neck 26, tip 28, shank top 32, shank head spherical surface 34, top rim surface 38, frusto-conical surface 39, counter sunk base 45, internal drive feature 46 and cannulation bore 50 of the shank 4 of the assembly 1 previously described herein.

With particular reference to FIGS. 59 and 62-67, the receiver 1010 is substantially similar to the receiver 10 previously described herein, particularly with respect to inner surfaces that cooperate with the retainer 1012 that is substantially similar to the retainer 12, but there are some differences due to the fact that the receiver 1010 cooperates with the insert 1014 that is not a drop and rotate insert like the insert 14 of the assembly 1. Rather, the receiver 1010 includes surface features for receiving the retainer 1012 surfaces that extend through an upper channel of the receiver

1010 as will be described in greater detail below. The receiver 1010 has a generally U-shaped appearance with a partially discontinuous, partially faceted and partially curved outer profile and partially cylindrical inner and outer profiles. The receiver 1010 has an axis of rotation B that is shown in FIG. 59 as being aligned with and the same as an axis of rotation A of the shank 1004, such orientation being desirable, but not required during assembly of the receiver 1010 with the shank 1004. After the receiver 1010 is pivotally attached to the shank 1004, either before or after the shank 1004 is implanted in a vertebra 1017, the axis B is typically disposed at an angle with respect to the axis A, as shown, for example, in FIG. 104 with respect to the assembly 1001' that also includes the shank 1004 and the receiver 1010.

The receiver 1010 includes a curvate lower base portion 1060 defining a bore or inner cavity, generally 1061, the base 1060 being integral with a pair of opposed upstanding arms 1062 forming a cradle and defining a channel 1064 between the arms 1062 with an upper opening, generally 1066, and a substantially planar lower channel portion or seat 1068, the channel 1064 having a width for operably receiving the rod 1021 or portion of another longitudinal connector between the arms 1062, as well as closely receiving laterally extending portions of the insert 1014, the channel 1064 communicating with the base cavity 1061. Inner opposed substantially planar perimeter arm surfaces 1069 partially define the channel 1064 and are located on either side of each arm interior surface generally 1070. Lower opposed substantially planar and parallel surface portions 1071 of the arm surfaces 1069 terminate at the lower substantially planar seat 1068. The arm interior surfaces 1070, each include various inner cylindrical profiles, an upper one of which is a partial helically wound guide and advancement structure 1072 located adjacent top surfaces 1073 of each of the arms 1062. In the illustrated embodiment, the guide and advancement structure 1072 is a partial helically wound interlocking flangeform configured to mate under rotation with a similar structure on the closure structure 1018. However, it is foreseen that for certain embodiments of the invention, the guide and advancement structure 1072 could alternatively be a square-shaped thread, a buttress thread, a reverse angle thread or other thread-like or non-thread-like helically wound discontinuous advancement structures, for operably guiding under rotation and advancing the closure structure 1018 downward between the arms 1062, as well as eventual torquing when the closure structure 1018 abuts against the rod 1021 or other longitudinal connecting member. It is foreseen that the arms 1062 could have break-off extensions.

An opposed pair of upper rounded off triangular or delta-shaped tool receiving and engaging apertures 1074, each having a through bore formed by an upper arched surface 1075 and a substantially planar bottom surface 1075', are formed on outer surfaces 1076 of the arms 1062. Each through bore surface 1075 and 1075' extends through the arm inner surface 1070. The apertures 1074 with through bore portions 1075 and 1075' are sized and shaped for receiving portions of the retainer 1012 during top loading of the retainer from the receiver opening 1066 and into the base cavity 1061 as shown, for example, in FIG. 80. Each aperture 1074 further includes a sloping tool alignment surface 1077 that surrounds the arched bore portion 1075 and does not extend completely through the respective arm 1062. The sloping surface 1077 allows for an angled or sloping tool receiving interface running obliquely with respect to the receiver axis B. It is noted that the receiver 1010 is an integral structure and devoid of any spring tabs or collet-like structures. As will be discussed in greater detail below, the geometry of the insert 1014 that extends outwardly into the receiver channel 1065 at the perimeter arms surfaces 1069 prohibit the insert 1014 from rotating during assembly and thus misalignments with the receiver 1010 and the rod 1021 or other longitudinal connecting member that sometimes occurs with compression inserts does not occur in the assembly shown in FIG. 59. Two additional rectangular shaped through bores 1078 are also formed in the arms 1062 and are located directly below the apertures 1074. It is foreseen that the opening 1078 could assume almost any shape. The through bores 1078 are sized and shaped for receiving spring tab portions of the retainer 1012 during final assembly and operation, the bores 1078 capturing and retaining the retainer 1012 within the receiver as shown, for example, in FIG. 88. An upper surface 1079 defining each bore 1078 functions as an upper stop for a portion of the retainer 1012. Some or all of the apertures 1074 and 1078 and additional tool receiving apertures or grooves (not shown) may be used for holding the receiver 1010 during assembly with the insert 1014, the retainer 1012 and the shank 1004; during the implantation of the shank body 1006 into a vertebra when the shank is pre-assembled with the receiver 10; during assembly of the bone anchor assembly 1001 with the rod 1021 and the closure structure 1018; and during lock and release adjustment of some inserts according to the invention with respect to the receiver 1010, either into or out of frictional engagement with the inner surfaces of the receiver 1010 as will be described in greater detail below. It is foreseen that tool receiving grooves or apertures may be configured in a variety of shapes and sizes and be disposed at other locations on the receiver arms 1062.

Returning to the interior surface 1070 of the receiver arms 1062, located below the guide and advancement structure 1072 is a discontinuous cylindrical surface 1082 partially defining a run-out feature for the guide and advancement structure 1072. The cylindrical surface 1082 has a diameter equal to or slightly greater than a greater diameter of the guide and advancement structure 1072. Moving downwardly, in a direction toward the base 1060, following the cylindrical surface 1082 of each arm is a cylindrical surface (or, in some embodiments, a tapered surface) 1088 located below an annular run-out seat or surface 1085 that extends inwardly toward the axis B and runs perpendicular or somewhat obliquely towards the axis B. The surface 1088 has a diameter smaller than the diameter of the surface 1082. The surface 1088 is sized and shaped to initially closely receive a portion of the insert 1014. A discontinuous annular surface or narrow ledge 1089 is located below the surface 1088 and is substantially perpendicular to the axis B. A partially discontinuous cylindrical surface 1090 is located on each arm below and adjacent to the surface 1089. The surface 1090 has a diameter slightly smaller than the diameter of the surface 1088. It is noted that in some embodiments of the invention, the surfaces 1088 and 1090 are combined and form a single cylindrical surface.

The through bores 1075 of the apertures 1074 each extend through the arms at the surfaces 1082, 1088 and 1090 with the sloping tool engagement walls 1077 extending substantially on either side of each bore surface 1075 and formed in the arm outer surfaces 1076 at a location primarily opposite the inner surface 1088.

Figure 63:
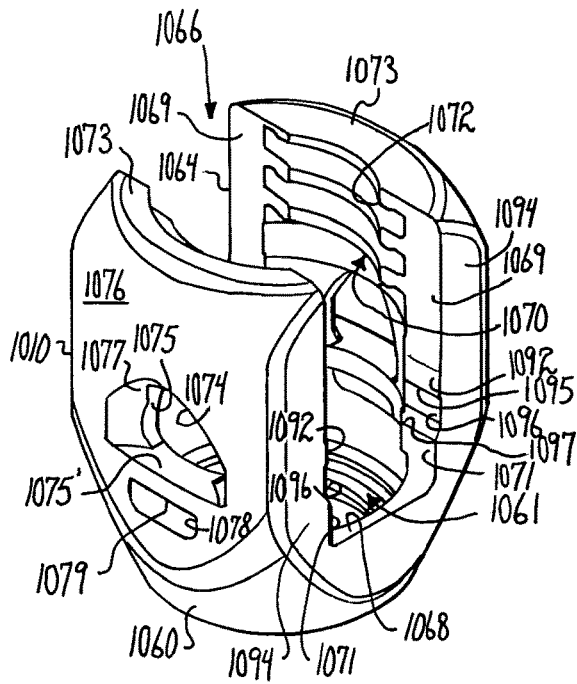
FIG. 63 is an enlarged perspective view of the receiver of FIG. 62.
Figure 64:
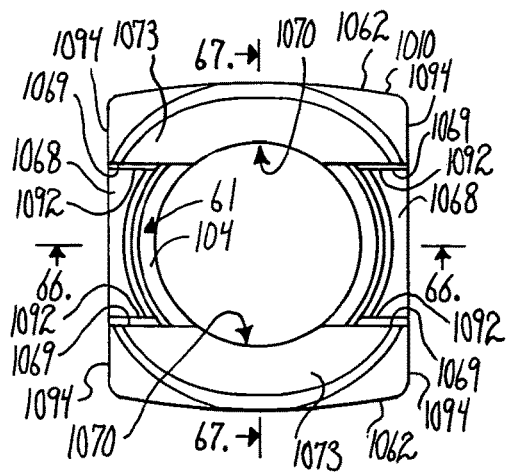
FIG. 64 is an enlarged top plan view of the receiver of FIG. 62.
Figure 65:
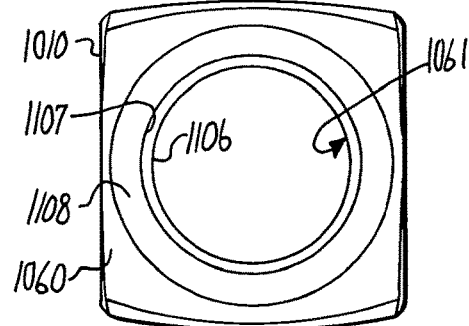
FIG. 65 is an enlarged bottom plan view of the receiver of FIG. 62.
Figure 66:
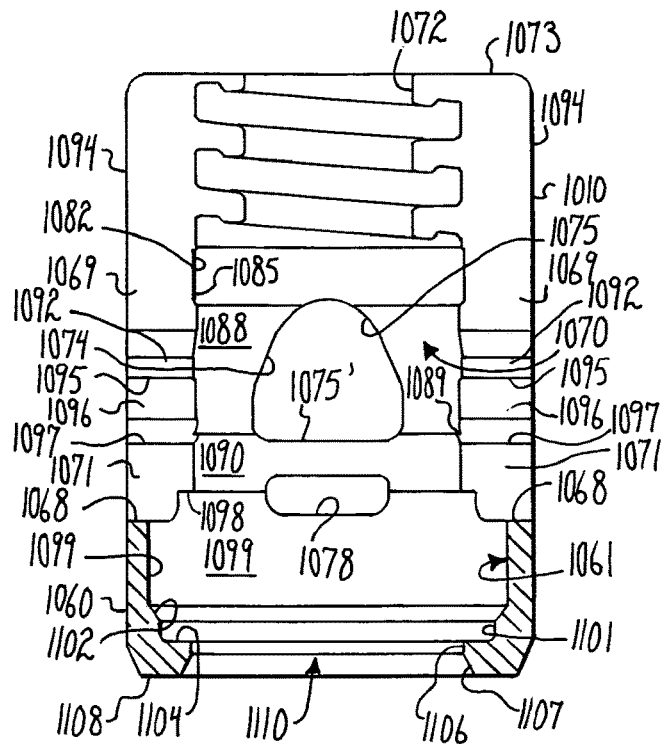
FIG. 66 is an enlarged cross-sectional view taken along the line 66-66 of FIG. 64.
Figure 67:
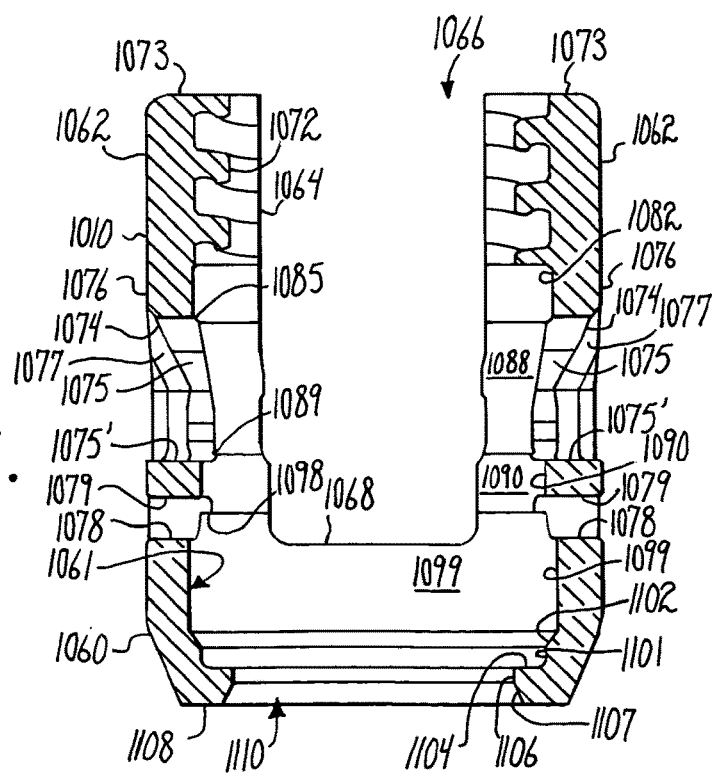
FIG. 67 is an enlarged cross-sectional view taken along the line 67-67 of FIG. 64.
Figure 68:
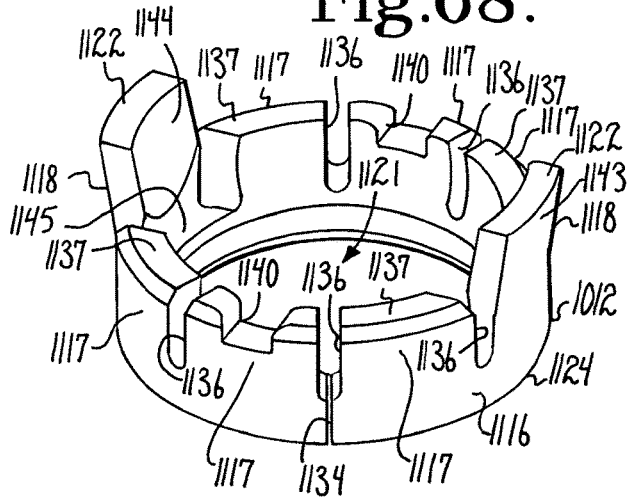
FIG. 68 is an enlarged perspective view of the retainer of FIG. 59.
Figure 69:
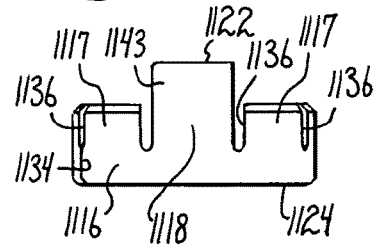
FIG. 69 is a reduced side elevational view of the retainer of FIG. 68.
Figure 70:
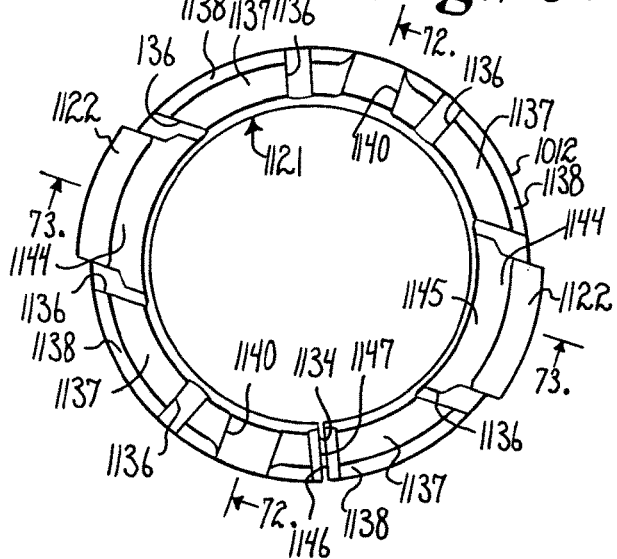
FIG. 70 is a top plan view of the retainer of FIG. 68.
Figure 71:
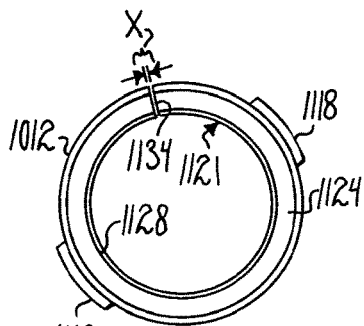
FIG. 71 is a reduced bottom plan view of the retainer of FIG. 68.
Figure 72:
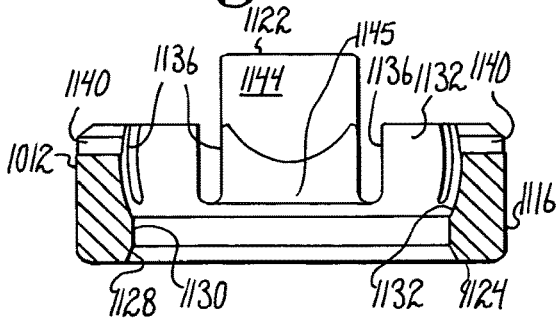
FIG. 72 is a cross-sectional view taken along the line 72-72 of FIG. 70.
Figure 73:
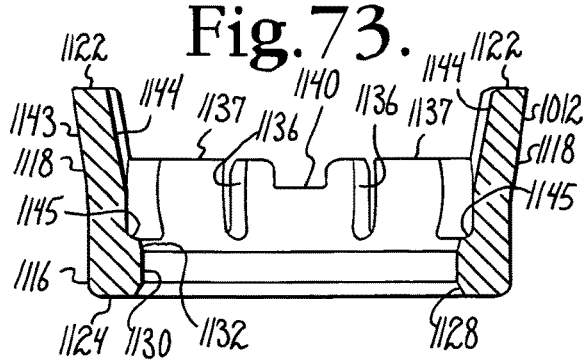
FIG. 73 is a cross-sectional view taken along the line 73-73 of FIG. 70.
Figure 74:
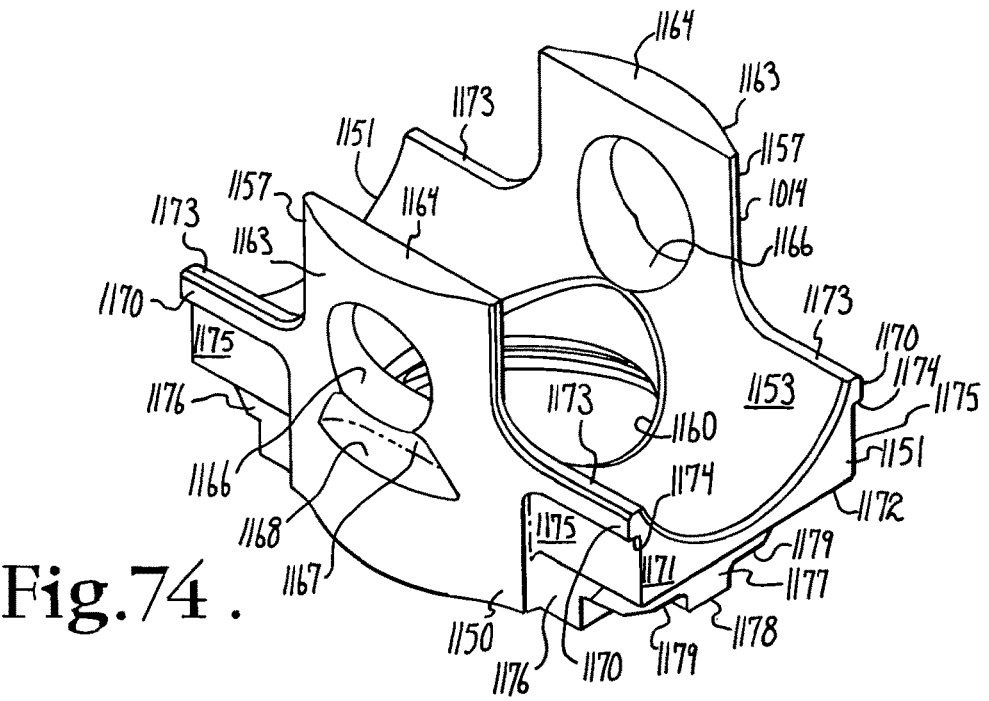
FIG. 74 is an enlarged perspective view of the insert of FIG. 59.
Figure 75:
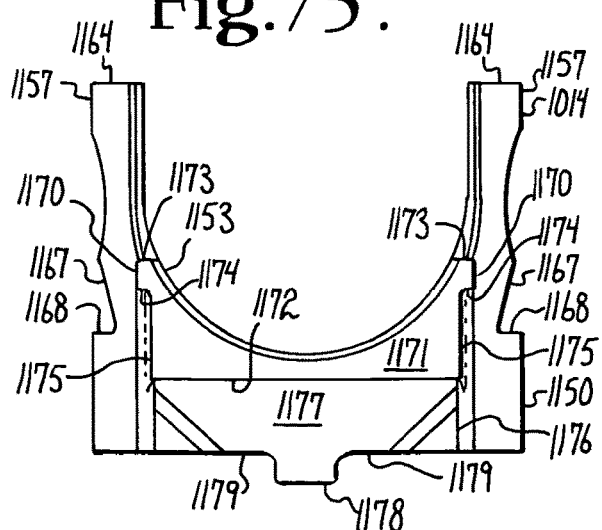
FIG. 75 is a front elevational view of the insert of FIG. 74.
Figure 76:
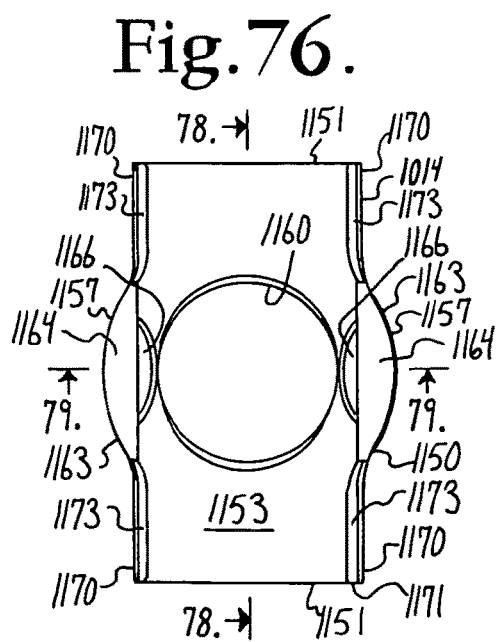
FIG. 76 is a top plan view of the insert of FIG. 74.

With particular reference to FIGS. 59, 63 and 64, returning to the substantially planar peripheral surfaces 1069, each arm 1062 includes a pair of projecting ridges or stops 1092, located on each surface 1069, for a total of four stops 1092 that are located near the annular surface 1085 and extend from front and back arm surfaces or faces 1094 to the cylindrical surface 1088. The stops 1092 of one arm 1062 directly face the opposing pair of stops 1092 on the other arm 1062, each stop 1092 projecting outwardly from the respective planar surface 1069. The illustrated stops 1092 are elongate and run in a direction perpendicular to the axis B. As will be described in greater detail below, the stops 1092 cooperate with surfaces of the insert 1014 to retain the insert 1014 within the channel 1064 of the receiver 1010. In the illustrated embodiment, each stop 1092 includes a bottom surface or ledge 1095 adjacent to a partially planar and partially curved surface 1096. A planar portion of the surface 1096 located directly beneath the stop 1092 is in line with or may be slightly inset from the surface 1069. Each set of opposed surfaces 1096 curve toward one another and terminate at the respective adjacent lower surface portions 1071. An edge 1097 defines a juncture of each curved surface 1096 and the respective adjacent lower surface portion 1071. A first width measured between opposing surface portions 1071 is smaller than a second width measured between opposed surfaces 1069 located between the stops 1092 and arm top surfaces 1073, providing opposed planar locking interference fit surfaces for the insert 1014' as will be described in greater detail below. The insert 1014 is sized and shaped to be closely received but slidable between the surfaces 1071.

Figure 88:
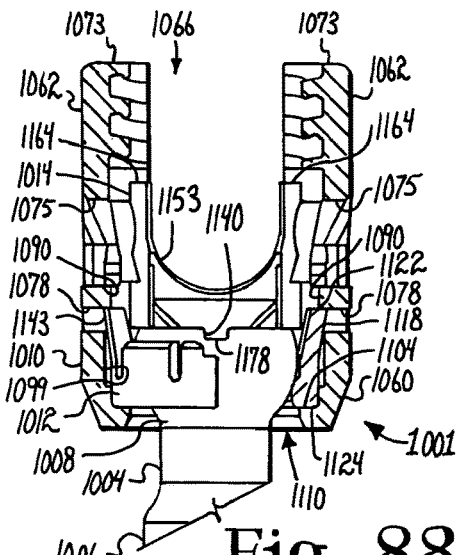
FIG. 88 is a partial front elevational view with portions broken away, similar to FIG. 87, the shank upper portion with attached retainer being shown pulled down into a seated position within the lower receiver cavity, the retainer spring tabs in a substantially neutral state, extending outwardly partially into receiver apertures.

Returning to FIGS. 66 and 67, an annular surface 1098 partially defines the base cavity 1061 and is located below and adjacent to the cylindrical surface 1090. The surface 1098 is disposed substantially perpendicular to the axis B, but could be oblique. Another cylindrical surface 1099 is located below and adjacent to the surface 1098. The surface 1099 also defines an upper cylindrical surface of the base cavity 1061. The cylindrical surface 1099 is oriented substantially parallel to the axis B and is sized and shaped to receive an expanded portion of the retainer 1012. The surfaces 1098 and 1099 define a circumferential recess that is sized and shaped to receive the retainer 1012 as it expands around the shank upper portion 1008 as the shank 1008 moves upwardly through the receiver base and toward the channel 1064 during assembly. It is foreseen that the recess could be tapered or conical in configuration. A cylindrical surface 1101 located below the cylindrical surface 1099 is sized and shaped to closely receive and surround a lower portion of the retainer 1012 when the retainer is in a substantially neutral position as shown in FIG. 88, for example. Thus, the cylindrical surface 1101 has a diameter smaller than the diameter of the cylindrical surface 1099 that defines the expansion area or expansion chamber for the retainer 1012. The surface 1101 is joined or connected to the surface 1099 by one or more beveled, curved or conical surfaces 1102. The surfaces 1102 allow for sliding and neutral or nominal positioning of the retainer 1012 into the space defined by the surface 1101 and ultimate seating of the retainer 1012 on a lower substantially horizontal annular surface 1104 located below and adjacent to the cylindrical surface 1101.

Located below and adjacent to the annular seating surface 1104 is another substantially cylindrical surface 1106 that communicates with a beveled or flared bottom opening surface 1107, the surface 1107 communicating with an exterior base surface 1108 of the base 1060, defining a lower opening, generally 1110, into the base cavity 1061 of the receiver 1010.

Figure 95:
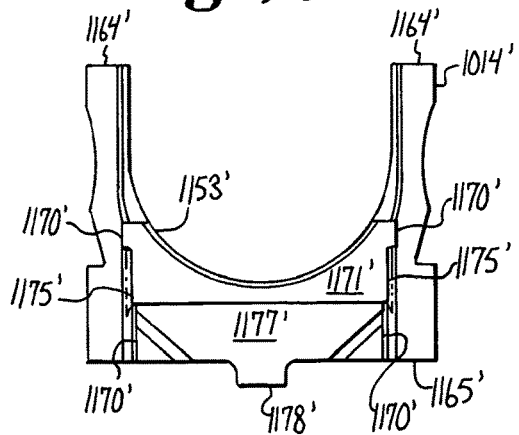
FIG. 95 is a front elevational view of the insert of FIG. 93.

With particular reference to FIGS. 59 and 68-73, the lower open or split friction fit retainer 1012, that operates to capture the shank upper portion 1008 within the receiver 1010, has a central axis that is operationally the same as the axis B associated with the receiver 1010 when the shank upper portion 1008 and the retainer 1012 are installed within the receiver 1010. The retainer 1012 includes a substantially cylindrical discontinuous lower body 1116, a plurality of flex fingers or panels, 1117 extending upwardly from the body 1116 and a pair of opposed spring arms or tabs 1118, also extending upwardly from the body 1116. The retainer ring 12 is made from a resilient material, such as a stainless steel or titanium alloy, so that the retainer 1012 body 1116 may be expanded and the fingers and tabs (1117 and 1118) of the retainer may be manipulated during various steps of assembly as will be described in greater detail below. The retainer 1012 has a central channel or hollow through bore, generally 1121, that passes entirely through the retainer 1012 from tab 1118 top surfaces 1122 to a bottom surface 1124 of the retainer body 1116. Surfaces that define the channel or bore 1121 at the body 1116 include an inner lower frusto-conical surface 1128 adjacent to the retainer body bottom surface 1124, a substantially cylindrical surface 1130 adjacent the frusto-conical surface 128 and a partially continuous partially discontinuous substantially radiused or spherical surface 1132 located adjacent the cylindrical surface 1130, the surface 1132 being substantially continuous near the surface 1130 and at each of the spring tabs 1118 and otherwise broken by a through slot or slit, generally 1134 and a plurality of evenly spaced partial slots or grooves 1136. The grooves 1136 separate the surface 1132 into a plurality of segments or pieces that have already been described herein as the flex fingers 1117. The grooves or slots 1136 run outwardly and upwardly from the retainer body 1116 through an upper surface 1137 of the retainer 1012 located between the spring tabs 1118. In the illustrated embodiment, the slots 1136 and the through slit 1134 form the six substantially uniform flex fingers or tabs 1117 as well as partially define the two spring tabs 1118, each finger 1117 having the inner spherical surface 1132 while each of the spring tabs 1118 extend outwardly and away from the surface 1132 at the retainer body 1116. It is foreseen that more or fewer flex fingers may be made by the forming of more or fewer slots 1136 and that the surface 1132 could be planar, tapered, faceted or otherwise curved. The illustrated discontinuous spherical surface 1132 is sized and shaped to closely fit about and snap onto the shank surface 1034 during assembly as will be described in greater detail below. Preferably the surface 1132 has a radius the same, slightly smaller or slightly larger than the radius of the spherical shank surface 1034. The surface 1132 could be bent or deformed inwardly or outwardly to better cooperate with the shank head. In operation, the discontinuous surface 1132 advantageously frictionally engages the bone screw shank upper portion or head 1008, allowing for an un-locked friction fit, non-floppy placement of the angle of the shank 1004 with respect to the receiver 1010 during surgery prior to locking of the shank 1004 with respect to the receiver 1010 near the end of the procedure. At the time of locking engagement, as shown in FIG. 95, for example, downward and outward force placed on the retainer 1012 by the shank upper portion 1008 expands the retainer body 1116 at the slit 1134 and the individual flex fingers 1117 no longer frictionally grip the spherical head surface 1034 of the upper portion 1008. To aid in bending flexibility and resiliency, some or all of the flex fingers 1117 may have sloping outer surfaces or other geometry to gain the level of resiliency desired for expansion and gripping of the fingers 1117 about the shank upper portion 1008. For example, the illustrated fingers 1117 each include an outer bevel 1138. The spherical surfaces 1132 may include a surface treatment or roughening to provide a desired friction fit. Again, it is noted that the surfaces 1132 need not be spherical and may be planar or include other surface geometries that resiliently grip the shank upper portion or head 1008. Again, in some embodiments, the flexible tabs 1117 may be bent or deformed to further enhance frictional engagement. It is noted that the fingers 1117 that are directed generally upwardly toward the receiver channel 1064 advantageously sufficiently snap about and then grip the shank surface 1034 to an extent to provide the friction fit desired for non-floppy placement of the shank body 1006 at a desired angle with respect to the receiver 1010 during manipulation of the bone screws 1001 and the rod 1021 or other longitudinal connecting member during surgery. However, as compared to bone screw inserts such as collets known in the art that include downwardly directed portions or panels that are ultimately wedged between a receiver surface and a shank surface upon final locking of the shank to the receiver, the thin upwardly directed fingers 1117 that extend away from the shank locking surface that are not as strong as the retainer body 1116 or the insert 1114, do not participate or cooperate with the final locking of the insert 1114 to the shank upper portion 1008, the shank upper portion 8 to the retainer 1012, and the retainer 1012 to the receiver inner and substantially planar surfaces 1101 and 1104. For such purpose, the more substantial retainer body 1116 located below the slots 1136 having only the very narrow slit 1134, used for expansion purposes only, is the component or portion that locks the shank upper portion 1008 between the receiver 1010, the insert 1114 and the rod 1021 or other longitudinal connecting member.

The retainer body 1116 and the flex fingers 1117 have an outer substantially cylindrical profile, sized and shaped to closely and slidingly fit within the receiver cavity 1061. Opposed flex fingers 1117 located centrally between the spring tabs 1118, each include a small groove 1140 sized and shaped to receive a portion of the insert 1014 as will be described in greater detail below.

The opposed pair of spring tabs 1118, extend outwardly away from one another and thus outwardly from the body 1116. Each spring tab 1118 is sized and shaped to closely cooperate and frictionally engage upper surfaces 1079 defining the receiver through bores 1078. An outer surface 1143 of each spring tab 1118 located adjacent each upper surface 1122 is sized and shaped to cooperate with and frictionally engage the cylindrical surface 1090 during assembly and shipping as shown, for example, in FIG. 83. In some embodiments of the invention, the tab 1118 surface 1143 may include one or more projections, grooves or notches as needed for tooling to resiliently hold the retainer in an upper portion of the cavity 1061 when desired, but readily release the retainer 1012 into a lower portion of the receiver cavity 1061 once the retainer flex tabs 1117 engage the shank head 1008. The illustrated spring tabs 1118 each include one or more planar or curved concave inner surfaces 1144 running from the top surface 1122 to a tab base seat, surface or surfaces 1145 located adjacent to and running laterally outwardly from the surface 1132. The surfaces 1144 extend both outwardly and upwardly from the base seat surfaces 1145. It is foreseen that in other embodiments of the invention, fewer or greater number of planar or other surfaces with other geometries may extend between the top surface 1122 and the inner surfaces defining the body 1116 of the retainer 1012.

The through slit 1134 of the resilient retainer 1012 is defined by first and second end surfaces, 1146 and 1147 disposed in spaced relation to one another (they may also be touching) when the retainer is in a neutral state. Both end surfaces 1146 and 1147 are disposed substantially perpendicular to the bottom surface 1124. A width X between the surfaces 1146 and 1147 is very narrow (slit may be made by EDM process) to provide stability to the retainer 1012 during operation. Because the retainer 1012 is top loadable in a neutral state and the retainer 1012 does not need to be compressed to fit within the receiver cavity 1061, the width X may be much smaller than might be required for a bottom loaded compressible retainer ring. The gap X functions only in expansion to allow the retainer 1012 to expand about the shank upper portion 1008. This results in a stronger retainer that provides more surface contact with the shank upper portion 1008 upon locking, resulting in a sturdier connection with less likelihood of failure than a retainer ring having a greater gap. Furthermore, because the retainer 1012 body 1116 is only expanded and never compressed inwardly, the retainer 1012 does not undergo the mechanical stress that typically is placed on spring ring type retainers known in the prior art that are both compressed inwardly and expanded outwardly during assembly.

It is foreseen that in some embodiments of the invention, the retainer 1012 inner surfaces may include a roughening or additional material to increase the friction fit against the shank upper portion 1008 prior to lock down by the rod 1021 or other longitudinal connecting member. Also, the embodiment shown in FIGS. 68-73 illustrates the surfaces 1146 and 1147 as substantially parallel to the central axis of the retainer, however, it is foreseen that it may be desirable to orient the surfaces obliquely or at a slight angle.

Figure 93:
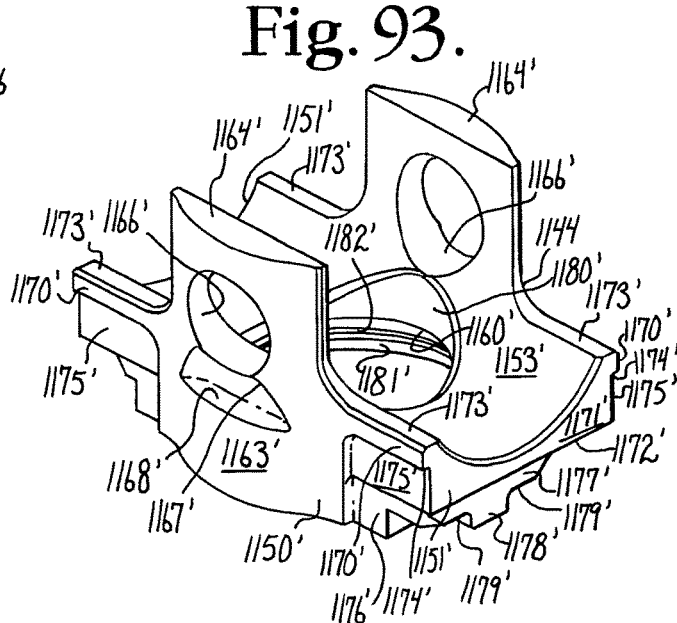
FIG. 93 is an enlarged perspective view of an alternative locking insert for use with the assembly of FIG. 59 in lieu of the insert shown in FIG. 59.
Figure 94:
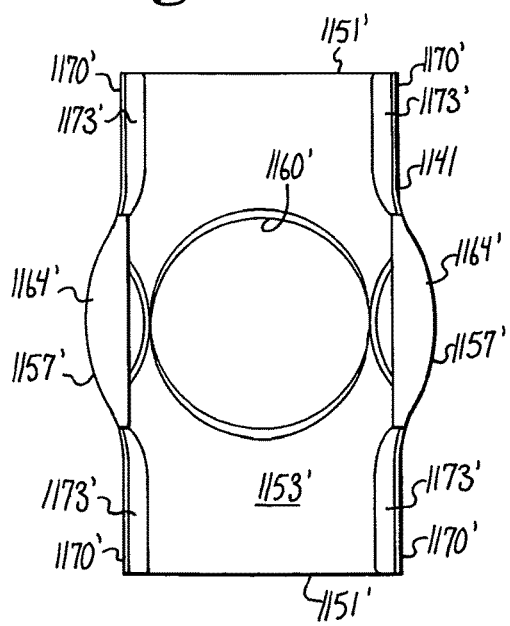
FIG. 94 is a top plan view of the insert of FIG. 93.

With particular reference to FIGS. 59 and 74-79, the compression insert 1014 is illustrated that is sized and shaped to be received by and down-loaded into the receiver 1010 at the upper opening 1066. The compression insert 1014 has an operational central axis that is the same as the central axis B of the receiver 1010. In operation, the insert advantageously frictionally engages the bone screw shank upper portion 1008. As will be described in greater detail below with respect to the insert 1014' illustrated in FIGS. 93-95, in some embodiments of the invention, the insert that has locked the shank 1004 in a desired angular position with respect to the receiver 1010, by, for example, compression from the rod 1021 and closure top 1018, is also forced into an interference fit engagement with the receiver 1010 at the pair of opposed planar arm surfaces 1071 thereof and thus is capable of retaining the shank 1006 in a locked position even if the rod 1021 and closure top 1018 are removed. Such locked position may also be released by the surgeon if desired. The non-locking insert 1014 as well as the locking insert 1014' are preferably made from a solid resilient material, such as a stainless steel or titanium alloy, so that portions of the insert may be pinched or pressed against and un-wedged from the receiver 1010 with a release tool.

The non-locking compression insert 1014 includes a substantially U-shaped body 1150 having opposed ends, generally 1151, the body 1150 being sized and shaped to extend completely through the U-shaped channel 1064 between the opposed front and back surfaces or faces 1094 of the arms 1062 so as to cooperate with the receiver arm side surfaces 1069, the stops 1092, the surfaces 1096 and 1071 below the stops 1092 and the channel seat 1068. A U-shaped channel surface or saddle 1153 formed in the body 1150 also extends between the insert ends 1151 and when the insert 1014 is assembled with the receiver 1010, the saddle 1153 substantially aligns with the receiver channel 1064. The saddle 1153 is formed by the insert body 1150 and by two upstanding arms 1157 and is sized and shaped to closely receive the rod 1021 or other longitudinal connecting member. It is foreseen that an alternative insert embodiment may be configured to include planar holding surfaces that closely hold a square or rectangular bar as well as hold a cylindrical rod-shaped, cord, or sleeved cord longitudinal connecting member. A bore, generally 1160, is disposed primarily within and through the insert body 1150 that runs along the axis B and communicates with the U-shaped channel formed by the saddle 1153 and upstanding arms 1157. The bore 1160 is sized and shaped to provide space and clearance for shank driving and other manipulation tools.

The arms 1157 that are disposed on either side of the saddle 1153 extend upwardly therefrom and are sized and configured for ultimate placement above the retainer spring tabs 1118 and beneath and spaced from the closure top 1118 within the cylindrical run-out surface 1082 located below the receiver guide and advancement structure 1072. The arms 1157 include outer curved, convex surfaces 1163 that are illustrated as partially cylindrical, and planar top surfaces 1164 that are ultimately positioned in spaced relation with the closure top 1018, so that the closure top 1018 frictionally engages the rod 1021 only, pressing the rod 1021 downwardly against the insert saddle 1153, the shank 1004 upper portion 1008 then pressing against the retainer 1012 to lock the polyaxial mechanism of the bone screw assembly 1001 at a desired angle. The partially cylindrical surface 1163 extends from each top surface 1164 to a substantially annular bottom surface 1165 of the insert 1014. The surface 1163 is sized and shaped to generally fit within the receiver arms 1062 and also within the opposed retainer spring tab inner surfaces 1144. It is foreseen that in some embodiments of the invention, the arms 1157 may be extended and the closure top configured such that the arms and, more specifically, the surfaces 1164 ultimately directly engage the closure top 1018 for locking of the polyaxial mechanism, for example, when the rod 1021 is made from a deformable material. The arm outer surfaces 1163 further include notches or grooves formed thereon for receiving manipulation, unlocking and locking tools. In the illustrated embodiments, each surface 1163 includes a through bore or hole 1166 for receiving tooling, such as that shown in FIG. 101, for example. Located below the through bore 1166 and formed in each surface 1163 is a v-notch or recess for receiving tooling, such as that shown in FIGS. 104 and 106, the notch defined by an upper sloping surface 1167 adjacent to the through bore 1166 and intersecting a lower planar surface 1168 disposed substantially perpendicular to a central axis of the insert 1014. Each through hole 1166, surfaces 1167 and surface 1168 cooperate and align with the respective receiver aperture through bore 1075, surface, and surface 1075' when the insert 1014 is captured and operationally positioned within the receiver 1010 as will be described in greater detail below. The insert outer arm surfaces 1163 are sized and shaped to be slidingly received by the surfaces 1144 of the retainer spring tabs 1118 during assembly and are spaced from the spring tabs 1118 after final locking of the assembly 1001.

The insert 1014 extends from the substantially cylindrical outer arms surfaces 1163 equally outwardly to each end 1151. Substantially planar outer side surfaces 1170 extend from each arm surface 1163 to a substantially planar surface 1171 disposed perpendicular thereto, the surfaces 1171 substantially defining each of the ends 1151. Each end surface 1171 is adjacent to a lower or base extension surface 1172 that runs parallel to the base surface 1165 and extends inwardly toward the insert body 1150. Adjacent to each side surface 1170 is a substantially planar upper or top surface 1173 running from one of the arms 1157 to each of the end surfaces 1171. Each of the surfaces 1170 form a narrow outer strip and are adjacent and perpendicular to a lower narrow ledge 1174. The ledges 1174 run parallel to the upper surfaces 1173. An inset planar surface 1175 is adjacent to each lower ledge surface 1174 and runs parallel to the respective outer planar side surface 1170. A width between opposing surfaces 1175 is sized such that the surfaces 1175 are slidingly received between the opposed receiver lower arm surfaces 1071. In other embodiments of the invention, a width between the surfaces 1175 may be enlarged such that the surfaces 1175 must be forced downwardly between the planar surfaces 1071 to provide a locking interference fit of the insert against the receiver and thus lock the polyaxial mechanism of the bone screw assembly as will be described below with respect to the insert 1014'. The surfaces 1175 terminate at the lower base extension surface 1172. Adjacent to the surface 1172 and located on either side of the insert body 1150 is a partial lower base body portion 1176 that extends outwardly from the generally cylindrical body 1150 of the insert 1014, but does not extend all the way to the insert end surfaces 1171. Each lower base body portion 1176 includes cut-outs, protrusions and tapers sized and shaped for close cooperation with the retainer 1012. For example, each base body portion 1176 is partially defined by a planar surface 1177 that runs parallel to the nearby surface 1171, the surface 1177 partially defining a protrusion 1178 that is sized and shaped to be slidingly received by and closely fit within one of the retainer grooves 1140. The protrusion 1178 extends below the insert substantially annular bottom surface 1165. The illustrated protrusion is substantially rectangular in profile to match the profile of the cooperating retainer groove 1150, but in other embodiments it may be of a different geometry to substantially match and fill the groove 1140. Further cut-outs, tapers or bevels may be made to the insert surfaces to provide adequate clearance and ease of manipulation of the insert 1014 within the receiver 1010 and retainer 1102, such as lower surfaces 1179 located on either side of the protrusion 1178 that are integral and flush with the bottom surface 1165 and are sized and located to seat on the retainer 1012 upper planar surface 1137.

The insert bore, generally 1160, is substantially defined at the body 1150 by an inner substantially cylindrical surface 1180 that communicates with the saddle 1153 and also communicates with a lower concave substantially spherical surface 1181 having a radius the same or substantially similar to a radius of the surface 1034 of the shank upper portion or head 1008. The surface 1181 primarily terminates at the base 1165, but also extends into and partially defines each of the lower protrusions 1178. Located along the spherical surface 1181 between the cylindrical surface 1180 and the annular base surface 1165 is a shank gripping surface portion 1182. The gripping surface portion 1182 includes one or more stepped surfaces or ridges sized and shaped to grip and penetrate into the shank head 1008 when the insert 1014 is locked against the head surface 1034. It is foreseen that the stepped surface portion 1182 may include grater or fewer number of stepped surfaces and cover greater or less surface area of the spherical surface 1181. It is foreseen that the shank gripping surface portion 1182 and also the spherical surface 1181 may additionally or alternatively include a roughened or textured surface or surface finish, or may be scored, knurled, or the like, for enhancing frictional engagement with the shank upper portion 1008.

The bore 1160 is sized and shaped to receive the driving tool (not shown) therethrough that engages the shank drive feature 1046 when the shank body 1006 is driven into bone with the receiver 1010 attached. Also, the bore 1160 may receive a manipulation tool used for releasing the alternative locking insert 1014' from a locked position with the receiver, the tool pressing down on the shank and also gripping the insert 1014' at the opposed through bores 1166 or with other tool engaging features. A manipulation tool for un-wedging the insert 1014' from the receiver 1010 may also access the bores 1166 from the receiver through bores 1074. The illustrated insert 1014 may further include other features, including grooves and recesses for manipulating and holding the insert 1014 within the receiver 1010 and providing adequate clearance between the retainer 1012 and the insert 1014. It is foreseen that insert 1014 does not require bores 1166 in some embodiments.

With reference to FIGS. 59 and 89-92, the illustrated elongate rod or longitudinal connecting member 1021 (of which only a portion has been shown) is identical or substantially similar to the rod 21 previously described herein with respect to the assembly 1.

Longitudinal connecting members for use with the assembly 1001 may take a variety of shapes, including but not limited to rods or bars of oval, rectangular or other curved or polygonal cross-section. The shape of the insert 1014 may be modified so as to closely hold the particular longitudinal connecting member used in the assembly 1001. Some embodiments of the assembly 1001 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 1014 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1001, for example. A damping component or bumper may be attached to the longitudinal connecting member at one or both sides of the bone screw assembly 1001. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 59 and 89-92, the closure structure or closure top 1018 shown with the assembly 1001 is substantially similar to the closure top 18 previously described herein with respect to the assembly 1. Thus, the closure top 1018 includes an outer helically wound guide and advancement structure 1183, a top surface 1184, an internal drive 1186, a base or bottom surface 1188, and a rim 1190 that are substantially similar in form and function to the respective guide and advancement structure 182, top surface 184, internal drive 186, base or bottom surface 188 and rim 190 of the closure top 18 previously described herein. It is noted that in some embodiments, the closure top bottom surface 1188 may include a central point and in other embodiments need not include a point and/or the rim. The closure top 1018 may further include a cannulation through bore (not shown) extending along a central axis thereof and through the top and bottom surfaces thereof. Such a through bore provides a passage through the closure 1018 interior for a length of wire (not shown) inserted therein to provide a guide for insertion of the closure top into the receiver arms 1062.

Figure 99:
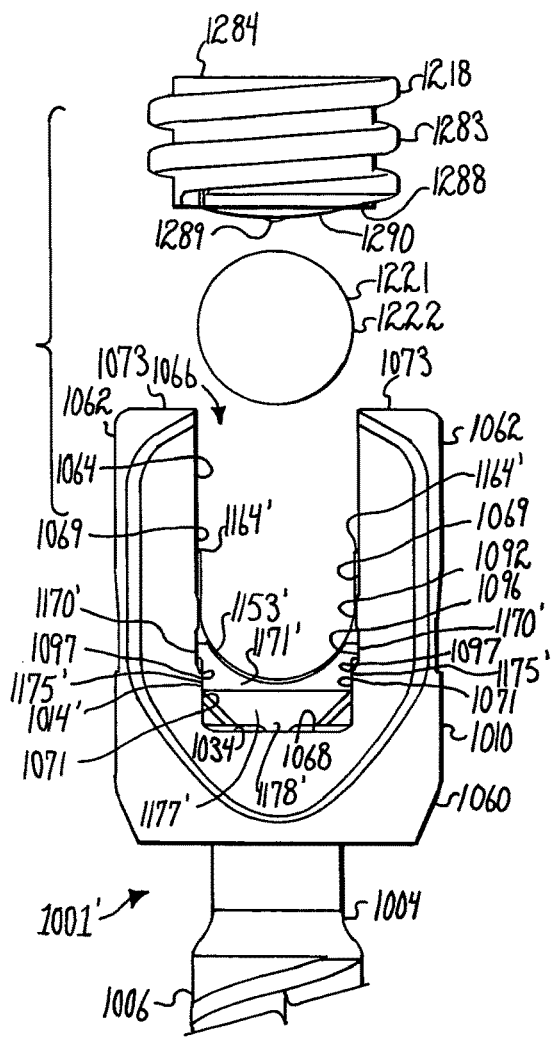
FIG. 99 is an enlarged and partial front elevational view with portions broken away, similar to FIG. 98, showing the shank, retainer, insert and receiver remaining in a locked position after removal of the rod and closure top of FIG. 59 and further showing, in exploded view, an alternative deformable rod and cooperating alternative closure top.
Figure 100:
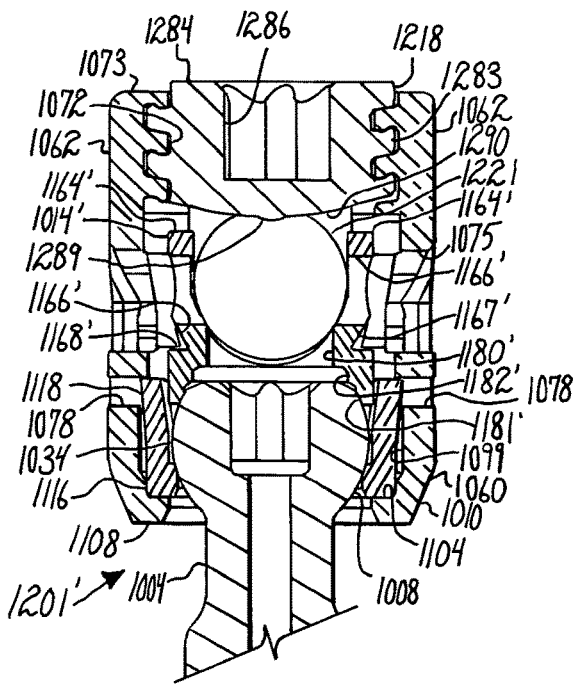
FIG. 100 is a partial front elevational view with portions broken away, similar to FIG. 99, showing the alternative rod and closure top fixed to the remainder of the assembly.

An alternative closure top 1218 for use with a deformable rod, such as a PEEK rod 1221, is shown in FIGS. 99 and 100. The top 1218 is identical to the top 1018 with the exception that a point or nub 1289 is located on a domed surface 1290 in lieu of the rim of the closure top 1018. The closure top 1218 otherwise includes a guide and advancement structure 1283, a top 1284, an internal drive 1286 and a bottom outer annular surface 1288 that same or substantially similar to the guide and advancement structure 1183, top 1184, internal drive 1186 and a bottom surface 1188 described herein with respect to the closure top 1018. In some embodiments, the internal drive 1286 is not as large as the drive 1186 of the closure top 1018, such smaller drive providing for less force being placed on a deformable rod, for example, and not being required when a locking insert, for example, the insert 1014' discussed below is utilized in a bone screw assembly of the invention.

Returning to the assembly 1001, preferably, the receiver 1010, the retainer 1012 and the compression insert 1014 are assembled at a factory setting that includes tooling for holding and alignment of the component pieces and pinching or compressing of the retainer 1012 spring tabs 1118, if necessary and otherwise manipulating the retainer 1012 and insert 1014 with respect to the receiver 1010. In some circumstances, the shank 1004 is also assembled with the receiver 1010, the retainer 1012 and the compression insert 1014 at the factory. In other instances, it is desirable to first implant the shank 1004, followed by addition of the pre-assembled receiver, retainer and compression insert at the insertion point. In this way, the surgeon may advantageously and more easily implant and manipulate the shanks 1004, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 1008 and/or hydroxyapatite on the shank 1006), with the receiver, retainer and compression insert. Allowing the surgeon to choose the appropriately sized or treated shank 1004 advantageously reduces inventory requirements, thus reducing overall cost and improving logistics and distribution.

Pre-assembly of the receiver 1010, retainer 1012 and compression insert 1014 is shown in FIGS. 80-84. With particular reference to FIG. 80, first the retainer 1012 is inserted into the upper receiver opening 1066, leading with one of the spring tabs 1118 with both of the spring tab top surfaces 1122 facing one arm 1062 and the retainer bottom surface 1124 facing the opposing arm 1062 (shown in phantom). The retainer 1012 is then lowered in such sideways manner into the channel 1064 and partially into the receiver cavity 1061, followed by tilting the retainer 1012 such that the top surface 1122 of the leading spring tab 1118 is moved into a nearby receiver arm aperture 1074 below the arched through bore surface 1075. With reference to FIGS. 80 and 81, the retainer 1012 is then further tilted or turned and manipulated within the receiver to a position within the cavity until the retainer 1012 bottom surface 1124 is directed toward the receiver cavity 1061 and the spring tab upper surfaces 1122 are facing upwardly toward the receiver channel opening 1066 as shown in FIGS. 81 and 82. To accomplish such tilting and turning of the retainer 1012, the spring tab arm 1118 located within the receiver bore surface 1075 is manipulated downwardly and then upwardly within such bore and finally shifted out of such bore when the opposed spring tab arm 1118 moves past and clears the guide and advancement structure 1072 of the receiver 1010. With further reference to FIG. 82 and also FIG. 83, the retainer 1012 is moved downwardly toward the receiver base 1060 and the spring tabs 1118 are pressed resiliently toward one another as the retainer spring tab outside surfaces 1143 abut against the receiver cylindrical surfaces 1090.

Also with reference to FIGS. 82 and 83, the insert 1014 is loaded into the receiver 1010 and may be used to push the retainer downwardly into the desired compressed shipping position shown in FIG. 83. The insert 1014 is loaded into the receiver through the opening 1066 as shown in phantom in FIG. 82 with the protrusions 1178 facing the receiver channel 1064. As the insert 1014 is lowered into the receiver, the side surfaces 1170 are slidingly received by the opposed receiver inner arm surfaces 1069 defining the channel 1064. Once the insert 1014 protrusion 1178 and surfaces 1179 make contact with the respective retainer groove 1140 and upper surfaces 1137 as shown in FIG. 82 with the insert lower body 1150 located between the spring tabs 1118, the insert 1014 may be pressed further downwardly until the insert 1014 is captured within the receiver 1010 as best shown in FIG. 84, with the saddle 1153 being slightly pinched or pressed to allow the opposed surfaces 1170 to engage and then move past the receiver stops 1092, the stops 1092 thereafter prohibiting upward movement of the insert 1014 out of the receiver channel 1064. Specifically, if the insert 1014 is moved upwardly toward the opening 1066 of the receiver, the insert surfaces 1173 abut against bottom surfaces 1095 of the stops 1092, prohibiting further upward movement of the insert 1014 unless a tool is used to pinch the surfaces 1170 toward one another while moving the insert 1014 upwardly toward the receiver opening 1066.

The insert 1014 and the retainer 1012 that is slightly spaced from the seating surface 1104 of the receiver 1010 and held in such position by the spring tabs 1118 resiliently pressing against the receiver inner cylindrical surfaces 1090 are now in a desired position for shipping as an assembly along with the separate shank 1004. The insert 1014 protrusions 1178 are seated within the retainer grooves 1140 prohibiting further downward movement of the insert 1014 and the insert 1014 is fully captured within the receiver 10 by the stops 1092, prohibiting further upward movement thereof.

Typically, the receiver and retainer combination are shipped or otherwise provided to the end user with the spring tabs 1118 wedged against the receiver as shown in FIG. 83. The receiver 1010, retainer 1012 and insert 1014 combination is now pre-assembled and ready for assembly with the shank 1004 either at the factory, by surgery staff prior to implantation, or directly upon an implanted shank 1004 as will be described herein.

Figure 85:
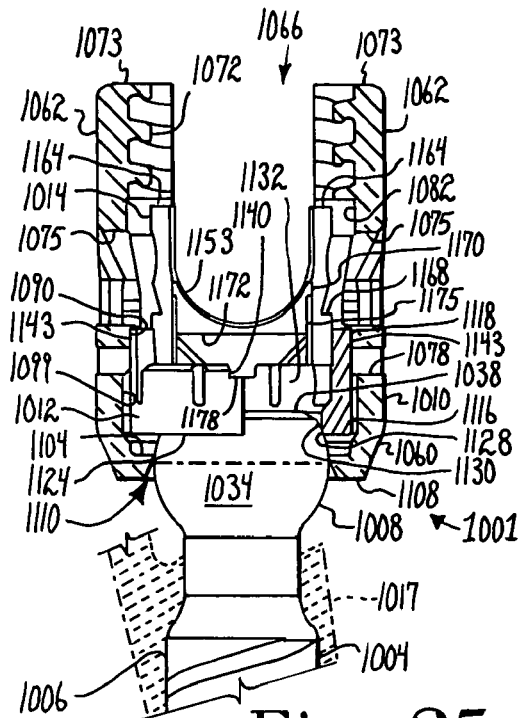
FIG. 85 is an enlarged front elevational view with portions broken away, similar to FIG. 83, and further showing an enlarged and partial shank of FIG. 59 in a first stage of assembly with the retainer, a hemisphere of the shank head and a vertebra portion both being shown in phantom.

As illustrated in FIG. 85, the bone screw shank 1004 or an entire assembly 1001 made up of the assembled shank 1004, receiver 1010, retainer 1012 and compression insert 1014, is screwed into a bone, such as the vertebra 1017 (shown in phantom), by rotation of the shank 1004 using a suitable driving tool (not shown) that operably drives and rotates the shank body 1006 by engagement thereof at the internal drive 1046. Specifically, the vertebra 1017 may be pre-drilled to minimize stressing the bone and have a guide wire (not shown) inserted therein to provide a guide for the placement and angle of the shank 1004 with respect to the vertebra. A further tap hole may be made using a tap with the guide wire as a guide. Then, the bone screw shank 1004 or the entire assembly 1001 is threaded onto the guide wire utilizing the cannulation bore 1050 by first threading the wire into the opening at the bottom 1028 and then out of the top opening at the drive feature 1046. The shank 1004 is then driven into the vertebra using the wire as a placement guide. It is foreseen that the shank and other bone screw assembly parts, the rod 1021 (also having a central lumen in some embodiments) and the closure top 1018 (also with a central bore) can be inserted in a percutaneous or minimally invasive surgical manner, utilizing guide wires and attachable tower tools mating with the receiver. When the shank 1004 is driven into the vertebra 1017 without the remainder of the assembly 1001, the shank 1004 may either be driven to a desired final location or may be driven to a location slightly above or proud to provide for ease in assembly with the pre-assembled receiver, compression insert and retainer.

Figure 86:
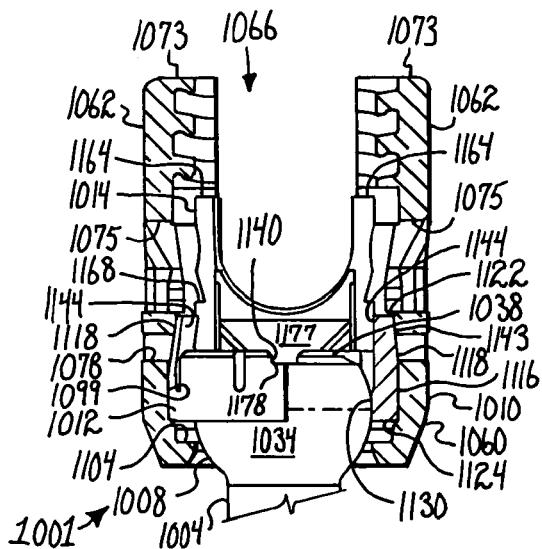
FIG. 86 is a partial front elevational view with portions broken away, similar to FIG. 85, showing the retainer lower portion in an expanded state about a mid-portion of the shank head, the head hemisphere shown in phantom.
Figure 87:
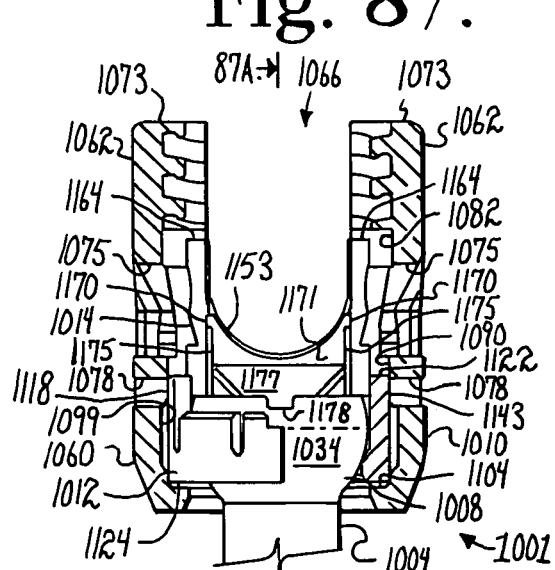
FIG. 87 is a reduced partial front elevational view with portions broken away, similar to FIG. 86, the shank upper portion or head in frictional engagement with an upper portion of the retainer.
Figure 87A:
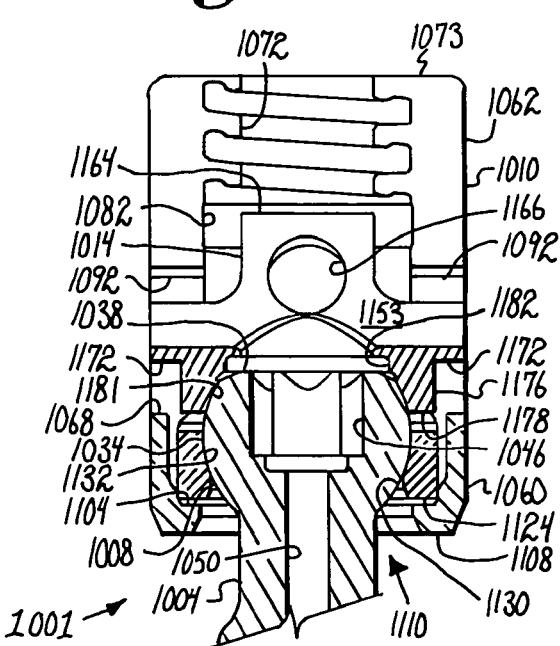
FIG. 87A is an enlarged cross-sectional view taken along the line 87A-87A of FIG. 87.

With further reference to FIG. 85, the pre-assembled receiver, insert and retainer are placed above the shank upper portion 1008 until the shank upper portion is received within the opening 1110. With particular reference to FIGS. 85-87A, as the shank upper portion 1008 is moved into the interior 1061 of the receiver base, the shank upper portion 1008 presses upwardly against the retainer 1012 in the recess partially defined by the cylindrical surface 1099. As the portion 1008 continues to move upwardly toward the channel 6104, the surface 1034 forces outward movement of the retainer 1012 towards the cylindrical surface 1099 defining the receiver expansion recess or chamber as shown in FIG. 86. With reference to FIG. 87, the retainer 1012 begins to return to its neutral state as the center of the sphere (shown in dotted lines) passes beyond the center of the retainer expansion recess. At this time also, the spherical surface 1034 moves into engagement with the surfaces 1132 of the retainer flex tabs 1117, the tabs 1117 expanding slightly outwardly to receive the surface 1034 as best shown in FIG. 87A. With further reference to both FIGS. 87 and 87A, the spherical surface 1034 then enters into full frictional engagement with the panel inner surfaces 1132. At this time, the retainer 1012 panels and the surface 1034 are in a fairly tight friction fit, the surface 1034 being pivotable with respect to the retainer 1012 with some force. Thus, a tight, non-floppy ball and socket joint is now created between the retainer 1012 and the shank upper portion 1008.

Figure 89:
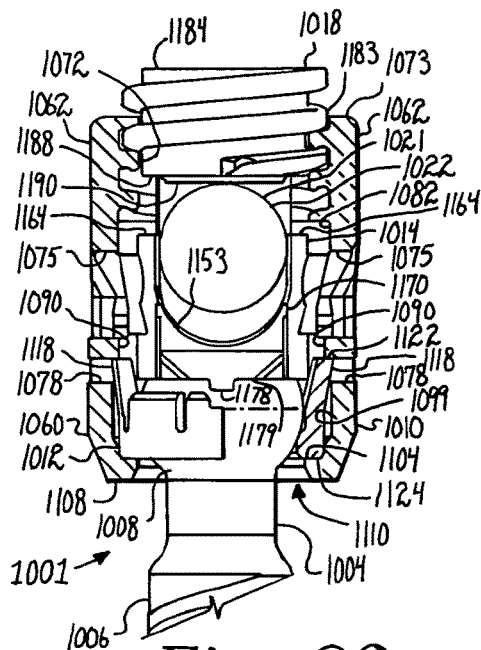
FIG. 89 is an enlarged and partial front elevational view with portions broken away of all of the components shown in FIG. 59, the assembly as in FIG. 88 being shown in a stage of assembly with the rod and closure top.
Figure 90:
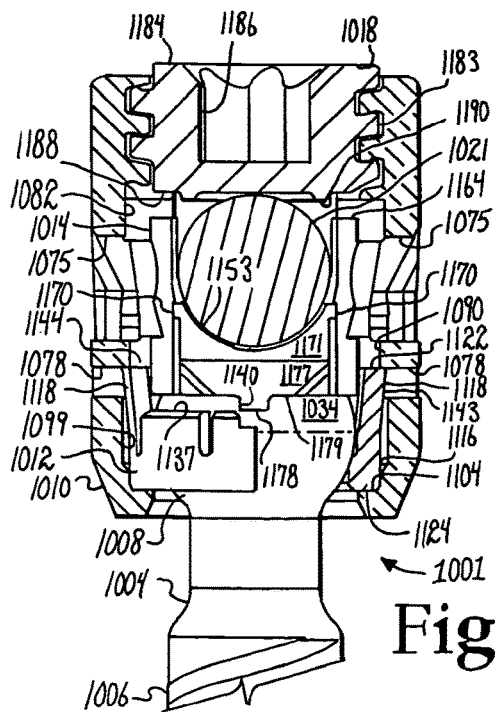
FIG. 90 is an enlarged and partial front elevational view with portions broken away, similar to FIG. 89, shown in a final locking position.
Figure 91:
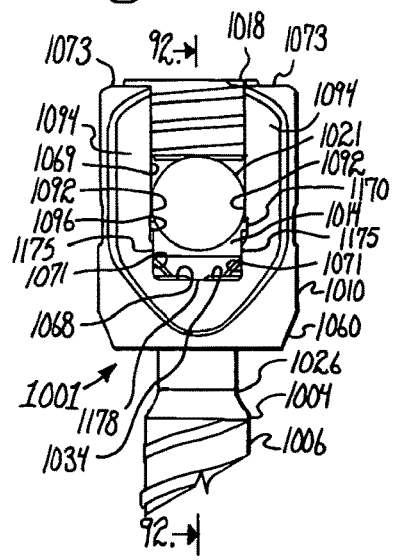
FIG. 91 is a reduced and partial front elevational view of the assembly of FIG. 90.
Figure 92:
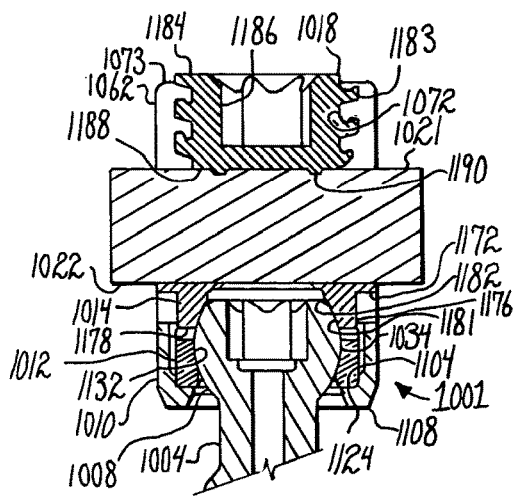
FIG. 92 is an enlarged cross-sectional view taken along the line 92-92 of FIG. 91.

With reference to FIG. 88, the receiver is then pulled upwardly or the shank 1004 and attached retainer 1012 are then moved downwardly into a desired position with the retainer seated on the surface 1104. Again, this may be accomplished by either an upward pull on the receiver 1010 or, in some cases, by driving the shank 1004 further into the vertebra 1017. At this time, the retainer spring tabs 1118 once against spring outwardly into the receiver bores 1078, making it impossible to move the retainer out of the locking portion of the chamber defined in part by the receiver seat 1104 unless pressed inwardly by a tool or tools via the through bores 1078. With reference to FIG. 89, the insert 1014 may be pressed downwardly by a tool or by the rod 1021 and the closure top 1018. Also, in some embodiments, when the receiver 1010 is pre-assembled with the shank 1004, the entire assembly 1001 may be implanted at this time by inserting the driving tool (not shown) into the receiver and the shank drive 1046 and rotating and driving the shank 1004 into a desired location of the vertebra 1017.

With reference to FIGS. 88 and 89 and also, for example, to FIG. 106 (that shows the use of the assembly 1001' which is an assembly 1001 with an alternative locking insert), at this time, the receiver 1010 and may be articulated to a desired angular position with respect to the shank 1004, such as that shown in FIG. 106, that will be held, but not locked, by the frictional engagement between the retainer 1012 and the shank upper portion 1008.

With reference to FIGS. 89-92, the rod 1021 is eventually positioned in an open or percutaneous manner in cooperation with the at least two bone screw assemblies 1001. The closure structure 1018 is then advanced between the arms 1062 of each of the receivers 1010. The closure structure 1018 is rotated, using a tool engaged with the inner drive 1186 until a selected pressure is reached at which point the rod 1021 engages the U-shaped seating surface 1153 of the compression insert 1014, pressing the insert spherical surface 1181 and stepped shank gripping surfaces 1182 against the shank spherical surface 1034, the edges of the stepped surfaces 1182 penetrating into the spherical surface 1034, pressing the shank upper portion 1008 into locked frictional engagement with the retainer 1012. Specifically, as the closure structure 1018 rotates and moves downwardly into the respective receiver 1010, the rim 1190 engages and penetrates the rod surface 1022, the closure structure 1018 pressing downwardly against and biasing the rod 1021 into compressive engagement with the insert 1014 that urges the shank upper portion 1008 toward the retainer 1012 inner body portion at least partially defined by the inner surface 1130 located below the friction fit panels 1132 and into locking engagement therewith, the retainer 1012 frictionally abutting the surface 1104 and expanding outwardly and abutting against the cylindrical surface 1101. For example, about 80 to about 120 inch pounds of torque on the closure top may be applied for fixing the bone screw shank 1006 with respect to the receiver 1010. If disassembly if the assembly 1001 is desired, such is accomplished in reverse order to the procedure described previously herein for assembly.

Figure 96:
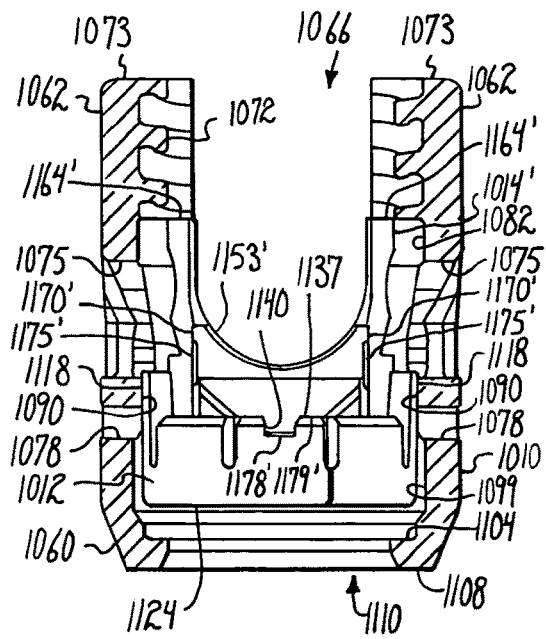
FIG. 96 is an enlarged front elevational view with portions broken away of the receiver and retainer of FIG. 59 and the insert of FIG. 93 in reduced front elevation, the assembly shown in an un-locked shipping position.
Figure 97:
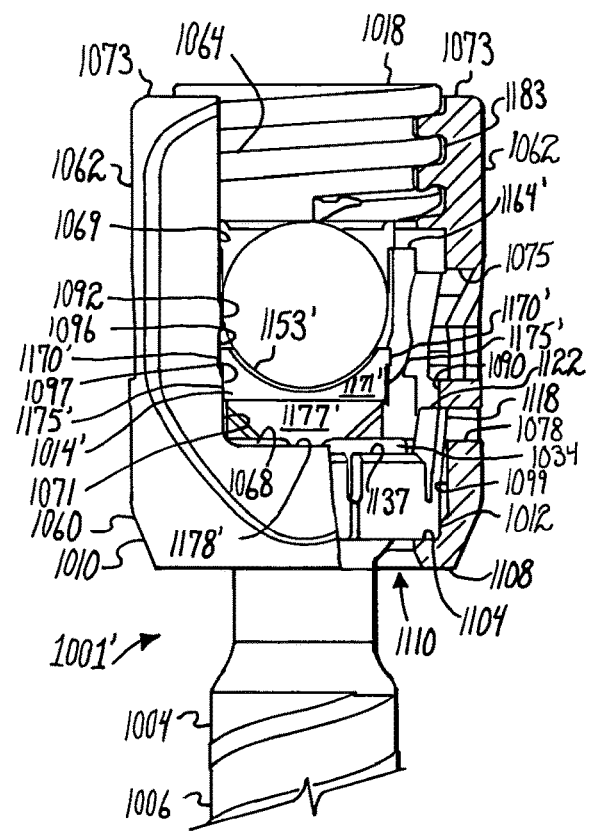
FIG. 97 is a reduced and partial front elevational view of the shank, receiver, retainer, rod and closure of FIG. 59, with portions broken away and assembled with the locking insert as shown in FIG. 96 in an interim unlocked stage of assembly.
Figure 98:
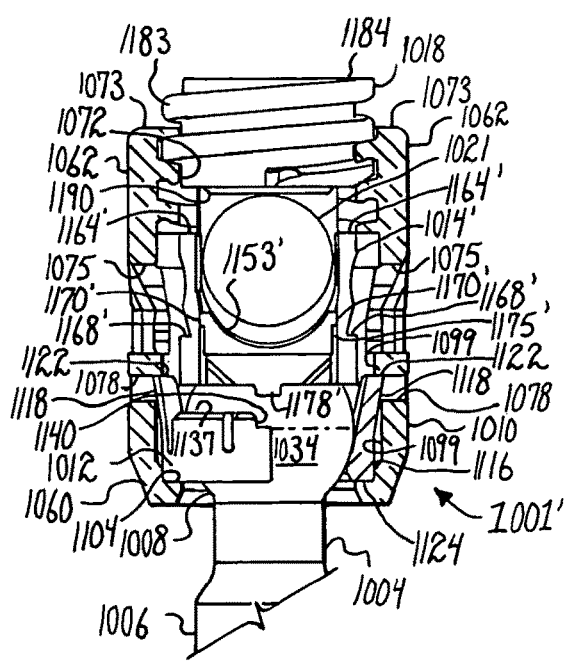
FIG. 98 is an enlarged and partial front elevational view of the shank, receiver, retainer, locking insert, rod and closure of FIG. 97, with portions broken away and shown in a final locked position.

With reference to FIGS. 93-98, an alternative lock-and-release compression insert 1014' is illustrated for use with the shank 1004, receiver 1010, retainer 1012, closure top 1018 and rod 1021 previously described herein, the resulting assembly identified as an assembly 1001' in FIGS. 97 and 98, for example. The insert 1014' is identical or substantially similar to the insert 1014 previously described herein, with the exception that the insert 1014' is sized for a locking interference fit with the edges 1097 and adjacent planar surfaces 1071 of the receiver 1010 as will be described in greater detail below.

Thus, the locking insert 1014 includes a body 1150', a pair of opposed ends 1151', a saddle surface 1153', a pair of arms 1157', a bore 1160', outer curved arm surfaces 1163', arm planar top surfaces 1164', an annular bottom surface 1165', a pair of v-shaped apertures that include arm through holes 1166', outer sloping surfaces 1167', and a lower planar surface 1168', extended portions with outer planar side surfaces 1170', planar end surfaces 1171', a pair of base extensions 1172', upper surfaces 1173', narrow lower ledges 1174', inset planar side surfaces 1175', lower body portions 1176' with planar surfaces 1177', protrusions 1178', surfaces 1179' on either side of the protrusions, an inner cylindrical surface 1180', an inner spherical surface 1181' and an inner gripping surface portion 1182' that are the same or substantially similar in form and function to the respective body 1150, pair of opposed ends 1151, the saddle surface 1153, arms 1157, bore 1160, outer curved arm surfaces 1163, arm planar top surfaces 1164, annular bottom surface 1165, v-shaped apertures that include arm through holes 1166, outer sloping surfaces 1167, and a lower planar surface 1168, the extended portions with outer planar side surfaces 1170, planar end surfaces 1171, the base extensions 1172, upper surfaces 1173, narrow lower ledges 1174, inset planar side surfaces 1175, lower body portions 1176 with planar surfaces 1177, protrusions 1178, surfaces 1179 on either side of the protrusions, and the inner cylindrical surface 1180, inner spherical surface 1181 and inner gripping surface portion 1182 previously described herein with respect to the insert 1014.

The insert 1014' planar side surfaces 1175' are sized and shaped for a locking interference fit with the receiver at a lower portion of the receiver channel 1064. In other words, a width measured between surfaces 1175' is sized large enough to require that the insert 1014' must be forced into the space between the receiver surfaces 1071 starting at the edge surfaces 1097 by a tool or tools or by the closure top 1018 forcing the rod 1021 downwardly against the insert 1014' with sufficient force to interferingly lock the insert into the receiver between the planar surfaces 1071.

With reference to FIGS. 96-98, the insert 1014' is assembled with the receiver 1010, retainer 1012, shank 1004, rod 1021 and closure top 1018, in a manner the same as previously described above with respect to the assembly 1001, resulting in an assembly 1001', with the exception that the insert 1014' must be forced downwardly into a locking interference fit with the receiver 1010 when the shank 1004 is locked in place, as compared to the easily sliding relationship between the insert 1014 and the receiver 1010. In particular, prior to assembly with the rod 1021 and the closure top 1018, the compression insert 1014' outer surfaces 1170' are slidingly received by receiver surfaces 1071, but the surfaces 1175' are not. The insert 1014' is thus prohibited from moving any further downwardly at the edges 1097 unless forced downwardly by a locking tool or by the closure top pressing downwardly on the rod that in turn presses downwardly on the insert 1014' as shown in FIGS. 97 and 98. With further reference to FIG. 97, at this time, the receiver 1010 may be articulated to a desired angular position with respect to the shank 1004, such as that shown in FIGS. 104 and 106, for example, that will be held, but not locked, by the frictional engagement between the retainer 1012 and the shank upper portion 1008.

The rod 1021 is eventually positioned in an open or percutaneous manner in cooperation with the at least two bone screw assemblies 1001'. The closure structure 1018 is then inserted into and advanced between the arms 1062 of each of the receivers 1010. The closure structure 1018 is rotated, using a tool engaged with the inner drive 1186 until a selected pressure is reached at which point the rod 1021 engages the U-shaped seating surface 1153' of the compression insert 1014', further pressing the insert spherical surface 1181' and stepped shank gripping surfaces 1182' against the shank spherical surface 1034, the edges of the stepped surfaces 1182' penetrating into the spherical surface 1034, pressing the shank upper portion 1008 into locked frictional engagement with the retainer 1012. Specifically, as the closure structure 1018 rotates and moves downwardly into the respective receiver 1010, the rim 1190 engages and penetrates the rod surface 1022, the closure structure 1018 pressing downwardly against and biasing the rod 1021 into compressive engagement with the insert 1014' that urges the shank upper portion 1008 toward the retainer 1012 and into locking engagement therewith, the retainer 1012 frictionally abutting the surface 1104 and expanding outwardly against the cylindrical surface 1101. For example, about 80 to about 120 inch pounds of torque on the closure top may be applied for fixing the bone screw shank 1006 with respect to the receiver 1010. Tightening the helical flange form to 100 inch pounds can create 1000 pounds of force and it has been found that an interference fit is created between the planar surfaces 1175' of the insert 1014' and the edges 1097 and planar surfaces 1071 of the receiver at between about 700-900 inch pounds. So, as the closure structure 1018 and the rod 1021 press the insert 1014 downwardly toward the base of the receiver 1010, the insert surfaces 1175' are forced into the receiver at the edges 1097, thus forcing and fixing the insert 1014 into frictional interference engagement with the receiver surfaces 1071.

With reference to FIG. 99, at this time, the closure top 1018 may be loosened or removed and/or the rod 1021 may be adjusted and/or removed and the frictional engagement between the insert 1014' and the receiver 1010 at the insert surfaces 1175' will remain locked in place, advantageously maintaining a locked angular position of the shank 1004 with respect to the receiver 1010.

With further reference to FIGS. 99 and 100, at this time, another rod, such as the deformable rod 1221 and cooperating alternative closure top 1218 may be loaded onto the already locked-up assembly to result in an alternative assembly 1201'. As mentioned above, the closure drive 1286 may advantageously be made smaller than the drive of the closure 1018, such that the deformable rod 1221 is not unduly pressed or deformed during assembly since the polyaxial mechanism is already locked.

With reference to FIGS. 101-103, a two-piece tool 1600 is illustrated for releasing the insert 1014' from the receiver 1010. The tool 1600 includes an inner flexible tube-like structure with opposed inwardly facing prongs 1612 located on either side of a through-channel 1616. The channel 1616 may terminate at a location spaced from the prongs 1612 or may extend further upwardly through the tool, resulting in a two-piece tool 1610. The tool 1600 includes an outer, more rigid tubular member 1620 having a smaller through channel 1622. The member 1620 slidingly fits over the tube 1610 after the flexible member 1610 prongs 1612 are flexed outwardly and then fitted over the receiver 1010 and then within through bores of the opposed apertures 1074 of the receiver 1010 and aligned opposed bores 1166' located on arms of the insert 1014'. In FIG. 101, the tool 1600 is shown during the process of unlocking the insert 1014' from the receiver 1010 with the outer member 6120 surrounding the inner member 1610 and holding the prongs 1612 within the receiver 1010 and insert 1014' apertures while the tool 1600 is pulled upwardly away from the shank 1004. It is foreseen that the tool 1600 may further include structure for pressing down upon the receiver 1010 while the prongs and tubular member are pulled upwardly, such structure may be located within the tool 1600 and press down upon the top surfaces 1073 of the receiver arms, for example.

Alternatively, another manipulation tool (not shown) may be used that is inserted into the receiver at the opening 1066 and into the insert channel formed by the saddle 1153', with prongs or extensions thereof extending outwardly into the insert through bores 1166'; a piston-like portion of the tool thereafter pushing directly on the shank upper portion 1008, thereby pulling the insert 1014' away from the receiver surface 1090 and thus releasing the polyaxial mechanism. At such time, the shank 1004 may be articulated with respect to the receiver 1010, and the desired friction fit returns between the retainer 1012 and the shank surface 1034, so that an adjustable, but non-floppy relationship still exists between the shank 1004 and the receiver 1010. If further disassembly of the assembly is desired, such is accomplished in reverse order to the procedure described previously herein for the assembly 1001.

With reference to FIGS. 104-106, another manipulation tool, generally 1700 is illustrated for independently locking the insert 1014' to the receiver 1010. The tool 1700 includes a pair of opposed arms 1712, each having an engagement extension 1716 positioned at an oblique angle with respect to the respective arm 1712 such that when the tool is moved downwardly toward the receiver, one or more inner surfaces 1718 of the engagement extension 1716 slide along the surfaces 1077 of the receiver and 1167' of the insert 1014' to engage the insert 1014', with a surface 1720 pressing downwardly on the insert surfaces 1168', pushing the planar surfaces 1175' into an interference locking fit within the receiver edge 1097 and surfaces 1072. As shown in FIG. 106, when the insert 1014' is locked against the receiver 1010, the tool bottom surfaces 1720 do not bottom out on the receiver surfaces 1075', but remain spaced therefrom. In the illustrated embodiment, the surface 1718 is slightly rounded and each arm extension 1716 further includes a planar lower surface 1722 that creates an edge with the bottom surface 1720 for insertion and gripping of the insert 1014' at the juncture of the surface 1167' and the surface 1168'. The tool 1700 may include a variety of holding and pushing/pulling mechanisms, such as a pistol grip tool, that may include a ratchet feature, a hinged tool, or, a rotatably threaded device, for example.

It is to be understood that while certain forms of the present invention have been illustrated and described herein, it is not to be limited to the specific forms or arrangement of parts described and shown.

What is claimed is:

1. A pivotal bone anchor assembly for securing a rod to a bone of a patient via temporary independent locking with an insert compressing tool prior to a final locking of the assembly with a closure, the pivotal bone assembly comprising:
   a receiver comprising:
      a base defining a lower portion of a central opening centered around a vertical centerline axis and communicating with a bottom surface of the receiver through a bottom opening;
      a pair of upright arms extending upward from the base to define an open channel configured to receive the rod;
      the central opening extending upward through the open channel to tops of the upright arms with a closure-mating structure adjacent the tops of the upright arms configured to cooperate with the closure to capture the rod within the open channel; and
      the upright arms including tool engaging structures configured for non-threaded releasable overlapping engagement with the insert compressing tool; and
   a bone anchor comprising a longitudinal axis, a capture head configured for being pivotably disposed within the lower portion of the central opening with the bone anchor extending downward through the bottom opening, and an anchor portion opposite the capture head configured for fixation to the bone;
   a compression insert configured for positioning within the central opening of the receiver above the capture head, the compression insert comprising:

an upper surface configured for engagement with the rod;

a center through bore configured to receive a drive tool; and upward-facing tool engagement surfaces located radially outward from the center through bore, wherein the tool engaging structures of the upright arms and the upward-facing tool engagement surfaces of the insert are configured for simultaneous non-threadable engagement with the insert compressing tool so as to apply a downwardly-directed force to the capture head of the bone anchor configured to temporarily independently lock an articulated position of the bone anchor with respect to the receiver, with the longitudinal axis of the bone anchor in non-alignment with the vertical centerline axis of the receiver, prior to securing the rod within the open channel with the closure.

2. The pivotal bone anchor assembly of claim 1, wherein the compression insert is operable to receive the downwardly-directed force from the insert compressing tool during installation of the rod into the open channel and the closure into the central opening.

3. The pivotal bone anchor assembly of claim 1, wherein the upward-facing tool engagement surfaces of the compression insert are located diametrically opposite each other.

4. The pivotal bone anchor assembly of claim 1, wherein the compression insert is configured to be downloaded into the central opening of the receiver.

5. The pivotal bone anchor assembly of claim 1,
wherein the capture head of the bone anchor includes a partial spherical upper surface, and
wherein the compression insert includes a partial spherical lower surface configured to directly engage the partial spherical upper surface of the capture head of the bone anchor to apply to the downwardly-directed force.

6. The pivotal bone anchor assembly of claim 1, wherein the closure-mating structure of the central opening further comprises a helically wound threadform.

7. The pivotal bone anchor assembly of claim 1, further comprising side apertures extending through the upright arms of the receiver below the closure-mating structure.

8. The pivotal bone anchor assembly of claim 7, wherein the side apertures further comprise upper tool alignment surfaces configured to guide distal end portions of the insert compressing tool into the engagement with the upward-facing tool engagement surfaces of the compression insert.

9. The pivotal bone anchor assembly of claim 8, wherein the upper tool alignment surfaces are downwardly and inwardly sloping surfaces.

10. The pivotal bone anchor assembly of claim 1, wherein the bone anchor is a shank and the anchor portion is a helically wound bone implantable thread at a distal end of the shank.

11. The pivotal bone anchor assembly of claim 1, wherein the bone anchor further comprises a cannulated shank with an axial opening extending along an entire length thereof.

12. The pivotal bone anchor assembly of claim 1, wherein the capture head of the bone anchor is uploadable into the central opening of the receiver through the bottom opening.

13. The pivotal bone anchor assembly of claim 1 and further comprising a retainer positionable within the lower portion of a central opening prior to the capture head of the bone anchor and operable to capture the capture head upon an uploading of the capture head through the bottom opening.

14. The pivotal bone anchor assembly of claim 13, wherein the retainer is non-pivotal with respect to the receiver after the capture of the capture head of the bone anchor.

15. The pivotal bone anchor assembly of claim 1 and further comprising the rod and the closure, and wherein the closure includes a receiver-mating structure formed into an outer sidewall surface and engageable with the closure-mating structure of the central opening of the receiver to capture the rod within the open channel.

16. The pivotal bone anchor assembly of claim 15, wherein the upward-facing tool engagement surfaces of the compression insert are configured to remain uncovered by the rod or by the closure.

17. A pivotal bone anchor system comprising the pivotal bone anchor assembly of claim 1 and further comprising the insert compressing tool, wherein the insert compressing tool includes downward-facing surfaces complementary with the upward-facing tool engagement surfaces of the compression insert.

18. The pivotal bone anchor system of claim 17, wherein the upward-facing tool engagement surfaces of the compression insert and the downward-facing surfaces of the insert compressing tool are substantially planar.

* * * * *